(12) United States Patent
Sharp

(10) Patent No.: US 10,087,446 B2
(45) Date of Patent: Oct. 2, 2018

(54) METHODS AND COMPOSITIONS TO INHIBIT METASTASIS AND TO TREAT FIBROSIS AND TO ENHANCE WOUND HEALING

(71) Applicant: ALBERT EINSTEIN COLLEGE OF MEDICINE, INC., Bronx, NY (US)

(72) Inventor: David Sharp, Scardale, NY (US)

(73) Assignee: Albert Einstein College of Medicine, Inc., Bronx, NY (US)

( * ) Notice: Subject to any disclaimer, the term of this patent is extended or adjusted under 35 U.S.C. 154(b) by 0 days.

(21) Appl. No.: 15/706,849

(22) Filed: Sep. 18, 2017

(65) Prior Publication Data
US 2018/0057816 A1     Mar. 1, 2018

Related U.S. Application Data

(62) Division of application No. 15/023,869, filed as application No. PCT/US2014/055393 on Sep. 12, 2014, now Pat. No. 9,994,845.

(60) Provisional application No. 61/885,676, filed on Oct. 2, 2013.

(51) Int. Cl.
*C12N 15/11* (2006.01)
*C12N 15/113* (2010.01)
*C07K 14/47* (2006.01)

(52) U.S. Cl.
CPC ........ *C12N 15/113* (2013.01); *C07K 14/4738* (2013.01); *C12Y 306/04004* (2013.01); *C12N 2310/14* (2013.01)

(58) Field of Classification Search
None
See application file for complete search history.

(56) References Cited

U.S. PATENT DOCUMENTS

2008/0139492 A1    6/2008   Ruvkun
2010/0015050 A1    1/2010   Panyam

FOREIGN PATENT DOCUMENTS

WO          2007104011 A2    9/2007

OTHER PUBLICATIONS

PCT International Search Report and Written Opinion, dated Jan. 2, 2015 in connection with PCT International Application No. PCT/US2014/055393, 14 pages.
Gomez-Ferreria et al., entitled "Human Cep192 is required for mitotic centrosome and spindle assembly," Current Biology, Nov. 20, 2007, vol. 17, Iss. 22, pp. 1960-1966.
Niwa et al., entitled "KIF19A is a microtubule-depolymerizing kinesin for ciliary length control," Developmental Cell, Dec. 11, 2012, vol. 23, Iss. 6, pp. 1167-1175.
Zhu et al., entitled "The mammalian SPD-2 ortholog Cep192 regulates centrosome biogenesis," Current Biology, Jan. 22, 2008, vol. 18, Iss. 2, pp. 136-141.
Enoch et al., entitled "Cellular, molecular and biochemical differences in the pathophysiology of healing between acute wounds, chronic wounds, and wounds in the aged," World Wide Wounds, Aug. 13, 2004, pp. 1-15. Retrieved from the Internet:<http://www.worldwidewounds.com/2004/august/Enoch/Pathophysiology-Of-Healing.html> on Dec. 8, 2014.
Miki et al., entitled "All kinesin superfamily protein, KIF, genes in mouse and human," Proceedings of the National Academy of Sciences, Jun. 19, 2001, vol. 98, Iss. 13, pp. 7004-7011.
Dumontet et al., entitled "Microtubule-binding agents: a dynamic field of cancer therapeutics," National Review of Drug Discoveries, Oct. 17, 2011, vol. 9, Issue 10, pp. 790-803.
Schairer et al., entitled "Fidgetin-like 2 siRNA and Kif19 siRNA loaded nanoparticles alter wound healing speeds in a murine wound model," Nov. 2012, Journal of Investigative Dermatology, vol. 132, abstract 791, p. S136.
Groth-Pedersen et al., entitled "Identification of cytoskeleton-associated proteins essential for cancer cell survival and lysosomal stability," Sep. 2011, 19th Euroconference on Apoptosis, poster P-3, p. 76.
Shinsuke et al., entitled "KIF19A is a Microtubule-Depolymerizing Kinesin for Ciliary Length Control," Developmental Cell, vol. 23, No. 6, Dec. 1, 2012, pp. 1167-1175.
Communication Supplementary European Search Report dated Aug. 21, 2017 from the European Patent Office in connection with European Patent Application No. 14850548.0.

*Primary Examiner* — Ekaterina Poliakova-Georgantas
(74) *Attorney, Agent, or Firm* — Amster, Rothstein & Ebenstein LLP

(57) ABSTRACT

Methods and compositions are provided for inhibiting or treating metastasis based on discoveries regarding Kif19 and Cep192. Methods and compositions are provided for enhancing wound healing, treating fibrosis, reducing scarring and treating nerve pain.

18 Claims, 17 Drawing Sheets

Specification includes a Sequence Listing.

SEQUENCE LISTING

<160> NUMBER OF SEQ ID NOS: 9

<210> SEQ ID NO 1
<211> LENGTH: 3670
<212> TYPE: DNA
<213> ORGANISM: Homo sapiens

<400> SEQUENCE: 1

```
gcgttgttgg tttcgggttg tcaggcagcg cgcgaggcgg cgggcagcta gcagctggcg        60
gacgcgaccc ggaggcggtg ggggtgcggc tgagccatgc ccggtggcgc ggcctgagcc       120
cctccacctg ctgcaatcat gaaggacagc ggggactcca aggaccagca actcatggtg       180
gcgcttcggg tccggcccat cagcgtggca gagctggagg aaggagctac cctcatcgcc       240
cataaagtgg atgagcagat ggtggttctc atggacccaa tggaggatcc cgacgacatc       300
ctgcgggcgc atcgctcccg ggagaagtcc tacctgttcg acgtggcctt tgacttcacc       360
gccacccagg agatggtgta tcaggccacc accaagagcc tcatcgaggg cgtcatctca       420
ggctacaatg ccactgtctt tgcctatggc cccacaggct gtgggaaaac ctacaccatg       480
ctgggcacag accaggagcc tggcatctat gttcagaccc tcaacgacct cttccgtgcc       540
atcgaggaga ccagcaatga catggagtat gaggtctcca tgtcctacct ggagatctac       600
aatgagatga tccgggacct gctgaaccc tccctgggct acctggagct gcgggaggac       660
tctaagggg tgatccaggt ggccggcatc accgaagtct ccaccatcaa tgccaaggag       720
atcatgcagc tgctgatgaa ggggaaccgg cagaggaccc aggagcccac ggccgccaac       780
cagacgtcct cccgctccca cgcggtactg caggtgaccg tgcgccagcg cagccgggtc       840
aagaacatct tgcaggaggt gcggcagggc cgcctgttca tgatcgacct ggctggctca       900
gagcgcgcct cgcagacaca gaatcgtggg cagcgtatga aggagggggc ccacatcaac       960
cgctcactgc tggcactggg caactgcatc aacgccctga gcgacaaggg tagcaacaag      1020
tacatcaact atcgcgacag caagctcacc cggctcctga aggactctct gggaggaaac      1080
agccgcacag tgatgatcgc tcacatcagt cctgcgagca gtgccttcga ggagtcccgg      1140
aacaccctga cctacgccgg ccgggccaag aacattaaga ctagggtgaa gcagaacctc      1200
ctgaacgtct cctaccacat cgcccagtac accagcatca tcgctgacct gcggggcgag      1260
atccagcgac tcaagcgcaa gattgatgag cagactgggc ggggccaggc ccggggccgg      1320
caggatcggg gtgacatccg ccacatccaa gctgaggtcc agctgcacag cgggcagggt      1380
gagaaggctg gcatgggaca gcttcgggag cagctcgcca gcgccttcca ggagcagatg      1440
gatgtgcgga gcgcctgct ggagctggag aaccgcgcca tggaggtcca gattgacacc      1500
tcccgacacc tgctcaccat cgccggctgg aagcatgaga agtcccgccg ggccctcaaa      1560
tggcgggagg agcagcgaaa ggagtgctac gctaaggacg acagcgagaa ggactcagac      1620
acaggtgatg accaaccaga catcctggag ccacccgagg tggccgcagc ccgggagagc      1680
attgcagccc tggtggacga gcagaagcaa ctgcgcaagc agaagctggc gctggagcag      1740
cgctgccggg agctgcgcgc gcggggccgg cgcctggagg acgctgcc gcggcgcatc      1800
ggctccgagg agcagcgcga ggtgctcagc ctgctgtgcc gcgtgcacga gctcgaggtg      1860
gagaacaccg agatgcagtc gcacgcgctg ctccgcgacg gtgcgctccg ccaccgccac      1920
```

-continued

```
gaggccgtgc gccgcctgga gcagcaccgc agtctctgcg acgagattat ccagggccag    1980
cggcagatca tcgacgacta caacctggcc gtcccgcagc gcctggaaga gctctacgaa    2040
gtgtacctgc gggagctgga ggagggcagc ctggagcagg ccaccatcat ggaccaagtg    2100
gcctccaggg ccctgcagga cagctccttg cccaaaatta ccccagcagg aacctcactg    2160
accccagatt ctgacctgga gagtgtgaag acattgagct ctgatgccca gcacctgcag    2220
aacagcgccc tccctcccct cagcacagag agtgaaggcc accacgtgtt caaggctggt    2280
actggggcct ggcaggcaaa aagctcctct gtgcccaccc cacctcccat ccagctcggc    2340
agcctggtga cgcaggaggc cccggctcag gacagcctgg gcagctggat caactcttcc    2400
cctgacagca gtgagaacct gtcggagatc cccttgtccc acaaagagag gaaggagatc    2460
ctgactggca ccaagtgcat ctgggtgaag gccgcccggc ggcgctcgcg ggccctggga    2520
accgaggggc gacacctgct ggcacccgcg acagagcgca gcagcctgtc cctgcactca    2580
ctgagcgagg gcgacgatgc gcggccacca ggcccactgg cctgcaagcg gccgcccagc    2640
cccacactac agcatgctgc cagtgaggac aacctgtcca gcagcacggg cgaggccccg    2700
tcccggggcag tcggacatca tggggacggc cccaggccct ggctgcgtgg ccagaagaaa    2760
agcctgggca agaaaaggga ggagtcgctg gaggcaaaga gaaggaagcg gaggtcccga    2820
tccttcgagg tcaccgggca agggctctcc caccccaaga cacacctcct ggggccccat    2880
caggcggagc gcatctcgga ccacaggatg ccagtgtgca ggcacccagc ccctggtatc    2940
cggcatctgg gaaaggtcac gctacctttg gccaaagtca aactcccctcc aagccagaac    3000
acgggccccgg gggactcctc accccctggct gttcccccca acccaggtgg tggttctcga    3060
cgggctaccc gtgggccccg cctgccccac ggcacaagca cccatggcaa agatggatgc    3120
tcccggcata actgaggggc cctgcctgga actggctctc tcacctccca agactgaatg    3180
gggtctagca gggcatggga ggtggaggct gggcagatgg agatgaccag gaagtaagct    3240
caggatctca gcaggccagg gctcctgaga cccaggaact ggggtctctg cccaaccctc    3300
ccatgctttc agtgccactg gggaaaagag gtgaggccag gggacatggc caggacggct    3360
gggctccctg gcttcccagc cctggacaga atgctgttgc caaaacctgc acagccctga    3420
ggccagcctc ggccttggta acggaggaaa gcagctgaca gtgagacggg gctcctggcc    3480
cacgtgtggg gcacgggcat cctggatggt tggggaggcg ccgacaggca cttcacgtat    3540
tacaattggg gatgtgggtg agggagggaa tctggttttg ttacttggca gtggtttttt    3600
ctcacccttc cttttttaaca ataaaatccc atttgggtct tgaaaaaaaa aaaaaaaaa    3660
aaaaaaaaaa                                                          3670
```

<210> SEQ ID NO 2
<211> LENGTH: 998
<212> TYPE: PRT
<213> ORGANISM: Homo sapiens

<400> SEQUENCE: 2

```
Met Lys Asp Ser Gly Asp Ser Lys Asp Gln Gln Leu Met Val Ala Leu
1               5                   10                  15

Arg Val Arg Pro Ile Ser Val Ala Glu Leu Glu Glu Gly Ala Thr Leu
            20                  25                  30

Ile Ala His Lys Val Asp Glu Gln Met Val Val Leu Met Asp Pro Met
        35                  40                  45

Glu Asp Pro Asp Asp Ile Leu Arg Ala His Arg Ser Arg Glu Lys Ser
    50                  55                  60
```

```
Tyr Leu Phe Asp Val Ala Phe Asp Phe Thr Ala Thr Gln Glu Met Val
 65                  70                  75                  80

Tyr Gln Ala Thr Thr Lys Ser Leu Ile Glu Gly Val Ile Ser Gly Tyr
                 85                  90                  95

Asn Ala Thr Val Phe Ala Tyr Gly Pro Thr Gly Cys Gly Lys Thr Tyr
            100                 105                 110

Thr Met Leu Gly Thr Asp Gln Glu Pro Gly Ile Tyr Val Gln Thr Leu
            115                 120                 125

Asn Asp Leu Phe Arg Ala Ile Glu Glu Thr Ser Asn Asp Met Glu Tyr
            130                 135                 140

Glu Val Ser Met Ser Tyr Leu Glu Ile Tyr Asn Glu Met Ile Arg Asp
145                 150                 155                 160

Leu Leu Asn Pro Ser Leu Gly Tyr Leu Glu Leu Arg Glu Asp Ser Lys
                165                 170                 175

Gly Val Ile Gln Val Ala Gly Ile Thr Glu Val Ser Thr Ile Asn Ala
            180                 185                 190

Lys Glu Ile Met Gln Leu Leu Met Lys Gly Asn Arg Gln Arg Thr Gln
            195                 200                 205

Glu Pro Thr Ala Ala Asn Gln Thr Ser Ser Arg Ser His Ala Val Leu
210                 215                 220

Gln Val Thr Val Arg Gln Arg Ser Arg Val Lys Asn Ile Leu Gln Glu
225                 230                 235                 240

Val Arg Gln Gly Arg Leu Phe Met Ile Asp Leu Ala Gly Ser Glu Arg
                245                 250                 255

Ala Ser Gln Thr Gln Asn Arg Gly Gln Arg Met Lys Glu Gly Ala His
            260                 265                 270

Ile Asn Arg Ser Leu Leu Ala Leu Gly Asn Cys Ile Asn Ala Leu Ser
            275                 280                 285

Asp Lys Gly Ser Asn Lys Tyr Ile Asn Tyr Arg Asp Ser Lys Leu Thr
            290                 295                 300

Arg Leu Leu Lys Asp Ser Leu Gly Gly Asn Ser Arg Thr Val Met Ile
305                 310                 315                 320

Ala His Ile Ser Pro Ala Ser Ser Ala Phe Glu Glu Ser Arg Asn Thr
                325                 330                 335

Leu Thr Tyr Ala Gly Arg Ala Lys Asn Ile Lys Thr Arg Val Lys Gln
            340                 345                 350

Asn Leu Leu Asn Val Ser Tyr His Ile Ala Gln Tyr Thr Ser Ile Ile
            355                 360                 365

Ala Asp Leu Arg Gly Glu Ile Gln Arg Leu Lys Arg Lys Ile Asp Glu
            370                 375                 380

Gln Thr Gly Arg Gly Gln Ala Arg Gly Arg Gln Asp Arg Gly Asp Ile
385                 390                 395                 400

Arg His Ile Gln Ala Glu Val Gln Leu His Ser Gly Gln Gly Glu Lys
                405                 410                 415

Ala Gly Met Gly Gln Leu Arg Glu Gln Leu Ala Ser Ala Phe Gln Glu
            420                 425                 430

Gln Met Asp Val Arg Arg Leu Leu Glu Leu Glu Asn Arg Ala Met
            435                 440                 445

Glu Val Gln Ile Asp Thr Ser Arg His Leu Leu Thr Ile Ala Gly Trp
450                 455                 460

Lys His Glu Lys Ser Arg Arg Ala Leu Lys Trp Arg Glu Glu Gln Arg
465                 470                 475                 480
```

```
Lys Glu Cys Tyr Ala Lys Asp Asp Ser Glu Lys Asp Ser Asp Thr Gly
                485                 490                 495

Asp Asp Gln Pro Asp Ile Leu Glu Pro Pro Glu Val Ala Ala Arg
            500                 505                 510

Glu Ser Ile Ala Ala Leu Val Asp Glu Gln Lys Gln Leu Arg Lys Gln
            515                 520                 525

Lys Leu Ala Leu Glu Gln Arg Cys Arg Glu Leu Arg Ala Arg Gly Arg
    530                 535                 540

Arg Leu Glu Glu Thr Leu Pro Arg Arg Ile Gly Ser Glu Glu Gln Arg
545                 550                 555                 560

Glu Val Leu Ser Leu Leu Cys Arg Val His Glu Leu Glu Val Glu Asn
                565                 570                 575

Thr Glu Met Gln Ser His Ala Leu Leu Arg Asp Gly Ala Leu Arg His
            580                 585                 590

Arg His Glu Ala Val Arg Arg Leu Glu Gln His Arg Ser Leu Cys Asp
    595                 600                 605

Glu Ile Ile Gln Gly Gln Arg Gln Ile Ile Asp Asp Tyr Asn Leu Ala
610                 615                 620

Val Pro Gln Arg Leu Glu Glu Leu Tyr Glu Val Tyr Leu Arg Glu Leu
625                 630                 635                 640

Glu Glu Gly Ser Leu Glu Gln Ala Thr Ile Met Asp Gln Val Ala Ser
                645                 650                 655

Arg Ala Leu Gln Asp Ser Ser Leu Pro Lys Ile Thr Pro Ala Gly Thr
                660                 665                 670

Ser Leu Thr Pro Asp Ser Asp Leu Glu Ser Val Lys Thr Leu Ser Ser
            675                 680                 685

Asp Ala Gln His Leu Gln Asn Ser Ala Leu Pro Pro Leu Ser Thr Glu
    690                 695                 700

Ser Gly His His Val Phe Lys Ala Gly Thr Gly Ala Trp Gln Ala
705                 710                 715                 720

Lys Ser Ser Ser Val Pro Thr Pro Pro Ile Gln Leu Gly Ser Leu
                725                 730                 735

Val Thr Gln Glu Ala Pro Ala Gln Asp Ser Leu Gly Ser Trp Ile Asn
            740                 745                 750

Ser Ser Pro Asp Ser Ser Glu Asn Leu Ser Glu Ile Pro Leu Ser His
        755                 760                 765

Lys Glu Arg Lys Glu Ile Leu Thr Gly Thr Lys Cys Ile Trp Val Lys
    770                 775                 780

Ala Ala Arg Arg Arg Ser Arg Ala Leu Gly Thr Glu Gly Arg His Leu
785                 790                 795                 800

Leu Ala Pro Ala Thr Glu Arg Ser Ser Leu Ser Leu His Ser Leu Ser
                805                 810                 815

Glu Gly Asp Asp Ala Arg Pro Pro Gly Pro Leu Ala Cys Lys Arg Pro
                820                 825                 830

Pro Ser Pro Thr Leu Gln His Ala Ala Ser Glu Asp Asn Leu Ser Ser
            835                 840                 845

Ser Thr Gly Glu Ala Pro Ser Arg Ala Val Gly His His Gly Asp Gly
    850                 855                 860

Pro Arg Pro Trp Leu Arg Gly Gln Lys Lys Ser Leu Gly Lys Lys Arg
865                 870                 875                 880

Glu Glu Ser Leu Glu Ala Lys Arg Arg Lys Arg Arg Ser Arg Ser Phe
                885                 890                 895

Glu Val Thr Gly Gln Gly Leu Ser His Pro Lys Thr His Leu Leu Gly
```

```
            900             905             910
Pro His Gln Ala Glu Arg Ile Ser Asp His Arg Met Pro Val Cys Arg
        915                 920                 925

His Pro Ala Pro Gly Ile Arg His Leu Gly Lys Val Thr Leu Pro Leu
        930                 935                 940

Ala Lys Val Lys Leu Pro Ser Gln Asn Thr Gly Pro Gly Asp Ser
945                 950                 955                 960

Ser Pro Leu Ala Val Pro Pro Asn Pro Gly Gly Ser Arg Arg Ala
            965                 970                 975

Thr Arg Gly Pro Arg Leu Pro His Gly Thr Ser Thr His Gly Lys Asp
        980                 985                 990

Gly Cys Ser Arg His Asn
        995

<210> SEQ ID NO 3
<211> LENGTH: 7995
<212> TYPE: DNA
<213> ORGANISM: Homo sapiens

<400> SEQUENCE: 3
```

| | | | | | |
|---|---|---|---|---|---|
| agtgccctgg | gacacctctt | cagtccgtgg | actttcccgc | tgcacactgc | cctccgaagt | 60 |
| cggggacgcg | ggctcgtgag | atggaagatt | ttcgaggtat | agcagaagaa | tcatttccaa | 120 |
| gctttctcac | caattcatta | tttggtaaca | gtgggatttt | ggaaaatgtc | actctttctt | 180 |
| caaatcttgg | cttgcctgtt | gctgtttcta | cacttgctag | ggatagatcc | agcactgata | 240 |
| acaggtatcc | tgatatccag | gcatcttact | tagtagaagg | gagattttca | gttccatccg | 300 |
| ggtcatctcc | cggaagccag | agtgatgctg | aaccaagaga | gaggttacag | cttagcttcc | 360 |
| aggatgatga | ttctatctct | aggaaaaaga | gctatgtgga | aagtcaacgt | ttgtcaaatg | 420 |
| ctctcagcaa | acagtcagct | ttacaaatgg | agacagcagg | accagaagag | gagccagccg | 480 |
| gagctacaga | atccttgcag | ggccaagatc | tcttcaacag | gcttcaccca | ctggaacaag | 540 |
| cacaagactc | acctattgat | tttcatttac | agtcatggat | gaataataag | gaacccaaga | 600 |
| tgttgtgct | tgatgctgga | aaacattttg | aagacaagac | tctaaagagt | gacctaagcc | 660 |
| acactagctt | attagaaaat | gagaaactta | tcttaccgac | aagcttggaa | gattcttctg | 720 |
| atgatgatat | tgatgatgaa | atgttttatg | atgatcattt | ggaggcttat | tttgaacaac | 780 |
| tggcaattcc | aggaatgata | tatgaagacc | tagaaggacc | agaacctcca | gaaaaaggtt | 840 |
| ttaagttacc | tacaaatggt | cttagacagg | caaatgaaaa | cggtagctta | aactgcaagt | 900 |
| ttcaatcaga | aaataacagc | tctctgattt | ccctcgactc | acactcttct | gaaacaactc | 960 |
| acaaagagtc | tgaggaaagc | caagttattt | gtctacctgg | gactagtaat | tctataggta | 1020 |
| ctggagatag | tagaaggtac | acagatggta | tgttaccatt | ttcctctggt | acttggggaa | 1080 |
| ctgagaaaga | aatagaaaat | ttgaagggta | ttgttccaga | tcttaacagt | gaatgtgcaa | 1140 |
| gtaaagatgt | tctggtgaag | accctcaggg | ctattgatgt | gaaacttaac | tctgataatt | 1200 |
| tcatgatgc | aaatgccaat | agaggtggtt | ttgatctgac | tgaccctgta | aaacaggggg | 1260 |
| cagagtgtcc | tcaccaaaat | aagacagttt | tgcacatgga | tggatgttta | gacactgaga | 1320 |
| ctcctacggt | gtccattcaa | gaaaatgtgg | atgtagcctc | tttgaagccc | attagtgaca | 1380 |
| gtggaattaa | tttcactgat | gccatttggt | caccaacttg | tgaaaggcga | acatgtgaat | 1440 |
| gtcacgagtc | catcgaaaag | aataaagaca | aaacagatct | cccacagagt | gtggtctatc | 1500 |
| aaaatgaaga | gggtaggtgg | gtcacagacc | ttgcctatta | cacatctttt | aatagcaaac | 1560 |

```
aaaatttaaa tgtgtctcta agtgatgaga tgaatgaaga cttcagatct ggttctgaag    1620
catttgattt gattgcacaa gatgaagaag aatttaataa agagcatcaa tttatacagg    1680
aagaaaacat agatgctcat aatacttcgg ttgcactggg cgatacgtcc tggggagcta    1740
caattaatta cagtctgttg aggaaatcac gtagcacatc agatttggat aaagatgatg    1800
ccagttattt acgtctgtct ttaggagagt tctttgctca aagatctgaa gctcttggtt    1860
gccttggtgg tggtaacaat gtgaaaagac catcatttgg ctatttatt agatcaccag     1920 agaagagaga acctattgcc ttaataagaa aatctgatgt atcaagaggt aatttggaaa    1980
aagaaatggc tcatcttaac catgatctat attcaggaga tttaaatgaa cagtcccagg    2040
cacagctaag tgaaggatca attacacttc aggttgaagc agtagagagt acttcacaag    2100
tggatgaaaa tgatgtgacg ttaacggctg ataaaggcaa aacagaggac actttcttca    2160
tgagcaacaa accccaaaga tacaaagaca agctaccaga tagtggtgat tctatgctta    2220
ggatcagcac cattgcttca gccattgcag aggcatcagt taatactgat ccttcccaac    2280
ttgctgcaat gatcaaggca cttttcaaata aaaccagaga caagacttttt caggaagatg   2340 agaaacaaaa ggactattct catgtgcgtc atttcttacc taatgattta gaaaaaagta    2400
atggatccaa tgcacttgat atggagaaat accttaaaaa aacagaagtt agtagatatg    2460
aaagtgcatt ggaaaacttt tcaagggcta gtatgtctga tacttgggat ttatctttgc    2520
ccaaagaaca aactactcaa gacattcatc cggtggactt aagtgctact agtgtaagtg    2580
tgagggcacc agaagaaaac acagcagcta ttgtttatgt tgaaaatgga gagagtgaga    2640
atcaagagtc atttagaacc ataaactcct caaattcagt tacaaataga gagaataaca    2700
gtgcagtagt tgatgtgaag acatgttcca ttgacaacaa attacaagat gttggtaacg    2760
atgaaaaagc tacctcaatt tccactccat ctgatagtta ttcatcagtg aggaaccccca   2820 gaataacatc cctttgtctg ttaaaagact gtgaagaaat acgagataac agagaaaatc    2880
agaggcaaaa tgagtgtgtc agtgaaataa gcaacagtga gaagcatgtg acttttgaaa    2940
accatcgcat agtctcacct aaaaatagtg atttgaaaaa tacctctcct gagcatggtg    3000
gacgtggctc agaggatgag caggagagct tcagaccttc cacgtcacca ctgagtcatt    3060
cttctcctag tgaaatttct ggaacgagtt catcagggtg tgcgttagag tcctttggtt    3120
cagcagctca gcagcagcag cctccctgtg agcaggagtt gtctcccttg gtgtgctcgc    3180
ctgctggggt gagcaggctg acgtatgtgt ctgaaccaga gagctcctat cctaccacag    3240
ccacagatga tgccctggag gaccgcaaga gtgatatcac cagcgagttg agtaccacaa    3300
ttattcaagg cagtccagcc gcattggagg aacgggctat ggaaaaattg agagaaaaag    3360
ttccatttca gaatagagga aaaggaacat tatcatctat tatccagaat aactctgata    3420
caagaaaagc aactgaaact acttctctga gtagcaagcc tgaatatgta aaacctgact    3480
ttagatggag taaagatcct tcctccaaaa gtggaaatct gttggaaacc agtgaggtag    3540
gttggacatc aaaccctgag gaattggacc cgatcaggct ggctctcctg ggcaagtcag    3600
gtctgagctg tcaggtgggg tcagccacat cacaccctgt gtcctgccag gagcctatag    3660
atgaagatca aagaataagt cctaaagata agtcaactgc tggccgtgag ttcagtggcc    3720
aggtttctca tcagaccacc tctgaaaacc agtgtactcc tattcccagc agcacagttc    3780
acagctctgt ggctgacatg cagaaatatgc ctgctgctgt gcacgcactc ttgacacaac   3840
cctctctcag cgctgctcct tttgctcagc ggtatttggg aacactccct tcaactggaa    3900
```

```
gcaccacctt gcctcagtgc catgctggca atgccacagt ctgtggcttc tcaggaggcc    3960
ttccctatcc agctgttgca ggagagcctg tgcagaactc tgtggctgtg ggaatttgtc    4020
taggatcaaa tatcggctct ggatggatgg gtacctcttc cctctgtaac ccatattcta    4080
ataccttaaa tcagaacctg ctaagcacaa caaaaccttt tcctgtgccg tctgttggta    4140
caaactgtgg aattgaacca tgggattcag gagtgacatc aggattgggg agtgtccgag    4200
tgcccgagga gttgaagctt cctcatgctt gctgtgtcgg gatcgcttcc cagaccctcc    4260
tcagtgtgct taatccaact gaccgctggc tgcaagtcag cattggggtc ctcagcatta    4320
gtgttaatgg tgaaaaggtg gatctttcaa catatcgttg tttagttttc aagaataaag    4380
ccatcataag acctcatgcc acagaagaga taaaagtgct ttttatacca tccagtcctg    4440
gggttttcag atgcacattc agtgttgctt cttggccatg ttcgacagat gctgagacca    4500
tcgtacaggc agaagctttg gccagcaccg tcactctcac tgccattgcc gagagtcctg    4560
ttattgaggt agaaacagaa agaaagacg ttcttgattt tggtgacttg acttatggag    4620
gctggaaagc cctcccacta aaattgataa accgaacgca tgccactgtg ccaattagac    4680
tgattattaa tgctaacgct gtagcctggc gctgtttcac gttttccaag gaatccgtcc    4740
gagctcctgt ggaagttgct ccttgcgctg atgtggtcac tcggctagca ggcccttctg    4800
tggtcaacca catgatgcct gctagttatg atggacagga tccagaattt ctgatgattt    4860
gggttctttt ccatagtcca aagaaacaga tcagctcttc agatattctg gactcagcag    4920
aagaattctc ggcaaaagtt gatatcgaag ttgacagccc aaaccctacg cccgttctta    4980
gaagtgtgag tctccgagca agagcaggaa tagctaggat ccatgctccc agggacttgc    5040
agacgatgca tttcttggcc aaagtggctt cctcaagaaa gcagcactta cctttgaaaa    5100
atgctgggaa cattgaagtt tatttggata tcaaggtccc agaacaagga agtcactttt    5160
cagtggatcc aaagaatcta ctccttaaac ctggagaaga acatgaggtt attgtttcat    5220
ttactccaaa ggatcctgaa gcctgcgagg aaaggatctt gaaaatattt gtgcagccat    5280
ttggacctca gtatgaggta gtgttaaaag gcgaagtcat ttcttcagga agtaaacctc    5340
tgtcacctgg accttgctta gatattccat cgattttgtc caacaaacaa tttctggctt    5400
ggggaggagt ccctctaggt agaacacagc ttcagaaact agctttaaga ataattctg    5460 catctacaac tcaacattta cgactgctta ttagaggaca agatcaggac tgctttcagc    5520
ttcagaacac ttttggttca gaacagcgat tgaccagtaa ctgtgagatc agaattcacc    5580
caaaggaaga catttcatc tctgtattat ttgcacctac tcgattatct tgcatgttgg    5640
ctagactaga aatcaaacaa cttggaaatc gatcacaacc aggcattaag ttcacaatac    5700
ctttgtctgg atatggagga acaagcaatc ttattttgga aggcgttaaa aaattatctg    5760
acagttacat ggtaacagtg aatggcttag tacctggcaa agaaagtaaa attgtttttt    5820
ctgtccgcaa cactggctcc cgagcagctt ttgttaaagc agtaggtttt aaggattctc    5880 agaaaaagt tttgctggat cctaaagtat tgaggatttt tccagataaa tttgtactca    5940 aggaagaac acaagaaaat gttactttaa tatataatcc atcagacaga ggaatcaata    6000
ataaaactgc aacagaacta tcaactgtat acttatttgg tggagatgaa atttcaagac    6060
agcagtatcg cagggccctg ttacataaac cagagatgat aaaacagata cttccagaac    6120
atagtgtgct tcaaaacatt aatttttgttg aagcatttca agatgagcta ttagtaactg    6180
aagtatatga tcttcccccaa cgacctaatg atgttcagct cttttatgga agcatgtgta    6240
aaattatact ttcagtaatt ggagaattca gagattgcat ttctagcaga gaattccttc    6300
```

```
agccttcttc caaagctagc ttggaatcta caagcgactt gggagcttct gggaaacatg    6360
gtggcaacgt ctctttggat gttttaccag tcaaaggtcc tcagggttct cctcttctct    6420
cacgggcggc tcgcccgcct ctggatcagc tggcctccga agagccgtgg actgtcctac    6480
ccgagcactt gattctggta gctccttctc cttgtgacat ggcaaaaact ggacgtttcc    6540
agattgtgaa taactctgtg aggttactga gatttgagct gtgctggcca gcgcattgcc    6600
tcacagtcac gccgcagcat ggatgtgtcg cgccagagag taaactacaa attcttgtga    6660
gtcctaattc ctccttatcc acaaaacagt caatgttccc gtggagtggt ttgatctata    6720
tacactgtga cgatggacag aagaaaattg tgaaagttca aattcgagaa gatttaactc    6780
aagtggaact tttaactcgt ttgacctcca aaccatttgg aattctttcc ccagtatctg    6840
agccttcagt tagtcatttg gtcaaaccaa tgacaaaacc gccttccaca aaagttgaaa    6900
taagaaacaa gagtattact tttcctacaa cagaacctgg tgaaacttca gagagctgtc    6960
tagaactcga gaatcatggc accacagacg tgaaatggca tctgtcatct ttagcgccac    7020
cttatgtcaa gggagttgat gaaagtggag atgtttttag agctacctat gcagcattca    7080
gatgttctcc tatttctggt ctgctggaaa gccatgggat ccaaaaagtc tccatcacat    7140
ttttgcccag aggtaggggg gattatgccc agttttggga tgttgaatgt caccctctta    7200
aggagcctca catgaaacac acgttgagat tccaactctc tggacaaagc atcgaagcag    7260
aaaatgagcc tgaaaacgca tgcctttcca cggattccct cattaaaata gatcatttag    7320
ttaagccccg aagacaagct gtgtcagagg cttctgctcg catacctgag cagcttgatg    7380
tgactgctcg tggagtttat gccccagagg atgtgtacag gttccggccg actagtgtgg    7440
gggaatcacg gacacttaaa gtcaatctgc gaaataattc ttttattaca cactcactga    7500
agtttttgag tcccagagag ccattctatg tcaaacattc caagtactct ttgagagccc    7560
agcattacat caacatgccc gtgcagttca aaccgaagtc cgcaggcaaa tttgaagctt    7620
tgcttgtcat tcaaacagat gaaggcaaga gtattgctat tcgactaatt ggtgaagctc    7680
ttggaaaaaa ttaactagaa tacattttg tgtaaagtaa attacataag ttgtattttg    7740
ttaactttat ctttctacac tacaattatg cttttgtata tatattttgt atgatggata    7800
tctataattg tagattttgt ttttacaagc taatactgaa gactcgactg aaatattatg    7860
tatctagccc atagtattgt acttaacttt tacaggtgag aagagagttc tgtgtttgca    7920
ttgattatga tattctgaat aaatatggaa tatattttaa tgtggtatat ccagaaaaaa    7980
aaaaaaaaaa aaaaa                                                    7995
```

<210> SEQ ID NO 4
<211> LENGTH: 2537
<212> TYPE: PRT
<213> ORGANISM: Homo sapiens

<400> SEQUENCE: 4

```
Met Glu Asp Phe Arg Gly Ile Ala Glu Glu Ser Phe Pro Ser Phe Leu
1               5                   10                  15

Thr Asn Ser Leu Phe Gly Asn Ser Gly Ile Leu Glu Asn Val Thr Leu
            20                  25                  30

Ser Ser Asn Leu Gly Leu Pro Val Ala Val Ser Thr Leu Ala Arg Asp
        35                  40                  45

Arg Ser Ser Thr Asp Asn Arg Tyr Pro Asp Ile Gln Ala Ser Tyr Leu
    50                  55                  60
```

```
Val Glu Gly Arg Phe Ser Val Pro Ser Gly Ser Pro Gly Ser Gln
 65                  70                  75                  80

Ser Asp Ala Glu Pro Arg Glu Arg Leu Gln Leu Ser Phe Gln Asp Asp
                 85                  90                  95

Asp Ser Ile Ser Arg Lys Lys Ser Tyr Val Glu Ser Gln Arg Leu Ser
            100                 105                 110

Asn Ala Leu Ser Lys Gln Ser Ala Leu Gln Met Glu Thr Ala Gly Pro
        115                 120                 125

Glu Glu Glu Pro Ala Gly Ala Thr Glu Ser Leu Gln Gly Gln Asp Leu
    130                 135                 140

Phe Asn Arg Ala Ser Pro Leu Glu Gln Ala Gln Asp Ser Pro Ile Asp
145                 150                 155                 160

Phe His Leu Gln Ser Trp Met Asn Asn Lys Glu Pro Lys Ile Val Val
                165                 170                 175

Leu Asp Ala Gly Lys His Phe Glu Asp Lys Thr Leu Lys Ser Asp Leu
            180                 185                 190

Ser His Thr Ser Leu Leu Glu Asn Glu Lys Leu Ile Leu Pro Thr Ser
        195                 200                 205

Leu Glu Asp Ser Ser Asp Asp Ile Asp Asp Glu Met Phe Tyr Asp
    210                 215                 220

Asp His Leu Glu Ala Tyr Phe Glu Gln Leu Ala Ile Pro Gly Met Ile
225                 230                 235                 240

Tyr Glu Asp Leu Glu Gly Pro Glu Pro Glu Lys Gly Phe Lys Leu
                245                 250                 255

Pro Thr Asn Gly Leu Arg Gln Ala Asn Glu Asn Gly Ser Leu Asn Cys
                260                 265                 270

Lys Phe Gln Ser Glu Asn Asn Ser Ser Leu Ile Ser Leu Asp Ser His
            275                 280                 285

Ser Ser Glu Thr Thr His Lys Glu Ser Glu Glu Ser Gln Val Ile Cys
        290                 295                 300

Leu Pro Gly Thr Ser Asn Ser Ile Gly Thr Gly Asp Ser Arg Arg Tyr
305                 310                 315                 320

Thr Asp Gly Met Leu Pro Phe Ser Ser Gly Thr Trp Gly Thr Glu Lys
                325                 330                 335

Glu Ile Glu Asn Leu Lys Gly Ile Val Pro Asp Leu Asn Ser Glu Cys
            340                 345                 350

Ala Ser Lys Asp Val Leu Val Lys Thr Leu Arg Ala Ile Asp Val Lys
        355                 360                 365

Leu Asn Ser Asp Asn Phe His Asp Ala Asn Ala Asn Arg Gly Gly Phe
    370                 375                 380

Asp Leu Thr Asp Pro Val Lys Gln Gly Ala Glu Cys Pro His Gln Asn
385                 390                 395                 400

Lys Thr Val Leu His Met Asp Gly Cys Leu Asp Thr Glu Thr Pro Thr
                405                 410                 415

Val Ser Ile Gln Glu Asn Val Asp Val Ala Ser Leu Lys Pro Ile Ser
            420                 425                 430

Asp Ser Gly Ile Asn Phe Thr Asp Ala Ile Trp Ser Pro Thr Cys Glu
        435                 440                 445

Arg Arg Thr Cys Glu Cys His Glu Ser Ile Glu Lys Asn Lys Asp Lys
    450                 455                 460

Thr Asp Leu Pro Gln Ser Val Val Tyr Gln Asn Glu Glu Gly Arg Trp
465                 470                 475                 480

Val Thr Asp Leu Ala Tyr Tyr Thr Ser Phe Asn Ser Lys Gln Asn Leu
```

-continued

```
            485                 490                 495
Asn Val Ser Leu Ser Asp Glu Met Asn Glu Asp Phe Arg Ser Gly Ser
            500                 505                 510

Glu Ala Phe Asp Leu Ile Ala Gln Asp Glu Glu Phe Asn Lys Glu
            515                 520             525

His Gln Phe Ile Gln Glu Glu Asn Ile Asp Ala His Asn Thr Ser Val
            530                 535                 540

Ala Leu Gly Asp Thr Ser Trp Gly Ala Thr Ile Asn Tyr Ser Leu Leu
545                 550                 555                 560

Arg Lys Ser Arg Ser Thr Ser Asp Leu Asp Lys Asp Ala Ser Tyr
                565                 570                 575

Leu Arg Leu Ser Leu Gly Glu Phe Phe Ala Gln Arg Ser Glu Ala Leu
            580                 585                 590

Gly Cys Leu Gly Gly Asn Asn Val Lys Arg Pro Ser Phe Gly Tyr
            595                 600             605

Phe Ile Arg Ser Pro Glu Lys Arg Glu Pro Ile Ala Leu Ile Arg Lys
Ile         610                 615                 620

Ser Asp Val Ser Arg Gly Asn Leu Glu Lys Glu Met Ala His Leu Asn
625                 630                 635                 640

His Asp Leu Tyr Ser Gly Asp Leu Asn Glu Gln Ser Gln Ala Gln Leu
                645                 650                 655

Ser Glu Gly Ser Ile Thr Leu Gln Val Glu Ala Val Glu Ser Thr Ser
            660                 665                 670

Gln Val Asp Glu Asn Asp Val Thr Leu Thr Ala Asp Lys Gly Lys Thr
            675                 680                 685

Glu Asp Thr Phe Phe Met Ser Asn Lys Pro Gln Arg Tyr Lys Asp Lys
            690                 695                 700

Leu Pro Asp Ser Gly Asp Ser Met Leu Arg Ile Ser Thr Ile Ala Ser
705                 710                 715                 720

Ala Ile Ala Glu Ala Ser Val Asn Thr Asp Pro Ser Gln Leu Ala Ala
                725                 730                 735

Met Ile Lys Ala Leu Ser Asn Lys Thr Arg Asp Lys Thr Phe Gln Glu
            740                 745                 750

Asp Glu Lys Gln Lys Asp Tyr Ser His Val Arg His Phe Leu Pro Asn
            755                 760             765

Asp Leu Glu Lys Ser Asn Gly Ser Asn Ala Leu Asp Met Glu Lys Tyr
            770                 775                 780

Leu Lys Lys Thr Glu Val Ser Arg Tyr Glu Ser Ala Leu Glu Asn Phe
785                 790                 795                 800

Ser Arg Ala Ser Met Ser Asp Thr Trp Asp Leu Ser Leu Pro Lys Glu
                805                 810                 815

Gln Thr Thr Gln Asp Ile His Pro Val Asp Leu Ser Ala Thr Ser Val
            820                 825                 830

Ser Val Arg Ala Pro Glu Glu Asn Thr Ala Ala Ile Val Tyr Val Glu
            835                 840             845

Asn Gly Glu Ser Glu Asn Gln Glu Ser Phe Arg Thr Ile Asn Ser Ser
            850                 855                 860

Asn Ser Val Thr Asn Arg Glu Asn Asn Ser Ala Val Val Asp Val Lys
865                 870                 875                 880

Thr Cys Ser Ile Asp Asn Lys Leu Gln Asp Val Gly Asn Asp Glu Lys
                885                 890                 895

Ala Thr Ser Ile Ser Thr Pro Ser Asp Ser Tyr Ser Ser Val Arg Asn
            900                 905                 910
```

```
Pro Arg Ile Thr Ser Leu Cys Leu Leu Lys Asp Cys Glu Glu Ile Arg
        915                 920                 925

Asp Asn Arg Glu Asn Gln Arg Gln Asn Glu Cys Val Ser Glu Ile Ser
    930                 935                 940

Asn Ser Glu Lys His Val Thr Phe Glu Asn His Arg Ile Val Ser Pro
945                 950                 955                 960

Lys Asn Ser Asp Leu Lys Asn Thr Ser Pro Glu His Gly Gly Arg Gly
                965                 970                 975

Ser Glu Asp Glu Gln Glu Ser Phe Arg Pro Ser Thr Ser Pro Leu Ser
            980                 985                 990

His Ser Ser Pro Ser Glu Ile Ser  Gly Thr Ser Ser  Gly Cys Ala
        995                 1000                1005

Leu Glu  Ser Phe Gly Ser Ala  Ala Gln Gln Gln  Pro Pro Cys
    1010                1015                1020

Glu Gln  Glu Leu Ser Pro Leu  Val Cys Ser Pro  Ala Gly Val Ser
    1025                1030                1035

Arg Leu  Thr Tyr Val Ser Glu  Pro Glu Ser Ser Tyr  Pro Thr Thr
    1040                1045                1050

Ala Thr  Asp Asp Ala Leu Glu  Asp Arg Lys Ser Asp  Ile Thr Ser
    1055                1060                1065

Glu Leu  Ser Thr Thr Ile Ile  Gln Gly Ser Pro Ala  Ala Leu Glu
    1070                1075                1080

Glu Arg  Ala Met Glu Lys Leu  Arg Glu Lys Val Pro  Phe Gln Asn
    1085                1090                1095

Arg Gly  Lys Gly Thr Leu Ser  Ser Ile Ile Gln Asn  Asn Ser Asp
    1100                1105                1110

Thr Arg  Lys Ala Thr Glu Thr  Thr Ser Leu Ser Ser  Lys Pro Glu
    1115                1120                1125

Tyr Val  Lys Pro Asp Phe Arg  Trp Ser Lys Asp Pro  Ser Ser Lys
    1130                1135                1140

Ser Gly  Asn Leu Leu Glu Thr  Ser Glu Val Gly Trp  Thr Ser Asn
    1145                1150                1155

Pro Glu  Glu Leu Asp Pro Ile  Arg Leu Ala Leu Leu  Gly Lys Ser
    1160                1165                1170

Gly Leu  Ser Cys Gln Val Gly  Ser Ala Thr Ser His  Pro Val Ser
    1175                1180                1185

Cys Gln  Glu Pro Ile Asp Glu  Asp Gln Arg Ile Ser  Pro Lys Asp
    1190                1195                1200

Lys Ser  Thr Ala Gly Arg Glu  Phe Ser Gly Gln Val  Ser His Gln
    1205                1210                1215

Thr Thr  Ser Glu Asn Gln Cys  Thr Pro Ile Pro Ser  Ser Thr Val
    1220                1225                1230

His Ser  Ser Val Ala Asp Met  Gln Asn Met Pro Ala  Ala Val His
    1235                1240                1245

Ala Leu  Leu Thr Gln Pro Ser  Leu Ser Ala Ala Pro  Phe Ala Gln
    1250                1255                1260

Arg Tyr  Leu Gly Thr Leu Pro  Ser Thr Gly Ser Thr  Thr Leu Pro
    1265                1270                1275

Gln Cys  His Ala Gly Asn Ala  Thr Val Cys Gly Phe  Ser Gly Gly
    1280                1285                1290

Leu Pro  Tyr Pro Ala Val Ala  Gly Glu Pro Val Gln  Asn Ser Val
    1295                1300                1305
```

-continued

Ala Val Gly Ile Cys Leu Gly Ser Asn Ile Gly Ser Gly Trp Met
1310                1315                1320

Gly Thr Ser Ser Leu Cys Asn Pro Tyr Ser Asn Thr Leu Asn Gln
1325                1330                1335

Asn Leu Leu Ser Thr Thr Lys Pro Phe Pro Val Pro Ser Val Gly
1340                1345                1350

Thr Asn Cys Gly Ile Glu Pro Trp Asp Ser Gly Val Thr Ser Gly
1355                1360                1365

Leu Gly Ser Val Arg Val Pro Glu Glu Leu Lys Leu Pro His Ala
1370                1375                1380

Cys Cys Val Gly Ile Ala Ser Gln Thr Leu Leu Ser Val Leu Asn
1385                1390                1395

Pro Thr Asp Arg Trp Leu Gln Val Ser Ile Gly Val Leu Ser Ile
1400                1405                1410

Ser Val Asn Gly Glu Lys Val Asp Leu Ser Thr Tyr Arg Cys Leu
1415                1420                1425

Val Phe Lys Asn Lys Ala Ile Ile Arg Pro His Ala Thr Glu Glu
1430                1435                1440

Ile Lys Val Leu Phe Ile Pro Ser Ser Pro Gly Val Phe Arg Cys
1445                1450                1455

Thr Phe Ser Val Ala Ser Trp Pro Cys Ser Thr Asp Ala Glu Thr
1460                1465                1470

Ile Val Gln Ala Glu Ala Leu Ala Ser Thr Val Thr Leu Thr Ala
1475                1480                1485

Ile Ala Glu Ser Pro Val Ile Glu Val Glu Thr Glu Lys Lys Asp
1490                1495                1500

Val Leu Asp Phe Gly Asp Leu Thr Tyr Gly Gly Trp Lys Ala Leu
1505                1510                1515

Pro Leu Lys Leu Ile Asn Arg Thr His Ala Thr Val Pro Ile Arg
1520                1525                1530

Leu Ile Ile Asn Ala Asn Ala Val Ala Trp Arg Cys Phe Thr Phe
1535                1540                1545

Ser Lys Glu Ser Val Arg Ala Pro Val Glu Val Ala Pro Cys Ala
1550                1555                1560

Asp Val Val Thr Arg Leu Ala Gly Pro Ser Val Val Asn His Met
1565                1570                1575

Met Pro Ala Ser Tyr Asp Gly Gln Asp Pro Glu Phe Leu Met Ile
1580                1585                1590

Trp Val Leu Phe His Ser Pro Lys Lys Gln Ile Ser Ser Ser Asp
1595                1600                1605

Ile Leu Asp Ser Ala Glu Glu Phe Ser Ala Lys Val Asp Ile Glu
1610                1615                1620

Val Asp Ser Pro Asn Pro Thr Pro Val Leu Arg Ser Val Ser Leu
1625                1630                1635

Arg Ala Arg Ala Gly Ile Ala Arg Ile His Ala Pro Arg Asp Leu
1640                1645                1650

Gln Thr Met His Phe Leu Ala Lys Val Ala Ser Ser Arg Lys Gln
1655                1660                1665

His Leu Pro Leu Lys Asn Ala Gly Asn Ile Glu Val Tyr Leu Asp
1670                1675                1680

Ile Lys Val Pro Glu Gln Gly Ser His Phe Ser Val Asp Pro Lys
1685                1690                1695

Asn Leu Leu Leu Lys Pro Gly Glu Glu His Glu Val Ile Val Ser

```
                    1700                1705                1710

Phe Thr Pro Lys Asp Pro Glu Ala Cys Glu Arg Ile Leu Lys
    1715                1720                1725

Ile Phe Val Gln Pro Phe Gly Pro Gln Tyr Glu Val Val Leu Lys
    1730                1735                1740

Gly Glu Val Ile Ser Ser Gly Ser Lys Pro Leu Ser Pro Gly Pro
    1745                1750                1755

Cys Leu Asp Ile Pro Ser Ile Leu Ser Asn Lys Gln Phe Leu Ala
    1760                1765                1770

Trp Gly Gly Val Pro Leu Gly Arg Thr Gln Leu Gln Lys Leu Ala
    1775                1780                1785

Leu Arg Asn Asn Ser Ala Ser Thr Thr Gln His Leu Arg Leu Leu
    1790                1795                1800

Ile Arg Gly Gln Asp Gln Asp Cys Phe Gln Leu Gln Asn Thr Phe
    1805                1810                1815

Gly Ser Glu Gln Arg Leu Thr Ser Asn Cys Glu Ile Arg Ile His
    1820                1825                1830

Pro Lys Glu Asp Ile Phe Ile Ser Val Leu Phe Ala Pro Thr Arg
    1835                1840                1845

Leu Ser Cys Met Leu Ala Arg Leu Glu Ile Lys Gln Leu Gly Asn
    1850                1855                1860

Arg Ser Gln Pro Gly Ile Lys Phe Thr Ile Pro Leu Ser Gly Tyr
    1865                1870                1875

Gly Gly Thr Ser Asn Leu Ile Leu Glu Gly Val Lys Lys Leu Ser
    1880                1885                1890

Asp Ser Tyr Met Val Thr Val Asn Gly Leu Val Pro Gly Lys Glu
    1895                1900                1905

Ser Lys Ile Val Phe Ser Val Arg Asn Thr Gly Ser Arg Ala Ala
    1910                1915                1920

Phe Val Lys Ala Val Gly Phe Lys Asp Ser Gln Lys Lys Val Leu
    1925                1930                1935

Leu Asp Pro Lys Val Leu Arg Ile Phe Pro Asp Lys Phe Val Leu
    1940                1945                1950

Lys Glu Arg Thr Gln Glu Asn Val Thr Leu Ile Tyr Asn Pro Ser
    1955                1960                1965

Asp Arg Gly Ile Asn Asn Lys Thr Ala Thr Glu Leu Ser Thr Val
    1970                1975                1980

Tyr Leu Phe Gly Gly Asp Glu Ile Ser Arg Gln Gln Tyr Arg Arg
    1985                1990                1995

Ala Leu Leu His Lys Pro Glu Met Ile Lys Gln Ile Leu Pro Glu
    2000                2005                2010

His Ser Val Leu Gln Asn Ile Asn Phe Val Glu Ala Phe Gln Asp
    2015                2020                2025

Glu Leu Leu Val Thr Glu Val Tyr Asp Leu Pro Gln Arg Pro Asn
    2030                2035                2040

Asp Val Gln Leu Phe Tyr Gly Ser Met Cys Lys Ile Ile Leu Ser
    2045                2050                2055

Val Ile Gly Glu Phe Arg Asp Cys Ile Ser Ser Arg Glu Phe Leu
    2060                2065                2070

Gln Pro Ser Ser Lys Ala Ser Leu Glu Ser Thr Ser Asp Leu Gly
    2075                2080                2085

Ala Ser Gly Lys His Gly Gly Asn Val Ser Leu Asp Val Leu Pro
    2090                2095                2100
```

```
Val Lys Gly Pro Gln Gly Ser Pro Leu Leu Ser Arg Ala Ala Arg
    2105            2110                2115

Pro Pro Leu Asp Gln Leu Ala Ser Glu Glu Pro Trp Thr Val Leu
    2120            2125                2130

Pro Glu His Leu Ile Leu Val Ala Pro Ser Pro Cys Asp Met Ala
    2135            2140                2145

Lys Thr Gly Arg Phe Gln Ile Val Asn Asn Ser Val Arg Leu Leu
    2150            2155                2160

Arg Phe Glu Leu Cys Trp Pro Ala His Cys Leu Thr Val Thr Pro
    2165            2170                2175

Gln His Gly Cys Val Ala Pro Glu Ser Lys Leu Gln Ile Leu Val
    2180            2185                2190

Ser Pro Asn Ser Ser Leu Ser Thr Lys Gln Ser Met Phe Pro Trp
    2195            2200                2205

Ser Gly Leu Ile Tyr Ile His Cys Asp Asp Gly Gln Lys Lys Ile
    2210            2215                2220

Val Lys Val Gln Ile Arg Glu Asp Leu Thr Gln Val Glu Leu Leu
    2225            2230                2235

Thr Arg Leu Thr Ser Lys Pro Phe Gly Ile Leu Ser Pro Val Ser
    2240            2245                2250

Glu Pro Ser Val Ser His Leu Val Lys Pro Met Thr Lys Pro Pro
    2255            2260                2265

Ser Thr Lys Val Glu Ile Arg Asn Lys Ser Ile Thr Phe Pro Thr
    2270            2275                2280

Thr Glu Pro Gly Glu Thr Ser Glu Ser Cys Leu Glu Leu Glu Asn
    2285            2290                2295

His Gly Thr Thr Asp Val Lys Trp His Leu Ser Ser Leu Ala Pro
    2300            2305                2310

Pro Tyr Val Lys Gly Val Asp Glu Ser Gly Asp Val Phe Arg Ala
    2315            2320                2325

Thr Tyr Ala Ala Phe Arg Cys Ser Pro Ile Ser Gly Leu Leu Glu
    2330            2335                2340

Ser His Gly Ile Gln Lys Val Ser Ile Thr Phe Leu Pro Arg Gly
    2345            2350                2355

Arg Gly Asp Tyr Ala Gln Phe Trp Asp Val Glu Cys His Pro Leu
    2360            2365                2370

Lys Glu Pro His Met Lys His Thr Leu Arg Phe Gln Leu Ser Gly
    2375            2380                2385

Gln Ser Ile Glu Ala Glu Asn Glu Pro Glu Asn Ala Cys Leu Ser
    2390            2395                2400

Thr Asp Ser Leu Ile Lys Ile Asp His Leu Val Lys Pro Arg Arg
    2405            2410                2415

Gln Ala Val Ser Glu Ala Ser Ala Arg Ile Pro Glu Gln Leu Asp
    2420            2425                2430

Val Thr Ala Arg Gly Val Tyr Ala Pro Glu Asp Val Tyr Arg Phe
    2435            2440                2445

Arg Pro Thr Ser Val Gly Glu Ser Arg Thr Leu Lys Val Asn Leu
    2450            2455                2460

Arg Asn Asn Ser Phe Ile Thr His Ser Leu Lys Phe Leu Ser Pro
    2465            2470                2475

Arg Glu Pro Phe Tyr Val Lys His Ser Lys Tyr Ser Leu Arg Ala
    2480            2485                2490
```

```
Gln His Tyr Ile Asn Met Pro Val Gln Phe Lys Pro Lys Ser Ala
    2495                2500                2505

Gly Lys Phe Glu Ala Leu Leu Val Ile Gln Thr Asp Glu Gly Lys
    2510                2515                2520

Ser Ile Ala Ile Arg Leu Ile Gly Glu Ala Leu Gly Lys Asn
    2525                2530                2535

<210> SEQ ID NO 5
<211> LENGTH: 25
<212> TYPE: RNA
<213> ORGANISM: Homo sapiens

<400> SEQUENCE: 5
ggaaguaagc ucaggaucuc agcag                                              25

<210> SEQ ID NO 6
<211> LENGTH: 27
<212> TYPE: RNA
<213> ORGANISM: Homo sapiens

<400> SEQUENCE: 6
guccuucauu cgaguccuau agucguc                                            27

<210> SEQ ID NO 7
<211> LENGTH: 19
<212> TYPE: RNA
<213> ORGANISM: Homo sapiens

<400> SEQUENCE: 7
cacaugaugc cugcuaguu                                                     19

<210> SEQ ID NO 8
<211> LENGTH: 19
<212> TYPE: RNA
<213> ORGANISM: Homo sapiens

<400> SEQUENCE: 8
cacaugaugc cugcuaguu                                                     19

<210> SEQ ID NO 9
<211> LENGTH: 19
<212> TYPE: RNA
<213> ORGANISM: Homo sapiens

<400> SEQUENCE: 9
ggacuuaagu gcuacuagu                                                     19
```

METHODS AND COMPOSITIONS TO INHIBIT METASTASIS AND TO TREAT FIBROSIS AND TO ENHANCE WOUND HEALING

CROSS-REFERENCE TO RELATED APPLICATIONS

The application is a divisional of U.S. application Ser. No. 15/023,869, filed Mar. 22, 2016, now allowed, U.S. national stage entry under 35 U.S.C. § 371 of PCT International Patent Application No. PCT/US2014/055393, filed Sep. 12, 2014, which claims benefit of U.S. Provisional Application No. 61/885,676, filed Oct. 2, 2013, the contents of each of which are incorporated herein by reference into the subject application.

STATEMENT OF GOVERNMENT SUPPORT

This invention was made with government support under grant number W81XWH1210379 awarded by the Telemedicine and Advanced Technology Research Center (TATRC) at the U.S. Army Medical Research and Materiel Command (USAMRMC). The government has certain rights in the invention.

BACKGROUND OF THE INVENTION

The disclosures of all publications, patents, patent application publications and books referred to in this application are hereby incorporated by reference in their entirety into the subject application to more fully describe the art to which the subject invention pertains.

Cancer metastasis is stimulated by the movement of cancer cells from the primary tumor to other tissues or organs. Metastatic cancer is responsible for the majority of cancer deaths. There are currently no effective means of treating metastasis, so the development of agents that inhibit the ability of cancer cells to move along their substrata for treating or inhibiting metastasis would represent a major advance.

Fibrosis is the formation of excess fibrous connective tissue in an organ or tissue in a reparative or reactive process. This results from the hyperproliferation and motility of cells, such as fibroblasts, that lay down connective tissue. Fibrosis can be a reactive, benign, or pathological state. In response to injury this is called scarring and if fibrosis arises from a single cell line this is called a fibroma. Physiologically this acts to deposit connective tissue, which can obliterate the architecture and function of the underlying organ or tissue. Fibrosis can be used to describe the pathological state of excess deposition of fibrous tissue, as well as the process of connective tissue deposition in healing. Fibrosis is similar to metastasis in that there are currently few therapeutic treatment strategies. The development of agents that prevent cell motility into wounded tissue would represent an important advance. Related to this, the development of safe and effective therapies for treating acute and chronic wounds is also of great interest. Wound healing is an intricate, multi-stage process that relies heavily on the delivery of new cells to the wound zone. Two key elements of the wound healing response are fibroplasia and epithelialization when fibroblasts and epithelial cells, respectively, enter the wound to form a protective barrier from the external environment. This is stimulated by cell proliferation and migration from the wound edge. The identification of agents that increase the rate at which cells invade and close a wound would represent a major advance in wound healing therapeutics. Ideally, this would be a topically applied agent that stimulates the proliferation and migration of fibroblasts and wound edge epithelial cells.

The present invention addresses this need and identifies novel targets in treating and preventing metastasis, treating and preventing fibrosis, and treating and preventing pain associated with wound healing.

SUMMARY OF THE INVENTION

A method of treating metastasis or inhibiting metastasis in a subject having a cancer is provided comprising administering to the subject an amount of an inhibitor of KIF19 or of Kif19 gene product effective to treat metastasis or inhibit metastasis.

Also provided is a method of treating metastasis or inhibiting metastasis in a subject having a cancer comprising administering to the subject an amount of an inhibitor of CEP192 or of Cep192 gene product effective to treat metastasis or inhibit metastasis.

Also provided is a method of treating fibrosis or scarring, or of inhibiting fibrosis or scarring, in a subject in need thereof comprising administering to the subject an amount of an inhibitor of KIF19 or of Kif19 gene product effective to treat fibrosis or scarring, or inhibit fibrosis or scarring.

Also provided is a method of treating fibrosis or scarring, or inhibiting fibrosis or scarring, in a subject in need thereof comprising administering to the subject an amount of an inhibitor of Cep192 effective to treat fibrosis or scarring, or inhibit fibrosis or scarring.

Also provided is a method of treating pain associated with wound healing in a subject having a wound comprising administering to the subject an amount of an inhibitor of Cep192 effective to treat pain associated with wound healing.

Also provided is an inhibitor of KIF19, or of Kif19 gene product is provided for treating metastasis or inhibiting metastasis in a subject having a cancer.

Also provided is an inhibitor of CEP192 or of Cep192 gene product is provided for treating metastasis or inhibiting metastasis in a subject having a cancer.

Also provided is an inhibitor of KIF19, or of Kif19 gene product, is provided for treating fibrosis or scarring in a subject in need thereof.

Also provided is an inhibitor of CEP192 or of Cep192 gene product, is provided for treating fibrosis or scarring in a subject in need thereof.

Also provided is an inhibitor of CEP192 or of Cep192 gene product, for treating pain associated with wound healing in a subject.

DETAILED DESCRIPTION OF THE INVENTION

Figure 1:
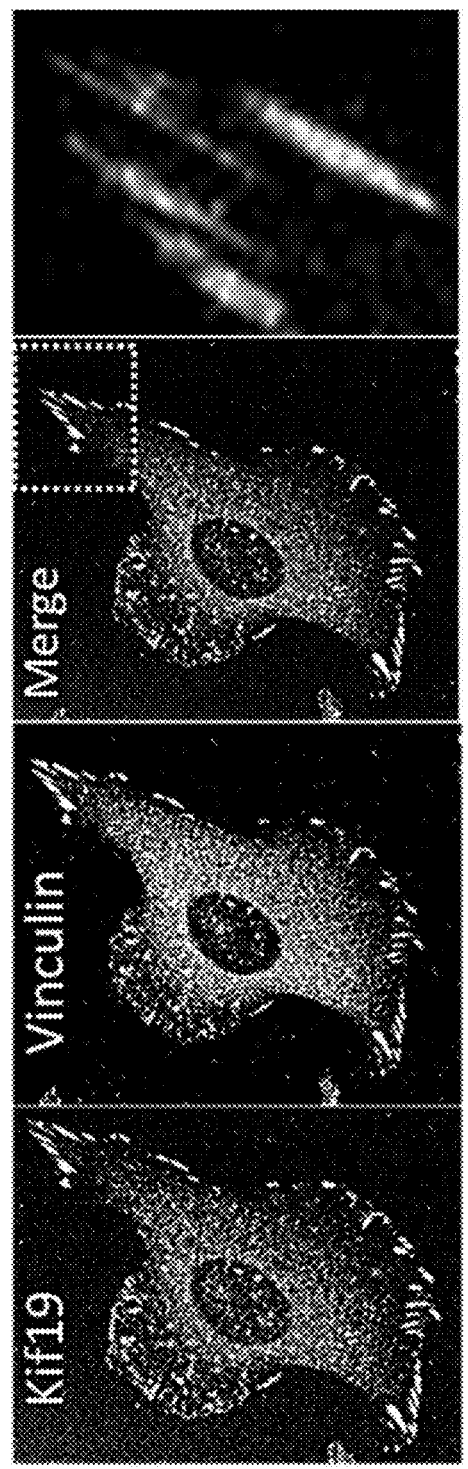
FIG. 1: A confocal micrograph showing a human U2OS cell double-labeled for Kif19 and the FA protein, vinculin. The far right panel is a higher magnification of the region boxed in "merge".

A method of treating metastasis or inhibiting metastasis in a subject having a cancer is provided comprising administering to the subject an amount of an inhibitor of KIF19 or of Kif19 gene product effective to treat metastasis or inhibit metastasis.

As used herein, "treating" metastasis means ameliorating or lessening or reducing further progression of an extant metastasis. As used herein, "inhibiting" metastasis means lessening the extent of, development of, or progression of a new metastasis.

In embodiments of the invention described herein where both treating and inhibiting a condition are recited, the individual embodiments of treating and inhibiting are also encompassed separately. Thus, methods of treating are provided. And methods of inhibiting are also separately provided.

In an embodiment, the preferred subject is a human subject.

In embodiments of the invention described herein, the preferred subject is a human subject.

Also provided is a method of treating metastasis or inhibiting metastasis in a subject having a cancer comprising administering to the subject an amount of an inhibitor of CEP192 or of Cep192 gene product effective to treat metastasis or inhibit metastasis.

Also provided is a method of treating fibrosis or scarring, or of inhibiting fibrosis or scarring, in a subject in need thereof comprising administering to the subject an amount of an inhibitor of KIF19 or of Kif19 gene product effective to treat fibrosis or scarring, or inhibit fibrosis or scarring. As used herein, "treating" a fibrosis means ameliorating or lessening or reducing further progression of an extant fibrosis. As used herein, "inhibiting" fibrosis means lessening the extent of, development of, or progression of a fibrosis. As used herein, "treating" scarring means ameliorating or lessening or reducing further progression of an extant scarring or scarring process. As used herein, "inhibiting" scarring means lessening the extent of, development of, or progression of a scarring or scarring process.

As used herein, any recitation of embodiments in the alternative, e.g. embodiment A or embodiment B, includes the specific, separate embodiments of (i) embodiment A and (ii) of embodiment B, as part of the invention.

Also provided is a method of treating fibrosis or scarring, or inhibiting fibrosis or scarring, in a subject in need thereof comprising administering to the subject an amount of an inhibitor of CEP192 or of an inhibitor of Cep192 gene product effective to treat fibrosis or scarring, or inhibit fibrosis or scarring.

Also provided is a method of treating pain associated with wound healing in a subject having a wound comprising administering to the subject an amount of an inhibitor of CEP192 or of an inhibitor of Cep192 gene product effective to treat pain associated with wound healing. As used herein, "treating" pain associated with wound healing means ameliorating or lessening or reducing pain associated with an extant wound.

In an embodiment of the methods, the KIF19 or Kif19 gene product is a human KIF19 or human Kif19 gene product, respectively.

In an embodiment of the methods, the CEP192 or Cep192 gene product is a human CEP192 or a human Cep192 gene product, respectively.

In an embodiment of the methods, the inhibitor of KIF19 is an RNAi nucleic acid. In an embodiment of the methods, the inhibitor of CEP192 is an RNAi nucleic acid. In an embodiment of the methods, the RNAi nucleic acid is a siRNA directed to KIF19 or a shRNA directed to KIF19. In an embodiment of the methods, the RNAi nucleic acid is a siRNA directed to CEP192 or a shRNA directed to CEP192. In an embodiment of the methods, the siRNA is administered. In an embodiment of the methods, the shRNA is administered. In an embodiment of the methods, the siRNA is administered as a composition comprising the siRNA associated with a nanoparticle. In an embodiment of the methods, the siRNA is administered as a composition comprising the siRNA encapsulated with a nanoparticle. In an embodiment of the methods, the nanoparticle is PEGylated. In an embodiment of the methods, the siRNA is administered as a viral vector. In an embodiment of the methods, the shRNA is administered as a viral vector.

In an embodiment of the methods, the cancer is a thyroid, blood, bladder, breast, colorectal, kidney, lung, melanoma, ovary, pancreas, prostate or stomach cancer. In an embodiment of the methods, the cancer is an anaplastic thyroid carcinoma. In an embodiment of the methods, the cancer is large cell lung cancer.

In an embodiment of the methods, the fibrosis is in response to an injury. In an embodiment of the methods, the fibrosis is a fibroma, pulmonary fibrosis, cystic fibrosis, hepatic cirrhosis, endomyocardial fibrosis, from a previous myocardial infarction, atrial fibrosis, mediastinal fibrosis, myelofibrosis, retroperitoneal fibrosis, progressive massive fibrosis of the lungs, a complication of pneumoconiosis, nephrogenic systemic fibrosis, Crohn's disease fibrosis, keloid fibrosis, scleroderma/systemic sclerosis of skin or lungs, arthrofibrosis or adhesive capsulitis fibrosis.

In an embodiment of the methods, the scarring is skin scarring, cardiovascular scarring, cardiac tissue scarring, or neuronal scarring.

In an embodiment of the methods, the wound is a skin wound, cardiovascular wound, a cardiac tissue wound, or neuronal wound. In an embodiment of the methods, the skin wound is a burn wound.

In an embodiment of the methods regarding wounds, scarring or treating pain associated with the wound, the inhibitor may be applied directly to the wound of the subject.

In an embodiment of the methods regarding skin wounds, scarring or treating pain associated with the skin wound, the inhibitor may be applied to the skin of the subject.

Also provided is a method of identifying an anti-metastatic agent comprising contacting a nucleic acid encoding Kif19 gene product with the agent or contacting Kif19 gene product with the agent and determining if the agent inhibits expression of the nucleic acid-encoded Kif19 gene product or inhibits activity of the Kif19 gene product, respectively, and subsequently identifying the agent as an anti-metastatic agent or not, wherein an agent that inhibits Kif19 expression or Kif19 gene product is identified as an anti-metastatic agent.

Preferably, an "agent" in the methods of identifying an anti-metastatic agent, anti-fibrotic agent, or pain-relieving agent, is a small organic molecule of 1,500 daltons or less, a peptide, a protein, an antibody, a fragment of an antibody, a carbohydrate, an oligonucleotide or a nucleic acid. In an embodiment of the methods of identifying an agent as set forth herein, the agent is a small organic molecule, a peptide, a nucleic acid, an oligonucleotide, an antibody, an antigen-binding fragment of an antibody or an aptamer.

Also provided is a method of identifying an anti-metastatic agent comprising contacting a nucleic acid encoding Cep192 gene product with the agent or contacting Cep192 gene product with the agent and determining if the agent inhibits expression of the nucleic acid-encoded Cep192 gene product or inhibits activity of the Cep192 gene product, respectively, and subsequently identifying the agent as an anti-metastatic agent or not, wherein an agent that inhibits Cep192 expression or Cep192 gene product is identified as an anti-metastatic agent.

Also provided is a method of identifying an anti-fibrotic agent comprising contacting a nucleic acid encoding Kif19 gene product with the agent or contacting Kif19 gene product with the agent and determining if the agent inhibits expression of the nucleic acid-encoded Kif19 gene product or inhibits activity of the Kif19 gene product, respectively, and subsequently identifying the agent as an anti-fibrotic agent or not, wherein an agent that inhibits Kif19 expression or Kif19 gene product is identified as an anti-fibrotic agent.

Also provided is a method of identifying an anti-fibrotic agent comprising contacting a nucleic acid encoding Cep192 gene product with the agent or contacting Cep192 gene product with the agent and determining if the agent inhibits expression of the nucleic acid-encoded Cep192 gene product or inhibits activity of the Cep192 gene product, respectively, and subsequently identifying the agent as an anti-fibrotic agent or not, wherein an agent that inhibits Cep192 expression or Cep192 gene product is identified as an anti-fibrotic agent.

Also provided is a method of identifying a pain-relieving agent comprising contacting a nucleic acid encoding Cep192 gene product with the agent or contacting Cep192 gene product with the agent and determining if the agent inhibits expression of the nucleic acid-encoded Cep192 gene product or inhibits activity of the Cep192 gene product, respectively, and subsequently identifying the agent as a pain-relieving agent or not, wherein an agent that inhibits Cep192 expression or Cep192 gene product is identified as a pain-relieving agent.

Generally herein, with regard to KIF19 and Kif19, "KIF19" (i.e. upper case) refers to the gene and "Kif19" (i.e. lower case) refers to the protein. The protein may also be referred to as "Kif19 gene product." Generally herein, with regard to CEP192 and Cep192, "CEP192" (i.e. upper case) refers to the gene and "Cep192" (i.e. lower case) refers to the protein. The protein may also be referred to as "Cep192 gene product." As used herein, a transcript of a given gene means any nucleic acid, for example an mRNA, that encodes the protein gene product encoded by the gene. Thus, a transcript of CEP192 includes an mRNA encoding CEP192 gene product. Thus, a transcript of KIF19 includes an mRNA encoding KIF19 gene product.

A pharmaceutical composition is provided comprising an amount of an inhibitor of KIF19 or of Kif19 gene product. In an embodiment, the pharmaceutical composition comprises an amount of an inhibitor of KIF19 or of Kif19 gene product effective to treat a wound in a human subject, or comprises an amount of an inhibitor of KIF19 or of Kif19 gene product effective to treat or inhibit metastasis in a subject, or comprises an amount of an inhibitor of KIF19 or of Kif19 gene product effective to treat or inhibit fibrosis in a subject. In an embodiment, the pharmaceutical composition comprises a pharmaceutically acceptable carrier. In an embodiment of the pharmaceutical composition, the inhibitor of KIF19 or of Kif19 gene product is encapsulated, completely or partially, by a nanoparticle. In an embodiment the nanoparticle comprises a hydrogel/sugar glass composite. In an embodiment, the nanoparticle is PEGylated. In an embodiment the nanoparticle is a liposomal nanoparticle. In an embodiment, the nanoparticle is paramagnetic. In an embodiment of the methods and compositions, the inhibitor is an siRNA which inhibits expression of Kif19 gene product. In an embodiment, the inhibitor is an shRNA which inhibits expression of Kif19 gene product.

The optimal dosage of the KIF19 inhibitor or of Kif19 gene product inhibitor administered in treatments herein will vary depending upon factors such as the pharmacodynamic characteristics of a specific inhibitor and its mode and route of administration; the age, sex, metabolic rate, absorptive efficiency, health and weight of the recipient; the nature and extent of the symptoms; the kind of concurrent treatment being administered; the frequency of treatment with the inhibitor and the desired therapeutic effect. A dosage unit of the KIF19 inhibitor or of Kif19 gene product inhibitor may comprise a single compound, or a mixture of the compound with one or more anti-infection compound(s) or wound healing-promoting compound(s); one or more anti-cancer compounds; or one or more anti-fibrotic compounds, as relevant to the condition being treated.

In an embodiment of the methods or compositions, inhibition is effected by RNAi. In an embodiment, RNAi inhibition of K1F19 or of Kif19 gene product expression is effected with an siRNA. The siRNA (small interfering RNA) with regard to KIF19/kif19 gene product as used in the methods or compositions described herein comprises a portion which is complementary to a nucleic acid sequence (in a non-limiting example an mRNA) encoding a Kif19 gene product. In an embodiment, the Kif19 gene product is a human Kif19 gene product. In an embodiment, the mRNA is or is encoded by NCBI Reference Sequence: NM_153209.3 (SEQ ID NO:1), and the siRNA is effective to inhibit expression of Kif19 gene product. In an embodiment, the mRNA is or is encoded by a known variant of the NCBI Reference Sequence: NM_153209.3 (SEQ ID NO:1), and the siRNA is effective to inhibit expression of Kif19 gene product. In an embodiment, the Kif19 gene product comprises consecutive amino acid residues having the sequence set forth in SEQ ID NO:2.

In an embodiment, the siRNA with regard to KIF19/kif19 gene product comprises a double-stranded portion (duplex). Tn an embodiment, the siRNA is 20-25 nucleotides in length. In an embodiment the siRNA comprises a 19-21 core RNA duplex with a one or two nucleotide 3' overhang on, independently, either one or both strands. The siRNA can be 5' phosphorylated, or not, and may be modified with any of the known modifications in the art to improve efficacy and/or resistance to nuclease degradation. In an embodiment, the siRNA is 5' phosphorylated. In an embodiment, the 5' terminal residue of a strand of the siRNA is phosphorylated. In an embodiment the 5' terminal residue of the antisense strand of the siRNA is phosphorylated. In one embodiment, a siRNA of the invention comprises a double-stranded RNA wherein one strand of the double-stranded RNA is 80%, 85%, 90%, 95% or 100% complementary to a portion of an RNA transcript of a KIF19 (gene) encoding Kif19 gene product. In an embodiment, the RNA transcript of a gene encoding Kif19 gene product is an mRNA. In an embodiment, the Kif19 gene product is a human Kif19 gene product.

In an embodiment, a siRNA of the invention comprises a double-stranded RNA wherein one strand of the RNA comprises a portion having a sequence the same as a portion of 18-25 consecutive nucleotides of an RNA transcript of a gene encoding Kif19 gene product. In an embodiment, the other strand is fully complementary to the one strand. In an embodiment, the Kif19 gene product is a human Kif19 gene product. In yet another embodiment, a siRNA of the invention comprises a double-stranded RNA wherein both strands of RNA are connected by a non-nucleotide linker. In yet another embodiment, a siRNA of the invention comprises a double-stranded RNA wherein the two strands of RNA are not connected other than by complementary hybridization. Alternately, a siRNA of the invention comprises a double-stranded RNA wherein both strands of RNA are connected by a nucleotide linker, such as a loop or stem loop structure. In an embodiment, one strand of the double-stranded siRNA is fully complementary to a nucleic acid encoding Kif19 gene product. In an embodiment, one strand of the double-stranded siRNA is fully complementary to a nucleic acid encoding Kif19 gene product except at one, or except at two, mismatched positions. In one embodiment, a single strand component of a siRNA of the invention is from 14 to 50 nucleotides in length. In another embodiment, a single strand component of a siRNA of the invention is 14, 15, 16, 17, 18, 19, 20, 21, 22, 23, 24, 25, 26, 27, or 28 nucleotides in length. In yet another embodiment, a single strand component of a siRNA of the invention is 18 nucleotides in length. In yet another embodiment, a single strand component of a siRNA of the invention is 19 nucleotides in length. In yet another embodiment, a single strand component of a siRNA of the invention is 20 nucleotides in length. In yet another embodiment, a single strand component of a siRNA of the invention is 21 nucleotides in length. In yet another embodiment, a single strand component of a siRNA of the invention is 22 nucleotides in length. In yet another embodiment, a single strand component of a siRNA of the invention is 23 nucleotides in length. In one embodiment, a siRNA of the invention is from 28 to 56 nucleotides in length. In another embodiment, a siRNA of the invention is 40, 41, 42, 43, 44, 45, 46, 47, 48, 49, 50, 51, or 52 nucleotides in length. In another embodiment, an siRNA of the invention comprises at least one 2'-sugar modification. In an embodiment, an siRNA of the invention comprises at least one nucleic acid base modification. In an embodiment, an siRNA of the invention comprises at least one phosphate backbone modification. As used herein, "at least one" means one or more. In an embodiment, the double-stranded siRNA of the invention comprises an overhang of one or two nucleotides. In an embodiment, the overhang is a 3' overhang. In an embodiment, the overhang is a 5' overhang. In an embodiment, the overhang is a 3' overhang of two nucleotides. In an embodiment, the overhang is one of UU, UG or dTdT. In an embodiment, the double-stranded siRNA of the invention comprises an overhang of one or two nucleotides on each of its two strands. In an embodiment, the two overhangs are 3' overhangs. In an embodiment, the two overhangs are of one nucleotide each. In an embodiment, the two overhangs are of two nucleotides each. In an embodiment, the overhangs are one of UU, UG or dTdT. In an embodiment, the 5' terminal residue of a strand of the siRNA is phosphorylated. In an embodiment the 5' terminal residue of the antisense strand of the siRNA is phosphorylated.

In one embodiment, RNAi inhibition of KIF19 or of Kif19 gene product expression is effected by a short hairpin RNA ("shRNA"). The shRNA is introduced into the appropriate cell by transduction with a vector. In an embodiment, the vector is a lentiviral vector. In an embodiment, the vector comprises a promoter. In an embodiment, the promoter is a U6 or H1 promoter. In an embodiment the shRNA encoded by the vector is a first nucleotide sequence ranging from 19-29 nucleotides complementary to the target gene/mRNA, in the present case the mRNA encodes Kif19 gene product. In an embodiment the Kif19 gene product is a human Kif19 gene product. In an embodiment the shRNA encoded by the vector also comprises a short spacer of 4-15 nucleotides (a loop, which does not hybridize) and a 19-29 nucleotide sequence that is a reverse complement of the first nucleotide sequence. In an embodiment the siRNA resulting from intracellular processing of the shRNA has overhangs of 1 or 2 nucleotides. In an embodiment the siRNA resulting from intracellular processing of the shRNA overhangs has two 3' overhangs. In an embodiment the overhangs are, independently, UU, UG or dTdT.

In a preferred embodiment, the inhibitor of KIF19 or of Kif19 gene product expression is an siRNA. In a preferred embodiment the siRNA is encapsulated in a nanoparticle. In an embodiment, the nanoparticle comprises a hydrogel/sugar glass composite. In an embodiment the nanoparticle is a liposomal nanoparticle. In an embodiment, the nanoparticle is PEGylated. In embodiments the PEG is PEG-500 or PEG-3000 or PEG-5000. In an embodiment, the nanoparticle is doped with amino silanes. In an embodiment, the nanoparticle is paramagnetic.

In embodiments, the siRNA, or the shRNA, (the KIF19 siRNA, the KIF19 shRNA, the CEP192 siRNA or the CEP192 shRNA, or the gene product siRNAs or shRNAs) is modified at a 2 position of a sugar of at least one nucleotide thereof of at least one strand thereof. In an embodiment the modification is on a guide strand thereof. In an embodiment, the shRNA is modified. In an embodiment, the siRNA is modified. In an embodiment, the modification is a 2'-OMe modification. In an embodiment, the modification is a 2'-F modification. In an embodiment, the modification is a 2'-O-benzyl modification. In an embodiment, the modification is a 2'-O-methyl-4-pyridine (2'-O—CH$_2$Py(4)) modification.

As used herein an "aptamer", with regard to KIF19 or Kif19, is a single-stranded oligonucleotide or oligonucleotide analog that binds to a Kif19 gene product, or to a nucleic acid (such as KIF19) encoding a Kif19 gene product, and inhibits the function or expression thereof, as appropriate.

The present invention provides kits for treating wounds or scarring, a kit for treating or inhibiting metastasis, a kit for treating or inhibiting fibrosis, the kit comprising an inhibitor of KIF19 or an inhibitor of Kif19.

A composition provided in such a kit for treating or inhibiting metastasis may be provided in a form suitable for reconstitution prior to use (such as a lyophilized injectable composition) or in a form which is suitable for immediate application by, for example, injection, such as an aqueous composition.

A composition provided in such a kit for treating wounds or scarring may be provided in a form suitable for reconstitution prior to use (such as a lyophilized injectable composition) or in a form which is suitable for immediate application to a wound, including to the wound margin, such as a lotion or ointment. In an embodiment for treating wounds, the inhibitor of KIF19 or of Kif19 gene product is administered locally to the wound.

In an embodiment, the inhibitor of KIF19 or of Kif19 product is administered via a vein or artery. In an embodiment, the inhibitor of KIF19 or of Kif19 gene product is administered by injection, catheterization or cannulation.

In an embodiment, the inhibitor of KIF19 or of Kif19 gene product is administered from an implant that elutes the inhibitor, for example a eluting stent or an eluting skin patch.

In an embodiment, the wound is an epidermal wound. In an embodiment, the wound is a skin wound. In an embodiment, the wound is a cardiac tissue wound. In an embodiment, the wound is a cardiovascular wound, for example resulting from a myocardial infarction. In an embodiment, the wound is a neuronal wound. In an embodiment for treating wounds, the inhibitor of Kif19 is provided by a subcutaneous implant or depot medicament system for the pulsatile delivery of the inhibitor to a wound or site where a wound is to expected be formed to promote wound healing. The inhibitor can be provided, for example, in a therapeutically effective amount to each centimeter of a wound margin or each centimeter of a site at which a wound is expected to be formed. The benefits that may be derived from the present invention may be applicable to wounds at sites throughout the body. However, it may be preferred that the wound for which healing is promoted is a skin wound. For illustrative purposes the embodiments of the invention will generally be described with reference to skin wounds, although they remain applicable to other tissues and organs. Merely by way of example, in another preferred embodiment the wound may be a wound of the circulatory system, particularly of a blood vessel. Other wounds in which wound healing may be promoted in accordance with the present invention include as a result of surgery or as a result of a burn. Other wounds in which wound healing may be promoted in accordance with the present invention include skin ulcers caused by pressure, venous stasis, or diabetes mellitus. Examples of specific wounds in which healing may be promoted using the medicaments and methods of treating wounds or promoting healing of wounds described herein include, but are not limited to, those independently selected from the group consisting of: wounds of the skin; wounds of the eye (including the inhibition of scarring resulting from eye surgery such as LASIK surgery, LASEK surgery, PRK surgery, glaucoma filtration surgery, cataract surgery, or surgery in which the lens capsule may be subject to scarring) such as those giving rise to corneal cicatrisation; wounds subject to capsular contraction (which is common surrounding breast implants); wounds of blood vessels; wounds of the central and peripheral nervous system (where prevention, reduction or inhibition of scarring may enhance neuronal reconnection and/or neuronal function); wounds of tendons, ligaments or muscle; wounds of the oral cavity, including the lips and palate (for example, to inhibit scarring resulting from treatment of cleft lip or palate); wounds of the internal organs such as the liver, heart, brain, digestive tissues and reproductive tissues; wounds of body cavities such as the abdominal cavity, pelvic cavity and thoracic cavity (where inhibition of scarring may reduce the number of incidences of adhesion formation and/or the size of adhesions formed); and surgical wounds (in particular wounds associated with cosmetic procedures, such as scar revision). It is particularly preferred that the medicaments and methods of the invention regarding wounds be used to promote healing of wounds of the skin.

A medicament in accordance with this aspect of the invention may be formulated in any appropriate carrier. Suitable carriers are pharmaceutically acceptable carriers, for example, preferably those consistent with administration topically or administration by injection for treating wounds and treating or preventing fibrosis; preferably those consistent with administration intravenously or administration by injection or cannulation for treating or preventing metastasis. It will be appreciated that, while the inhibitor of Kif19 may be administered by the same route and in the same form in each incidence of treatment, different incidences of treatment may provide the inhibitor of Kif19 by different medicaments and/or different routes of administration. In embodiments of the invention the initial incidence of treatment may provide the inhibitor of Kif19 by means of an injection, such as an intradermal injection, while the second (and any subsequent) incidences of treatment may involve provision of the inhibitor of Kif19 by alternative routes, such as topical formulations, or vice versa. In an embodiment, multiple administrations of the inhibitor of Kif19 may be effected by the same means or route. In an embodiment the shRNA or siRNA inhibitor of Kif19 can be administered such that it is transfected into one or more cells.

In a non-limiting embodiment the inhibitor of KIF 19 or Kif19 is provided in a bulk-eroding system such as polylactic acid and glycolic acid (PLGA) copolymer based microspheres or microcapsules systems containing the inhibitor of Kif19. In an embodiment, blends of PLGA: ethylcellulose systems may be used as an appropriate carrier. A further medicament in accordance with this aspect of the invention may be formulated in a surface-eroding system wherein the inhibitor of Kif19 or of KIF19 is embedded in an erodible matrix such as the poly(ortho) ester and polyanhydride matrices wherein the hydrolysis of the polymer is rapid. A medicament in accordance with this aspect of the invention may also be formulated by combining a pulsatile delivery system as described above and an immediate release system such as a lyophilized injectable composition described above.

The inhibitor may be used in a composition with additives. Examples of suitable additives are sodium alginate, as a gelatinizing agent for preparing a suitable base, or cellulose derivatives, such as guar or xanthan gum, inorganic gelatinizing agents, such as aluminum hydroxide or bentonites (termed thixotropic gel-formers), polyacrylic acid derivatives, such as Carbopol®, polyvinylpyrrolidone, microcrystalline cellulose and carboxymethylcellulose. Amphiphilic low molecular weight and higher molecular weight compounds, and also phospholipids, are also suitable. The gels can be present either as water-based hydrogels or as hydrophobic organogels, for example based on mixtures of low and high molecular weight paraffin hydrocarbons and vaseline. The hydrophilic organogels can be prepared, for example, on the basis of high molecular weight polyethylene glycols. These gelatinous forms are washable. Hydrophobic organogels are also suitable. Hydrophobic additives, such as petroleum jelly, wax, oleyl alcohol, propylene glycol monostearate and/or propylene glycol monopalmitostearate, in particular isopropyl myristate can be included. In an embodiment the inhibitor is in a composition comprising one or more dyes, for example yellow and/or red iron oxide and/or titanium dioxide for the purpose of matching as regards color. Compositions may be in any suitable form including gels, lotions, balms, pastes, sprays, powders, bandages, wound dressing, emulsions, creams and ointments of the mixed-phase or amphiphilic emulsion systems (oil/water-water/oil mixed phase), liposomes and transfersomes or plasters/band aid-type coverings. Emulsifiers which can be employed in compositions comprising the inhibitor of KIF19 or of Kif19 include anionic, cationic or neutral surfactants, for example alkali metal soaps, metal soaps, amine soaps, sulphurated and sulphonated compounds, invert soaps, higher fatty alcohols, partial fatty acid esters of sorbitan and polyoxyethylene sorbitan, e.g. lanette types, wool wax, lanolin or other synthetic products for preparing the oil/water and/or water/oil emulsions.

Compositions comprising the inhibitor of Kif19 can also comprise vaseline, natural or synthetic waxes, fatty acids, fatty alcohols, fatty acid esters, for example as monoglycerides, diglycerides or triglycerides, paraffin oil or vegetable oils, hydrogenated castor oil or coconut oil, hog fat, synthetic fats (for example based on caprylic acid, capric acid, lauric acid or stearic acid, such as Softisan®), or triglyceride mixtures, such as Miglyol®, can be used as lipids, in the form of fatty and/or oleaginous and/or waxy components for preparing the ointments, creams or emulsions of the compositions comprising the inhibitor of Kif19 used in the methods described herein.

Osmotically active acids and alkaline solutions, for example hydrochloric acid, citric acid, sodium hydroxide solution, potassium hydroxide solution, sodium hydrogen carbonate, may also be ingredients of the compositions of the invention and, in addition, buffer systems, such as citrate, phosphate, tris buffer or triethanolamine, for adjusting the pH. It is possible to add preservatives as well, such as methyl benzoate or propyl benzoate (parabens) or sorbic acid, for increasing the stability.

Pastes, powders and solutions are additional forms of compositions comprising the inhibitor of Kif19 which can be applied topically. As consistency-imparting bases, the pastes frequently contain hydrophobic and hydrophilic auxiliary substances, preferably, however, hydrophobic auxiliary substances containing a very high proportion of solids. In order to increase dispersity, and also flowability and slipperiness, and also to prevent agglomerates, the powders or topically applicable powders can, for example, contain starch species, such as wheat or rice starch, flame-dispersed silicon dioxide or siliceous earth, which also serve as diluent.

A method is provided for identifying a candidate agent for treating a wound comprising:
a) determining the activity of an amount of Kif19 gene product; and b) contacting the amount of Kif19 gene product with the candidate agent and determining the activity of the amount of Kif19 gene product in the presence of the candidate agent, wherein a decreased activity of the amount of Kif19 gene product in the presence of the candidate agent as compared to the activity of Kif19 gene product in the absence of the candidate agent indicates that the candidate agent can treat a wound, and wherein no change in or an increased activity of the amount of Kif19 gene product in the presence of the candidate agent as compared to the activity of Kif19 gene product in the absence of the candidate agent does not indicate that the candidate agent can treat a wound. In an embodiment, the candidate agent is a small molecule of 2000 Daltons or less. In an embodiment, the candidate agent is a small molecule of 1000 Daltons or less. In an embodiment, the candidate agent is a small molecule of 1500 Daltons or less. In an embodiment, the candidate agent is a substituted or un-substituted hydrocarbon small molecule. In an embodiment, the inhibitor or the candidate agent is an aptamer, a nucleic acid, an oligonucleotide, or a small organic molecule of 2000 Daltons or less. In an embodiment, the inhibitor is cell-membrane permeable.

A pharmaceutical composition is provided comprising an amount of an inhibitor of CEP192 or of Cep192 gene product. In an embodiment, the pharmaceutical composition comprises an amount of an inhibitor of CEP192 or of Cep192 gene product effective to treat a wound in a human subject, or comprises an amount of an inhibitor of CEP192 or of Cep192 gene product effective to treat or inhibit metastasis in a subject, or comprises an amount of an inhibitor of CEP192 or of Cep192 gene product effective to treat or inhibit fibrosis in a subject, or comprises an amount of an inhibitor of CEP192 or of Cep192 gene product effective to treat or inhibit pain associated with a wound or wound healing in a subject. In an embodiment, the pharmaceutical composition comprises a pharmaceutically acceptable carrier. In an embodiment of the pharmaceutical composition, the inhibitor of CEP192 or of Cep192 gene product is encapsulated, completely or partially, by a nanoparticle. In an embodiment the nanoparticle comprises a hydrogel/sugar glass composite. In an embodiment, the nanoparticle is PEGylated. In an embodiment the nanoparticle is a liposomal nanoparticle. In an embodiment, the nanoparticle is paramagnetic. In an embodiment of the methods and compositions, the inhibitor is an siRNA which inhibits expression of Cep192 gene product. In an embodiment, the inhibitor is an shRNA which inhibits expression of Cep192 gene product.

The optimal dosage of the CEP192 inhibitor or of Cep192 gene product inhibitor administered in treatments herein will vary depending upon factors such as the pharmacodynamic characteristics of a specific inhibitor and its mode and route of administration; the age, sex, metabolic rate, absorptive efficiency, health and weight of the recipient; the nature and extent of the symptoms; the kind of concurrent treatment being administered; the frequency of treatment with the inhibitor and the desired therapeutic effect. A dosage unit of the CEP192 inhibitor or of Cep192 gene product inhibitor may comprise a single compound, or a mixture of the compound with one or more anti-infection compound(s) or wound healing-promoting compound(s); one or more anti-cancer compounds; or one or more anti-fibrotic compounds; or one or more pain-relieveing compounds, as relevant to the condition being treated.

In an embodiment of the methods or compositions, inhibition of CEP192 or of Cep192 is effected by RNAi. In an embodiment, RNAi inhibition of CEP192 or of Cep192 gene product expression is effected with an siRNA. The siRNA (small interfering RNA) as used in the methods or compositions described herein comprises a portion which is complementary to a nucleic acid, in a non-limiting example an mRNA, sequence encoding a Cep192 gene product. In an embodiment, the Cep192 gene product is a human Cep192 gene product. In an embodiment, the mRNA is or is encoded by NCBI Reference Sequence: NM_032142.3 (SEQ ID NO:3), and the siRNA is effective to inhibit expression of Cep192 gene product. In an embodiment, the mRNA is or is encoded by a known variant of NCBI Reference Sequence: NM_032142.3 (SEQ ID NO:3), and the siRNA is effective to inhibit expression of Cep192 gene product. In an embodiment, the Cep192 gene product comprises consecutive amino acid residues having the sequence set forth in SEQ ID NO:4.

In an embodiment, the siRNA with regard to CEP192/Cep192 gene product comprises a double-stranded portion (duplex). In an embodiment, the siRNA is 20-25 nucleotides in length. In an embodiment the siRNA comprises a 19-21 core RNA duplex with a one or two nucleotide 3' overhang on, independently, either one or both strands. The siRNA can be 5' phosphorylated, or not, and may be modified with any of the known modifications in the art to improve efficacy and/or resistance to nuclease degradation. In an embodiment, the siRNA is 5' phosphorylated. In an embodiment, the 5' terminal residue of a strand of the siRNA is phosphorylated. In an embodiment the 5' terminal residue of the antisense strand of the siRNA is phosphorylated. In one embodiment, a siRNA of the invention comprises a double-stranded RNA wherein one strand of the double-stranded RNA is 80%, 85%, 90%, 95% or 100% complementary to a portion of an RNA transcript of a CEP192 (gene) encoding Cep192 gene product. In an embodiment, the RNA transcript of a gene encoding Cep192 gene product is an mRNA. In an embodiment, the Cep192 gene product is a human Cep192 gene product.

In an embodiment, a siRNA of the invention with regard to CEP192/Cep192 gene product comprises a double-stranded RNA wherein one strand of the RNA comprises a portion having a sequence the same as a portion of 18-25 consecutive nucleotides of an RNA transcript of a gene encoding Cep192 gene product. In an embodiment, the other strand is fully complementary to the one strand. In an embodiment, the Cep192 gene product is a human Cep192 gene product. In yet another embodiment, a siRNA of the invention comprises a double-stranded RNA wherein both strands of RNA are connected by a non-nucleotide linker. In yet another embodiment, a siRNA of the invention comprises a double-stranded RNA wherein the two strands of RNA are not connected other than by complementary hybridization. Alternately, a siRNA of the invention comprises a double-stranded RNA wherein both strands of RNA are connected by a nucleotide linker, such as a loop or stem loop structure. In an embodiment, one strand of the double-stranded siRNA is fully complementary to a nucleic acid encoding Cep192 gene product. In an embodiment, one strand of the double-stranded siRNA is fully complementary to a nucleic acid encoding Cep192 gene product except at one, or except at two, mismatched positions. In one embodiment, a single strand component of a siRNA of the invention is from 14 to 50 nucleotides in length. In another embodiment, a single strand component of a siRNA of the invention is 14, 15, 16, 17, 18, 19, 20, 21, 22, 23, 24, 25, 26, 27, or 28 nucleotides in length. In an embodiment, a single strand component of a siRNA of the invention is 18 nucleotides in length. In yet another embodiment, a single strand component of a siRNA of the invention is 19 nucleotides in length. In yet another embodiment, a single strand component of a siRNA of the invention is 20 nucleotides in length. In yet another embodiment, a single strand component of a siRNA of the invention is 21 nucleotides in length. In yet another embodiment, a single strand component of a siRNA of the invention is 22 nucleotides in length. In yet another embodiment, a single strand component of a siRNA of the invention is 23 nucleotides in length. In one embodiment, a siRNA of the invention is from 28 to 56 nucleotides in length. Tn another embodiment, a siRNA of the invention is 40, 41, 42, 43, 44, 45, 46, 47, 48, 49, 50, 51, or 52 nucleotides in length. In an embodiment, an siRNA of the invention comprises at least one 2'-sugar modification. In an embodiment, an siRNA of the invention comprises at least one nucleic acid base modification. In an embodiment, an siRNA of the invention comprises at least one phosphate backbone modification. As used herein, "at least one" means one or more. In an embodiment, the double-stranded siRNA of the invention comprises an overhang of one or two nucleotides. In an embodiment, the overhang is a 3' overhang. In an embodiment, the overhang is a 5' overhang. In an embodiment, the overhang is a 3' overhang of two nucleotides. In an embodiment, the overhang is one of UU, UG or dTdT. In an embodiment, the double-stranded siRNA of the invention comprises an overhang of one or two nucleotides on each of its two strands. In an embodiment, the two overhangs are 3' overhangs. In an embodiment, the two overhangs are of one nucleotide each. In an embodiment, the two overhangs are of two nucleotides each. In an embodiment, the overhangs are, independently, one of UU, UG or dTdT. In an embodiment, the 5' terminal residue of a strand of the siRNA is phosphorylated. In an embodiment the 5' terminal residue of the antisense strand of the siRNA is hosphorylated.

In one embodiment, RNAi inhibition of CEP192 or of Cep192 gene product expression is effected by a short hairpin RNA ("shRNA"). The shRNA is introduced into the appropriate cell by transduction with a vector. Tn an embodiment, the vector is a lentiviral vector. In an embodiment, the vector comprises a promoter. In an embodiment, the promoter is a U6 or H1 promoter. In an embodiment the shRNA encoded by the vector is a first nucleotide sequence ranging from 19-29 nucleotides complementary to the target gene/mRNA, in the present case the mRNA encodes Cep192 gene product. In an embodiment the Cep192 gene product is a human Cep192 gene product. In an embodiment the shRNA encoded by the vector also comprises a short spacer of 4-15 nucleotides (a loop, which does not hybridize) and a 19-29 nucleotide sequence that is a reverse complement of the first nucleotide sequence. In an embodiment the siRNA resulting from intracellular processing of the shRNA has overhangs of 1 or 2 nucleotides. In an embodiment the siRNA resulting from intracellular processing of the shRNA overhangs has two 3' overhangs. In an embodiment the overhangs are, independently, UU, UG or dTdT.

As used herein an "aptamer", with regard to CEP192 or Cep192, is a single-tranded oligonucleotide or oligonucleotide analog that binds to a Cep192 gene product, or to a nucleic acid (such as CEP192) encoding a Cep192 gene product, and inhibits the function or expression thereof, as appropriate.

The present invention provides kits for treating wounds or scarring, a kit for treating or inhibiting metastasis, a kit for treating or inhibiting fibrosis, or a kit for treating or inhibiting pain associated with a wound or with wound healing, the kit comprising an inhibitor of CEP192 or an inhibitor of Cep192.

A composition provided in such a kit for treating or inhibiting metastasis may be provided in a form suitable for reconstitution prior to use (such as a lyophilized injectable composition) or in a form which is suitable for immediate application by, for example, injection, such as an aqueous composition.

A composition provided in such a kit for treating or inhibiting pain associated with a wound or with wound healing, may be provided in a form suitable for reconstitution prior to use (such as a lyophilized injectable composition) or in a form which is suitable for immediate application by, for example, injection, such as an aqueous composition, or a form for immediate topical application, such as a lotion or ointment.

A composition provided in such a kit for treating wounds or scarring may be provided in a form suitable for reconstitution prior to use (such as a lyophilized injectable composition) or in a form which is suitable for immediate application to a wound, including to the wound margin, such as a lotion or ointment. In an embodiment for treating wounds, the inhibitor of CEP192 or of Cep192 gene product is administered locally to the wound.

In an embodiment, the inhibitor of CEP192 or of Cep192 product is administered via a vein or artery. In an embodiment, the inhibitor of CEP192 or of Cep192 gene product is administered by injection, catheterization or cannulation.

In an embodiment, the inhibitor of CEP192 or of Cep192 gene product is administered from an implant that elutes the inhibitor, for example a eluting stent or an eluting skin patch.

In an embodiment, the wound is an epidermal wound. In an embodiment, the wound is a skin wound. In an embodiment, the wound is a cardiac tissue wound. In an embodiment, the wound is a cardiovascular wound, for example resulting from a myocardial infarction. In an embodiment, the wound is a neuronal wound. In an embodiment of the invention the inhibitor of Cep192 is provided by a subcutaneous implant or depot medicament system for the pulsatile delivery of the inhibitor to a wound or site where a wound is to expected be formed to promote wound healing. The inhibitor can be provided, for example, in a therapeutically effective amount to each centimeter of a wound margin or each centimeter of a site at which a wound is expected to be formed. The benefits that may be derived from the present invention may be applicable to wounds at sites throughout the body. However, it may be preferred that the wound for which healing is promoted is a skin wound. For illustrative purposes the embodiments of the invention will generally be described with reference to skin wounds, although they remain applicable to other tissues and organs. Merely by way of example, in another preferred embodiment the wound may be a wound of the circulatory system, particularly of a blood vessel. Other wounds in which wound healing may be promoted in accordance with the present invention include as a result of surgery or as a result of a burn. Other wounds in which wound healing may be promoted in accordance with the present invention include skin ulcers caused by pressure, venous stasis, or diabetes mellitus. In an embodiment, the inhibitor of CEP192 or of Cep192 gene product is administered locally to the wound. In an embodiment, the inhibitor of CEP192 or of Cep192 gene product is administered via a vein or artery. In an embodiment, the inhibitor of CEP19 or of Cep19 gene product is administered by injection, catheterization or cannulation. In an embodiment, the inhibitor of CEP192 or of Cep19 gene product is administered from an implant that elutes the inhibitor, for example a eluting stent or an eluting skin patch. In an embodiment, the wound is an epidermal wound. In an embodiment, the wound is a skin wound. In an embodiment, the wound is a cardiac tissue wound. In an embodiment, the wound is a cardiovascular wound, for example resulting from a myocardial infarction. In an embodiment, the wound is a neuronal wound. Examples of specific wounds in which healing may be promoted using the medicaments and methods of treating wounds or promoting healing of wounds described herein include, but are not limited to, those independently selected from the group consisting of: wounds of the skin; wounds of the eye (including the inhibition of scarring resulting from eye surgery such as LASIK surgery, LASEK surgery, PRK surgery, glaucoma filtration surgery, cataract surgery, or surgery in which the lens capsule may be subject to scarring) such as those giving rise to corneal cicatrisation; wounds subject to capsular contraction (which is common surrounding breast implants); wounds of blood vessels; wounds of the central and peripheral nervous system (where prevention, reduction or inhibition of scarring may enhance neuronal reconnection and/or neuronal function); wounds of tendons, ligaments or muscle; wounds of the oral cavity, including the lips and palate (for example, to inhibit scarring resulting from treatment of cleft lip or palate); wounds of the internal organs such as the liver, heart, brain, digestive tissues and reproductive tissues; wounds of body cavities such as the abdominal cavity, pelvic cavity and thoracic cavity (where inhibition of scarring may reduce the number of incidences of adhesion formation and/or the size of adhesions formed); and surgical wounds (in particular wounds associated with cosmetic procedures, such as scar revision). It is particularly preferred that the medicaments and methods of the invention regarding wounds be used to promote healing of wounds of the skin.

A medicament in accordance with this aspect of the invention may be formulated in any appropriate carrier. Suitable carriers are pharmaceutically acceptable carriers, for example, preferably those consistent with administration topically or administration by injection for treating wounds and treating or preventing fibrosis; preferably those consistent with administration intravenously or administration by injection or cannulation for treating or preventing metastasis. It will be appreciated that, while the inhibitor of Cep192 or CEP192 may be administered by the same route and in the same form in each incidence of treatment, different incidences of treatment may provide the inhibitor of Cep192 by different medicaments and/or different routes of administration. In embodiments of the invention the initial incidence of treatment may provide the inhibitor of Cep 192 by means of an injection, such as an intradermal injection, while the second (and any subsequent) incidences of treatment may involve provision of the inhibitor of Cep192 by alternative routes, such as topical formulations, or vice versa. In an embodiment, multiple administrations of the inhibitor of Cep192 may be effected by the same means or route.

In an embodiment the shRNA or siRNA inhibitor of CEP192 or of Cep192 gene product expression can be administered such that it is transfected into one or more cells.

In a preferred embodiment, the inhibitor is an siRNA. In a preferred embodiment the siRNA is encapsulated in a nanoparticle. In an embodiment, the nanoparticle comprises a hydrogel/sugar glass composite. In an embodiment the nanoparticle is a liposomal nanoparticle. In an embodiment, the nanoparticle is PEGylated. In embodiments the PEG is PEG-500 or PEG-3000 or PEG-5000. In an embodiment, the nanoparticle is doped with amino silanes. In an embodiment, the nanoparticle is paramagnetic.

In a non-limiting embodiment the inhibitor of CEP192 or of Cep192 gene product is provided in a bulk-eroding system such as polylactic acid and glycolic acid (PLGA) copolymer based microspheres or microcapsules systems containing the inhibitor of Cep192. In an embodiment, blends of PLGA:ethylcellulose systems may be used as an appropriate carrier. A further medicament in accordance with this aspect of the invention may be formulated in a surface-eroding system wherein the inhibitor of Cep192 is embedded in an erodible matrix such as the poly(ortho) ester and polyanhydride matrices wherein the hydrolysis of the polymer is rapid. A medicament in accordance with this aspect of the invention may also be formulated by combining a pulsatile delivery system as described above and an immediate release system such as a lyophilized injectable composition described above.

The inhibitor may be used in a composition with additives. Examples of suitable additives are sodium alginate, as a gelatinizing agent for preparing a suitable base, or cellulose derivatives, such as guar or xanthan gum, inorganic gelatinizing agents, such as aluminum hydroxide or bentonites (termed thixotropic gel-formers), polyacrylic acid derivatives, such as Carbopol®, polyvinylpyrrolidone, microcrystalline cellulose and carboxymethylcellulose. Amphiphilic low molecular weight and higher molecular weight compounds, and also phospholipids, are also suitable. The gels can be present either as water-based hydrogels or as hydrophobic organogels, for example based on mixtures of low and high molecular weight paraffin hydrocarbons and vaseline. The hydrophilic organogels can be prepared, for example, on the basis of high molecular weight polyethylene glycols. These gelatinous forms are washable. Hydrophobic organogels are also suitable. Hydrophobic additives, such as petroleum jelly, wax, oleyl alcohol, propylene glycol monostearate and/or propylene glycol monopalmitostearate, in particular isopropyl myristate can be included. In an embodiment the inhibitor is in a composition comprising one or more dyes, for example yellow and/or red iron oxide and/or titanium dioxide for the purpose of matching as regards color. Compositions may be in any suitable form including gels, lotions, balms, pastes, sprays, powders, bandages, wound dressing, emulsions, creams and ointments of the mixed-phase or amphiphilic emulsion systems (oil/water-water/oil mixed phase), liposomes and transfersomes or plasters/band aid-type coverings. Emulsifiers which can be employed in compositions comprising the inhibitor of CEP192 or of Cep192 include anionic, cationic or neutral surfactants, for example alkali metal soaps, metal soaps, amine soaps, sulphurated and sulphonated compounds, invert soaps, higher fatty alcohols, partial fatty acid esters of sorbitan and polyoxyethylene sorbitan, e.g. lanette types, wool wax, lanolin or other synthetic products for preparing the oil/water and/or water/oil emulsions.

Compositions comprising the inhibitor of CEP192 or of Cep192 can also comprise vaseline, natural or synthetic waxes, fatty acids, fatty alcohols, fatty acid esters, for example as monoglycerides, diglycerides or triglycerides, paraffin oil or vegetable oils, hydrogenated castor oil or coconut oil, hog fat, synthetic fats (for example based on caprylic acid, capric acid, lauric acid or stearic acid, such as Softisan®), or triglyceride mixtures, such as Miglyol®, can be used as lipids, in the form of fatty and/or oleaginous and/or waxy components for preparing the ointments, creams or emulsions of the compositions comprising the inhibitor of CEP192 or of Cep192 used in the methods described herein.

Osmotically active acids and alkaline solutions, for example hydrochloric acid, citric acid, sodium hydroxide solution, potassium hydroxide solution, sodium hydrogen carbonate, may also be ingredients of the compositions of the invention and, in addition, buffer systems, such as citrate, phosphate, tris buffer or triethanolamine, for adjusting the pH. It is possible to add preservatives as well, such as methyl benzoate or propyl benzoate (parabens) or sorbic acid, for increasing the stability.

Pastes, powders and solutions are additional forms of compositions comprising the inhibitor of Cep192 which can be applied topically. As consistency-imparting bases, the pastes frequently contain hydrophobic and hydrophilic auxiliary substances, preferably, however, hydrophobic auxiliary substances containing a very high proportion of solids. In order to increase dispersity, and also flowability and slipperiness, and also to prevent agglomerates, the powders or topically applicable powders can, for example, contain starch species, such as wheat or rice starch, flame-dispersed silicon dioxide or siliceous earth, which also serve as diluent.

In an embodiment, insofar as the methods herein pertain to wounds or scarring, the compositions comprise further active ingredients suitable for protecting or aiding in healing of the wound, for example one or more antibiotics, antiseptics, vitamins, anesthetics, antihistamines, anti-inflammatory agents, moisturizers, penetration-enhancing agents and/or anti-irritants.

In an embodiment of the methods and compositions described herein the subject is a mammal. In an embodiment the subject is human.

As used herein, "promotion" of wound healing, or grammatical equivalent, means an acceleration in any one or more of visual appearance of wound recovery, reduction in wound size, reduction in distance between wound margins, scab formation, fibroplasia and re-epithelialization as compared to the corresponding parameter in an untreated wound.

As used herein, "wound" is a break or discontinuity in the structure of an organ or tissue (including skin), which includes epithelium, connective tissue, and muscle tissue, caused by an external agent. Examples of wounds include, but are not limited to, skin wounds, ulcerations, bedsores, grazes, tears, cuts, punctures, tympanic membrane perforations, burns, and those that are a consequence of plastic surgery procedures.

A method is provided for identifying a candidate agent for treating a wound comprising:
a) determining the activity of an amount of Cep192 gene product; and
b) contacting the amount of Cep192 gene product with the candidate agent and determining the activity of the amount of Cep192 gene product in the presence of the candidate agent, wherein a decreased activity of the amount of Cep192 gene product in the presence of the candidate agent as compared to the activity of Cep192 gene product in the absence of the candidate agent indicates that the candidate agent can treat a wound, and wherein no change in or an increased activity of the amount of Cep192 gene product in the presence of the candidate agent as compared to the activity of Cep192 gene product in the absence of the candidate agent does not indicate that the candidate agent can treat a wound. In an embodiment, the candidate agent is a small molecule of 2000 Daltons or less. In an embodiment, the candidate agent is a small molecule of 1000 Daltons or less. In an embodiment, the candidate agent is a small molecule of 1500 Daltons or less. In an embodiment, the candidate agent is a substituted or un-substituted hydrocarbon small molecule. In an embodiment, the inhibitor or the candidate agent is an aptamer, a nucleic acid, an oligonucleotide, or a small organic molecule of 2000 Daltons or less. In an embodiment, the inhibitor is cell-membrane permeable.

With regard to the methods described herein to identify candidate agents as inhibitors of Kif19 or of KIF19 of of CEP192 or of Cep192, one skilled in the art can readily screen libraries of compounds, for example small molecule libraries, using the methods as described to identify agents which are inhibitors of Kif19 or of KIF19 of of CEP192 or of Cep192 and which are therapeutic in treating wounds and promoting the healing of wounds. In addition, one skilled in the art can employ the method to identify peptides, peptidomimetics, antibodies, antibody fragments and nucleic acids which are inhibitors of Kif19 or of KIF19 of of CEP192 or of Cep192 and which are therapeutic in treating wounds and promoting the healing of wounds.

An inhibitor of KIF19, or of Kif19 gene product is provided for treating metastasis or inhibiting metastasis in a subject having a cancer.

An inhibitor of CEP192 or of Cep192 gene product is provided for treating metastasis or inhibiting metastasis in a subject having a cancer.

An inhibitor of KIF19, or of Kif19 gene product, is provided for treating fibrosis or scarring in a subject in need thereof.

An inhibitor of CEP192 or of Cep192 gene product, is provided for treating fibrosis or scarring in a subject in need thereof.

An inhibitor of CEP192 or of Cep192 gene product, for treating pain associated with wound healing in a subject.

In an embodiment, the inhibitor is an RNAi nucleic acid. In an embodiment, the inhibitor comprises an siRNA. In an embodiment, the inhibitor comprises an shRNA. In an embodiment, the siRNA or shRNA is directed against CEP192. In an embodiment, the siRNA or shRNA is directed against KIF19.

In an embodiment of the methods, prodcuts and compositions, the inhibitor is biomembrane-permeable or is conjugated or otherwise attached to a moiety which renders the inhibitor biomembrane-permeable.

In an embodiment, KIF19 comprises the following sequence (SEQ ID NO:1):

```
  1    gcgttgttgg tttcggggttg tcaggcagcg cgcgaggcgg cgggcagcta gcagctggcg
 61    gacgcgaccc ggaggcggtg ggggtgcggc tgagccatgc ccggtggcgc ggcctgagcc
121    cctccacctg ctgcaatcat gaaggacagc ggggactcca aggaccagca actcatggtg
181    gcgcttcggg tccggcccat cagcgtggca gagctggagg aaggagctac cctcatcgcc
241    cataaagtgg atgagcagat ggtggttctc atggacccaa tggaggatcc cgacgacatc
```

-continued

```
 301   ctgcgggcgc atcgctcccg ggagaagtcc tacctgttcg acgtggcctt tgacttcacc
 361   gccacccagg agatggtgta tcaggccacc accaagagcc tcatcgaggg cgtcatctca
 421   ggctacaatg ccactgtctt tgcctatggc cccacaggct gtgggaaaac ctacaccatg
 481   ctgggcacag accaggagcc tggcatctat gttcagaccc tcaacgacct cttccgtgcc
 541   atcgaggaga ccagcaatga catggagtat gaggtctcca tgtcctacct ggagatctac
 601   aatgagatga tccgggacct gctgaacccc tccctgggct acctggagct gcgggaggac
 661   tctaaggggg tgatccaggt ggccggcatc accgaagtct ccaccatcaa tgccaaggag
 721   atcatgcagc tgctgatgaa ggggaaccgg cagaggaccc aggagcccac ggccgccaac
 781   cagacgtcct cccgctccca cgcggtactg caggtgaccg tgcgccagcg cagccgggtc
 841   aagaacatct gcaggaggt gcggcagggc cgcctgttca tgatcgacct ggctggctca
 901   gagcgcgcct cgcagacaca gaatcgtggg cagcgtatga aggagggggc ccacatcaac
 961   cgctcactgc tggcactggg caactgcatc aacgccctga gcgacaaggg tagcaacaag
1021   tacatcaact atcgcgacag caagctcacc cggctcctga aggactctct gggaggaaac
1081   agccgcacag tgatgatcgc tcacatcagt cctgcgagca gtgccttcga ggagtcccgg
1141   aacaccctga cctacgccgg ccgggccaag aacattaaga ctagggtgaa gcagaacctc
1201   ctgaacgtct cctaccacat cgcccagtac accagcatca tcgctgacct gcggggcgag
1261   atccagcgac tcaagcgcaa gattgatgag cagactgggc ggggccaggc ccggggccgg
1321   caggatcggg gtgacatccg ccacatccaa gctgaggtcc agctgcacag cgggcagggt
1381   gagaaggctg gcatgggaca gcttcgggag cagctcgcca gcgccttcca ggagcagatg
1441   gatgtgcgga ggcgcctgct ggagctggag aaccgcgcca tggaggtcca gattgacacc
1501   tcccgacacc tgctcaccat cgccggctgg aagcatgaga agtcccgccg ggccctcaaa
1561   tggcgggagg agcagcgaaa ggagtgctac gctaaggacg acagcgagaa ggactcagac
1621   acaggtgatg accaaccaga catcctggag ccacccgagg tggccgcagc ccgggagagc
1681   attgcagccc tggtggacga gcagaagcaa ctgcgcaagc agaagctggc gctggagcag
1741   cgctgccggg agctgcgcgc gcggggccgg cgcctggagg agacgctgcc gcggcgcatc
1801   ggctccgagg agcagcgcga ggtgctcagc ctgctgtgcc gcgtgcacga gctcgaggtg
1861   gagaacaccg agatgcagtc gcacgcgctg ctccgcgacg tgcgctccg ccaccgccac
1921   gaggccgtgc gccgcctgga gcagcaccgc agtctctgcg acgagattat ccagggccag
1981   cggcagatca tcgacgacta caacctggcc gtcccgcagc gcctggaaga gctctacgaa
2041   gtgtacctgc gggagctgga ggagggcagc ctggagcagg ccaccatcat ggaccaagtg
2101   gcctccaggg ccctgcagga cagctccttg cccaaaatta ccccagcagg aacctcactg
2161   accccagatt ctgacctgga gagtgtgaag acattgagct ctgatgccca gcacctgcag
2221   aacagcgccc tccctcccct cagcacagag agtgaaggcc accacgtgtt caaggctggt
2281   actggggcct ggcaggcaaa aagctcctct gtgcccaccc cacctcccat ccagctcggc
2341   agcctggtga cgcaggaggc cccggctcag gacagcctgg gcagctggat caactcttcc
2401   cctgacagca gtgagaacct gtcggagatc cccttgtccc acaaagagag gaaggagatc
2461   ctgactggca ccaagtgcat ctgggtgaag gccgcccggc ggcgctcgcg ggccctggga
2521   accgaggggc gacacctgct ggcacccgcg acagagcgca gcagcctgtc cctgcactca
2581   ctgagcgagg cgacgatgc gcggccacca ggcccactgg cctgcaagcg ccgcccagc
2641   cccacactac agcatgctgc cagtgaggac aacctgtcca gcagcacggg cgaggccccg
```

-continued

```
2701   tcccgggcag tcggacatca tggggacggc cccaggccct ggctgcgtgg ccagaagaaa
2761   agcctgggca agaaaaggga ggagtcgctg gaggcaaaga gaaggaagcg gaggtcccga
2821   tccttcgagg tcaccgggca agggctctcc caccccaaga cacacctcct ggggccccat
2881   caggcggagc gcatctcgga ccacaggatg ccagtgtgca ggcacccagc ccctggtatc
2941   cggcatctgg gaaaggtcac gctacctttg gccaaagtca aactccctcc aagccagaac
3001   acgggcccgg gggactcctc acccctggct gttccccca acccaggtgg tggttctcga
3061   cgggctaccc gtgggccccg cctgccccac ggcacaagca cccatggcaa agatggatgc
3121   tcccggcata actgaggggc cctgcctgga actggctctc tcacctccca agactgaatg
3181   gggtctagca gggcatggga ggtggaggct gggcagatgg agatgaccag gaagtaagct
3241   caggatctca gcaggccagg gctcctgaga cccaggaact ggggtctctg cccaaccctc
3301   ccatgctttc agtgccactg gggaaaagag gtgaggccag gggacatggc caggacggct
3361   gggctccctg gcttcccagc cctggacaga atgctgttgc caaaacctgc acagccctga
3421   ggccagcctc ggccttggta acggaggaaa gcagctgaca gtgagacggg gctcctggcc
3481   cacgtgtggg gcacgggcat cctggatggt tggggaggcg ccgacaggca cttcacgtat
3541   tacaattggg gatgtgggtg agggaaggaa tctggItttg ttacttggca gtggtttttt
3601   ctcacccttc cttttttaaca ataaaatccc atttgggtct tgaaaaaaaa aaaaaaaaaa
3661   aaaaaaaaaa
```

In an embodiment, Kif19 gene product comprises the following sequence (SEQ ID NO:2):

MKDSGDSKDQQLMVALRVRPISVAELEEGATLIAHKVDEQMVVL
MDPMEDPDDILRAHRSREKSYLFDVAFDFTATQEMVYQATTKSLIEGVIS
GYNATVFAYGPTGCGKTYTMLGTDQEPGIYVQTLNDLFRATEETSNDMEY
EVSMSYLETYNEMIRDLLNPSLGYLELREDSKGVIQVAGITEVSTINAKE
IMQLLMKGNRQRTQEPTAANQTSSRSHAVLQVTVRQRSRVKNILQEVRQG
RLFMIDLAGSERASQTQNRGQRMKEGAHINRSLLALGNCINALSDKGSNK
YINYRDSKLTRLLKDSLGGNSRTVMTAHTSPASSAFEESRNTLTYAGRAK
NIKTRVKQNLLNVSYHIAQYTSIIADLRGEIQRLKRKIDEQTGRGQARGR
QDRGDIRHIQAEVQLHSGQGEKAGMGQLREQLASAFQEQMDVRRRLLELE
NRAMEVQIDTSRHLLTIAGWKHEKSRRALKWREEQRKECYAKDDSEKDSD
TGDDQPDILEPPEVAAARESIAALVDEQKQLRKQKLALEQRCRELRARGR
RLEETLPRRIGSEEQREVLSLLCRVHELEVENTEMQSHALLRDGALRHRH
EAVRRLEQHRSLCDEIIQGQRQIIDDYNLAVPQRLEELYEVYLRELEEGS
LEQATIMDQVASRALQDSSLPKITPAGTSLTPDSDLESVKTLSSDAQHLQ
NSALPPLSTESEGHHVFKAGTGAWQAKSSSVPTPPPIQLGSLVTQEAPAQ
DSLGSWINSSPDSSENLSEIPLSHKERKEILTGTKCIWVKAARRRSRALG
TEGRHLLAPATERSSLSLHSLSEGDDARPPGPLACKRPPSPTLQHAASED
NLSSSTGEAPSRAVGHHGDGPRPWLRGQKKSLGKKREESLEAKRRKRRSR
SFEVTGQGLSHPKTHLLGPHQAERTSDHRMPVCRHPAPGIRHLGKVTLPL
AKVKLPPSQNTGPGDSSPLAVPPNPGGGSRRATRGPRLPHGTSTHGKDGC
SRHN

In an embodiment, CEP192 comprises the following sequence (SEQ ID NO:3):

```
  1   agtgccctgg gacacctctt cagtccgtgg actttcccgc tgcacactgc cctccgaagt
 61   cggggacgcg ggctcgtgag atggaagatt ttcgaggtat agcagaagaa tcatttccaa
121   gctttctcac caattcatta tttggtaaca gtgggatttt ggaaaatgtc actctttctt
181   caaatcttgg cttgcctgtt gctgtttcta cacttgctag ggatagatcc agcactgata
241   acaggtatcc tgatatccag gcatcttact tagtagaagg gagattttca gttccatccg
301   ggtcatctcc cggaagccag agtgatgctg aaccaagaga gaggttacag cttagcttcc
361   aggatgatga ttctatctct aggaaaaaga gctatgtgga aagtcaacgt tgtcaaatg
421   ctctcagcaa acagtcagct ttacaaatgg agacagcagg accagaagag gagccagccg
481   gagctacaga atccttgcag ggccaagatc tcttcaacag ggcttcacca ctggaacaag
```

-continued

```
 541   cacaagactc acctattgat tttcatttac agtcatggat gaataataag gaacccaaga
 601   ttgttgtgct tgatgctgga aaacattttg aagacaagac tctaaagagt gacctaagcc
 661   acactagctt attagaaaat gagaaactta tcttaccgac aagcttggaa gattcttctg
 721   atgatgatat tgatgatgaa atgttttatg atgatcattt ggaggcttat tttgaacaac
 781   tggcaattcc aggaatgata tatgaagacc tagaaggacc agaacctcca gaaaaaggtt
 841   ttaagttacc tacaaatggt cttagacagg caaatgaaaa cggtagctta aactgcaagt
 901   ttcaatcaga aaataacagc tctctgattt ccctcgactc acactcttct gaaacaactc
 961   acaaagagtc tgaggaaagc caagttattt gtctacctgg gactagtaat tctataggta
1021   ctggagatag tagaaggtac acagatggta tgttaccatt ttcctctggt acttggggaa
1081   ctgagaaaga aatagaaaat ttgaagggta ttgttccaga tcttaacagt gaatgtgcaa
1141   gtaaagatgt tctggtgaag accctcaggg ctattgatgt gaaacttaac tctgataatt
1201   ttcatgatgc aaatgccaat agaggtggtt ttgatctgac tgaccctgta aaacaggggg
1261   cagagtgtcc tcaccaaaat aagacagttt tgcacatgga tggatgttta gacactgaga
1321   ctcctacggt gtccattcaa gaaaatgtgg atgtagcctc tttgaagccc attagtgaca
1381   gtggaattaa tttcactgat gccatttggt caccaacttg tgaaaggcga acatgtgaat
1441   gtcacgagtc catcgaaaag aataaagaca aaacagatct cccacagagt gtggtctatc
1501   aaaatgaaga gggtaggtgg gtcacagacc ttgcctatta cacatctttt aatagcaaac
1561   aaaatttaaa tgtgtctcta agtgatgaga tgaatgaaga cttcagatct ggttctgaag
1621   catttgattt gattgcacaa gatgaagaag aatttaataa agagcatcaa tttatacagg
1681   aagaaacat agatgctcat aatacttcgg ttgcactggg cgatacgtcc tggggagcta
1741   caattaatta cagtctgttg aggaaatcac gtagcacatc agatttggat aaagatgatg
1801   ccagttattt acgtctgtct ttaggagagt tctttgctca aagatctgaa gctcttggtt
1861   gccttggtgg tggtaacaat gtgaaaagac catcatttgg ctattttatt agatcaccag
1921   agaagagaga acctattgcc ttaataagaa aatctgatgt atcaagaggt aatttggaaa
1981   aagaaatggc tcatcttaac catgatctat attcaggaga tttaaatgaa cagtcccagg
2041   cacagctaag tgaaggatca attacacttc aggttgaagc agtagagagt acttcacaag
2101   tggatgaaaa tgatgtgacg ttaacggctg ataaaggcaa aacagaggac actttcttca
2161   tgagcaacaa accccaaaga tacaaagaca agctaccaga tagtggtgat tctatgctta
2221   ggatcagcac cattgcttca gccattgcag aggcatcagt taatactgat ccttcccaac
2281   ttgctgcaat gatcaaggca ctttcaaata aaaccagaga caagactttt caggaagatg
2341   agaaacaaaa ggactattct catgtgcgtc atttcttacc taatgattta gaaaaaagta
2401   atggatccaa tgcacttgat atggagaaat accttaaaaa aacagaagtt agtagatatg
2461   aaagtgcatt ggaaaacttt tcaagggcta gtatgtctga tacttggat ttatctttgc
2521   ccaaagaaca aactactcaa gacattcatc cggtggactt aagtgctact agtgtaagtg
2581   tgagggcacc agaagaaaac acagcagcta ttgtttatgt tgaaaatgga gagagtgaga
2641   atcaagagtc atttagaacc ataaactcct caaattcagt tacaaataga gagaataaca
2701   gtgcagtagt tgatgtgaag acatgttcca ttgacaacaa attacaagat gttggtaacg
2761   atgaaaaagc taccctcaatt tccactccat ctgatagtta ttcatcagtg aggaaccccca
2821   gaataacatc cctttgtctg ttaaaagact gtgaagaaat acgagataac agagaaaatc
2881   agaggcaaaa tgagtgtgtc agtgaaataa gcaacagtga gaagcatgtg acttttgaaa
2941   accatcgcat agtctcacct aaaaatagtg atttgaaaaa tacctctcct gagcatggtg
```

-continued

```
3001  gacgtggctc agaggatgag caggagagct tcagaccttc cacgtcacca ctgagtcatt
3061  cttctcctag tgaaatttct ggaacgagtt catcagggtg tgcgttagag tcctttggtt
3121  cagcagctca gcagcagcag cctccctgtg agcaggagtt gtctcccttg gtgtgctcgc
3181  ctgctggggt gagcaggctg acgtatgtgt ctgaaccaga gagctcctat cctaccacag
3241  ccacagatga tgccctggag gaccgcaaga gtgatatcac cagcgagttg agtaccacaa
3301  ttattcaagg cagtccagcc gcattggagg aacgggctat ggaaaaattg agagaaaaag
3361  ttccatttca gaatagagga aaaggaacat tatcatctat tatccagaat aactctgata
3421  caagaaaagc aactgaaact acttctctga gtagcaagcc tgaatatgta aaacctgact
3481  ttagatggag taaagatcct tcctccaaaa gtggaaatct gttggaaacc agtgaggtag
3541  gttggacatc aaaccctgag gaattggacc cgatcaggct ggctctcctg ggcaagtcag
3601  gtctgagctg tcaggtgggg tcagccacat cacaccctgt gtcctgccag gagcctatag
3661  atgaagatca agaataagt cctaaagata agtcaactgc tggccgtgag ttcagtggcc
3721  aggtttctca tcagaccacc tctgaaaacc agtgtactcc tattcccagc agcacagttc
3781  acagctctgt ggctgacatg cagaacatgc tgctgctgt gcacgcactc ttgacacaac
3841  cctctctcag cgctgctcct tttgctcagc ggtatttggg aacactccct tcaactggaa
3901  gcaccacctt gcctcagtgc catgctggca atgccacagt ctgtggcttc tcaggaggcc
3961  ttccctatcc agctgttgca ggagagcctg tgcagaactc tgtggctgtg ggaatttgtc
4021  taggatcaaa tatcggctct ggatggatgg gtacctcttc cctctgtaac ccatattcta
4081  ataccttaaa tcagaacctg ctaagcacaa caaaaccttt tcctgtgccg tctgttggta
4141  caaactgtgg aattgaacca tgggattcag gagtgacatc aggattgggg agtgtccgag
4201  tgcccgagga gttgaagctt cctcatgctt gctgtgtcgg gatcgcttcc cagaccctcc
4261  tcagtgtgct taatccaact gaccgctggc tgcaagtcag cattgggctc tcagcatta
4321  gtgttaatgg tgaaaggtg gatctttcaa catatcgttg tttagttttc aagaataaag
4381  ccatcataag acctcatgcc acagaagaga taaaagtgct tttatacca tccagtcctg
4441  gggttttcag atgcacattc agtgttgctc cttggccatg ttcgacagat gctgagacca
4501  tcgtacaggc agaagctttg gccagcaccg tcactctcac tgccattgcc gagagtcctg
4561  ttattgaggt agaaacagaa agaaagacg ttcttgattt tggtgacttg acttatggag
4621  gctggaaagc cctcccacta aaattgataa accgaacgca tgccactgtg ccaattagac
4681  tgattattaa tgctaacgct gtagcctggc gctgtttcac gttttccaag gaatccgtcc
4741  gagctcctgt ggaagttgct ccttgcgctg atgtggtcac tcggctagca ggcccttctg
4801  tggtcaacca catgatgcct gctagttatg atggacagga tccagaattt ctgatgattt
4861  gggttctttt ccatagtcca aagaaacaga tcagctcttc agatattctg gactcagcag
4921  aagaattctc ggcaaaagtt gatatcgaag ttgacagccc aaaccctacg cccgttctta
4981  gaagtgtgag tctccgagca agagcaggaa tagctaggat ccatgctccc agggacttgc
5041  agacgatgca tttcttggcc aaagtggctt cctcaagaaa gcagcactta cctttgaaaa
5101  atgctgggaa cattgaagtt tatttggata tcaaggtccc agaacaagga agtcactttt
5161  cagtggatcc aaagaatcta ctccttaaac ctggagaaga acatgaggtt attgtttcat
5221  ttactccaaa ggatcctgaa gcctgcgagg aaaggatctt gaaaatattt gtgcagccat
5281  ttggacctca gtatgaggta gtgttaaaag gcgaagtcat ttcttcagga agtaaacctc
5341  tgtcacctgg accttgctta gatattccat cgattttgtc caacaaacaa tttctggctt
```

-continued

```
5401  ggggaggagt ccctctaggt agaacacagc ttcagaaact agctttaaga aataattctg
5461  catctacaac tcaacattta cgactgctta ttagaggaca agatcaggac tgctttcagc
5521  ttcagaacac ttttggttca gaacagcgat tgaccagtaa ctgtgagatc agaattcacc
5581  caaaggaaga cattttcatc tctgtattat ttgcacctac tcgattatct tgcatgttgg
5641  ctagactaga aatcaaacaa cttggaaatc gatcacaacc aggcattaag ttcacaatac
5701  ctttgtctgg atatggagga acaagcaatc ttattttgga aggcgttaaa aaattatctg
5761  acagttacat ggtaacagtg aatggcttag tacctggcaa agaaagtaaa attgtttttt
5821  ctgtccgcaa cactggctcc cgagcagctt tgttaaagc agtaggtttt aaggattctc
5881  agaaaaaagt tttgctggat cctaaagtat tgaggatttt tccagataaa tttgtactca
5941  aggaaagaac acaagaaaat gttactttaa tatataatcc atcagacaga ggaatcaata
6001  ataaaactgc aacagaacta tcaactgtat acttatttgg tggagatgaa atttcaagac
6061  agcagtatcg cagggccctg ttacataaac cagagatgat aaaacagata cttccagaac
6121  atagtgtgct tcaaaacatt aattttgttg aagcatttca agatgagcta ttagtaactg
6181  aagtatatga tcttccccaa cgacctaatg atgttcagct cttttatgga agcatgtgta
6241  aaattatact ttcagtaatt ggagaattca gagattgcat ttctagcaga gaattccttc
6301  agccttcttc caaagctagc ttggaatcta caagcgactt gggagcttct gggaaacatg
6361  gtggcaacgt ctctttggat gttttaccag tcaaaggtcc tcaggttct cctcttctct
6421  cacgggcggc tcgcccgcct ctggatcagc tggcctccga agagccgtgg actgtcctac
6481  ccgagcactt gattctgta gctccttctc cttgtgacat ggcaaaaact ggacgtttcc
6541  agattgtgaa taactctgtg aggttactga gatttgagct gtgctggcca gcgcattgcc
6601  tcacagtcac gccgcagcat ggatgtgtcg cgccagagag taaactacaa attcttgtga
6661  gtcctaattc ctccttatcc acaaaacagt caatgttccc gtggagtggt ttgatctata
6721  tacactgtga cgatggacag aagaaaattg tgaaagttca aattcgagaa gatttaactc
6781  aagtggaact tttaactcgt ttgacctcca aaccatttgg aattctttcc ccagtatctg
6841  agccttcagt tagtcatttg gtcaaaccaa tgacaaaacc gccttccaca aaagttgaaa
6901  taagaaacaa gagtattact tttcctacaa cagaacctgg tgaaacttca gagagctgtc
6961  tagaactcga gaatcatggc accacagacg tgaaatggca tctgtcatct ttagcgccac
7021  cttatgtcaa gggagttgat gaaagtggag atgtttttag agctacctat gcagcattca
7081  gatgttctcc tatttctggt ctgctggaaa gccatgggat ccaaaaagtc tccatcacat
7141  ttttgcccag aggtaggggg gattatgccc agttttggga tgttgaatgt caccctctta
7201  aggagcctca catgaaacac acgttgagat tccaactctc tggacaaagc atcgaagcag
7261  aaaatgagcc tgaaaacgca tgcctttcca cggattccct cattaaaata gatcatttag
7321  ttaagcccg aagacaagct gtgtcagagg cttctgctcg catacctgag cagcttgatg
7381  tgactgctcg tggagtttat gccccagagg atgtgtacag gttccggccg actagtgtgg
7441  gggaatcacg gacacttaaa gtcaatctgc gaaataattc ttttattaca cactcactga
7501  agtttttgag tcccagagag ccattctatg tcaaacattc caagtactct ttgagagccc
7561  agcattacat caacatgccc gtgcagttca aaccgaagtc cgcaggcaaa tttgaagctt
7621  tgcttgtcat tcaaacagat gaaggcaaga gtattgctat tcgactaatt ggtgaagctc
7681  ttggaaaaaa ttaactagaa tacatttttg tgtaaagtaa attacataag ttgtattttg
7741  ttaactttat cttttctacac tacaattatg cttttgtata tatattttgt atgatggata
7801  tctataattg tagattttgt ttttacaagc taatactgaa gactcgactg aaatattatg
```

```
7861    tatctagccc atagtattgt acttaacttt tacaggtgag aagagagttc tgtgtttgca 7921    ttgattatga tattctgaat aaatatggaa tatattttaa tgtggtatat ccagaaaaaa 7981    aaaaaaaaaa aaaaa
```

In an embodiment, Cep192 gene product comprises the following sequence (SEQ ID NO:4):

MEDFRGIAEESFPSFLTNSLFGNSGILENVTLSSNLGLPVAVST

LARDRSSTDNRYPDIQASYLVEGRFSVPSGSSPGSQSDAEPRERLQLSFQ

DDDSISRKKSYVESQRLSNALSKQSALQMETAGPEEEPAGATESLQGQDL

FNRASPLEQAQDSPIDFHLQSWMNNKEPKIVVLDAGKHFEDKTLKSDLSH

TSLLENEKLILPTSLEDSSDDDIDDEMFYDDHLEAYFEQLAIPGMIYEDL

EGPEPPEKGFKLPTNGLRQANENGSLNCKFQSENNSSLISLDSHSSETTH

KESEESQVICLPGTSNSIGTGDSRRYTDGMLPFSSGTWGTEKEIENLKGI

VPDLNSECASKDVLVKTLRAIDVKLNSDNFHDANANRGGFDLTDPVKQGA

ECPHQNKTVLHMDGCLDTETPTVSIQENVDVASLKPISDSGINFTDAIWS

PTCERRTCECHESIEKNKDKTDLPQSVVYQNEEGRWVTDLAYYTSFNSKQ

NLNVSLSDEMNEDFRSGSEAFDLIAQDEEEFNKEHQFIQEENIDAHNTSV

ALGDTSWGATINYSLLRKSRSTSDLDKDDASYLRLSLGEFFAQRSEALGC

LGGGNNVKRPSFGYFIRSPEKREPIALIRKSDVSRGNLEKEMAHLNHDLY

SGDLNEQSQAQLSEGSITLQVEAVESTSQVDENDVTLTADKGKTEDTFFM

SNKPQRYKDKLPDSGDSMLRISTIASATAEASVNTDPSQLAAMIKALSNK

TRDKTFQEDEKQKDYSHVRHFLPNDLEKSNGSNALDMEKYLKKTEVSRYE

SALENFSRASMSDTWDLSLPKEQTTQDIHPVDLSATSVSVRAPEENTAAI

VYVENGESENQESFRTINSSNSVTNRENNSAVVDVKTCSIDNKLQDVGND

EKATSISTPSDSYSSVRNPRITSLCLLKDCEEIRDNRENQRQNECVSEIS

NSEKHVTFENHRIVSPKNSDLKNTSPEHGGRGSEDEQESFRPSTSPLSHS

SPSEISGTSSSGCALESFGSAAQQQQPPCEQELSPLVCSPAGVSRLTYVS

EPESSYPTTATDDALEDRKSDITSELSTTIIQGSPAALEERAMEKLREKV

PFQNRGKGTLSSTIQNNSDTRKATETTSLSSKPEYVKPDFRWSKDPSSKS

GNLLETSEVGWTSNPEELDPIRLALLGKSGLSCQVGSATSHPVSCQEPID

EDQRISPKDKSTAGREFSGQVSHQTTSENQCTPIPSSTVHSSVADMQNMP

AAVHALLTQPSLSAAPFAQRYLGTLPSTGSTTLPQCHAGNATVCGFSGGL

PYPAVAGEPVQNSVAVGICLGSNIGSGWMGTSSLCNPYSNTLNQNLLSTT

KPFPVPSVGTNCGIEPWDSGVTSGLGSVRVPEELKLPHACCVGIASQTLL

SVLNPTDRWLQVSIGVLSISVNGEKVDLSTYRCLVFKNKATIRPHATEET

KVLFIPSSPGVFRCTFSVASWPCSTDAETTVQAEALASTVTLTATAESPV

IEVETEKKDVLDFGDLTYGGWKALPLKLINRTHATVPIRLIINANAVAWR

CFTFSKESVRAPVEVAPCADVVTRLAGPSVVNHMMPASYDGQDPEFLMIW

VLFHSPKKQISSSDILDSAEEFSAKVDTEVDSPNPTPVLRSVSLRARAGI

ARTHAPRDLQTMHFLAKVASSRKQHLPLKNAGNIEVYLDIKVPEQGSHFS

VDPKNLLLKPGEEHEVIVSFTPKDPEACEERLKIFVQPFGPQYEVVLKGE

VISSGSKPLSPGPCLDIPSILSNKQFLAWGGVPLGRTQLQKLALRNNSAS

TTQHLRLLIRGQDQDCFQLQNTFGSEQRLTSNCEIRTHPKEDIFISVLFA

PTRLSCMLARLEIKQLGNRSQPGIKFTIPLSGYGGTSNLILEGVKKLSDS

YMVTVNGLVPGKESKIVFSVRNTGSRAAFVKAVGFKDSQKKVLLDPKVLR

IFPDKFVLKERTQENVTLTYNPSDRGTNNKTATELSTVYLFGGDETSRQQ

YRRALLHKPEMIKQILPEHSVLQNINFVEAFQDELLVTEVYDLPQRPNDV

QLFYGSMCKIILSVIGEFRDCISSREFLQPSSKASLESTSDLGASGKHGG

NVSLDVLPVKGPQGSPLLSRAARPPLDQLASEEPWTVLPEHLILVAPSPC

DMAKTGRFQIVNNSVRLLRFELCWPAHCLTVTPQHGCVAPESKLQILVSP

NSSLSTKQSMFPWSGLIYIHCDDGQKKIVKVQIREDLTQVELLTRLTSKP

FGILSPVSEPSVSHLVKPMTKPPSTKVEIRNKSITFPTTEPGETSESCLE

LENHGTTDVKWHLSSLAPPYVKGVDESGDVFRATYAAFRCSPISGLLESH

GTQKVSITFLPRGRGDYAQFWDVECHPLKEPHMKHTLRFQLSGQSIEAEN

EPENACLSTDSLIKIDHLVKPRRQAVSEASARIPEQLDVTARGVYAPEDV

YRFRPTSVGESRTLKVNLRNNSFITHSLKFLSPREPFYVKHSKYSLRAQH

YINMPVQFKPKSAGKFEALLVTQTDEGKSIAIRLTGEALGKN

The phrase "and/or" as used herein, with option A and/or option B for example, encompasses the individual embodiments of (i) option A alone, (ii) option B alone, and (iii) option A plus option B.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group subjectly and all possible subgroups of the main group, but also the main group absent one or more of the group members. The present invention also envisages the explicit exclusion of one or more of any of the group members in the claimed invention.

All combinations of the various elements described herein are within the scope of the invention unless otherwise indicated herein or otherwise clearly contradicted by context.

In the event that one or more of the literature and similar materials incorporated by reference herein differs from or contradicts this application, including but not limited to defined terms, term usage, described techniques, or the like, this application controls.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Introduction

Cell motility is driven by a cycle of protrusion of the membrane at the cell front, adhesion of the protrusion to the substratum, contractility to move the cell body forward, and finally disadhesion at the rear. While the roles of the actin cytoskeleton in these events have been studied in detail (Ridley, Schwartz et al. 2003; Gardel, Schneider et al. 2010), much less is known about the specific contributions of microtubules. It is, however, clear that the microtubule cytoskeleton is required for the normal polarization and motility of many cell types and there is emerging evidence that it does so by exerting spatiotemporal control over actin dynamics/contractility and the delivery of membrane and signaling molecules to the cell periphery (Rodriguez, Schaefer et al. 2003; Small and Kaverina 2003; Watanabe, Noritake et al. 2005). Microtubules also contribute to cell migration by regulating the disassembly of focal adhesions (Broussard, Webb et al. 2008) (FAs). FAs are integrin-based macromolecular assemblies that link the actin cytoskeleton to extracellular matrix and thus anchor the cell to its substratum to provide traction for cell motility. The primary microtubule nucleating and organizing structure in the cell is the centrosome. Herein it is disclosed that Cep192 and Kif19 regulate the microtubule cytoskeleton.

While it would be difficult to raise the levels of a particular regulatory protein rapidly in relevant cells, it is far more tractable to lower the levels of a target protein through RNA interference (RNAi). The essence of this approach is to inhibit messenger RNA (mRNA) from coding for the synthesis of a target protein. There are various types of RNAi, such as plasmid-driven shRNA, which has the advantage of being targetable to certain cell populations and is generally long-lasting in terms of suppression of protein expression. shRNA generally requires a specialized transfection technique such as viral entry or electroporation. Small interfering RNAs (siRNAs) do not involve the use of a plasmid, are tiny and hence can more readily be introduced into cells, and offer more flexibility in terms of target sequences. siRNA can be handled and treated much like a drug and theoretically can interfere with the translation of almost any mRNA as long as the mRNA has a distinctive sequence. Therefore, siRNA has far broader flexibility than traditional drugs. A key to capitalizing on the therapeutic benefits of siRNA lies in effective delivery systems. Carriers such as nanoparticles have now become the approach of choice. Nanotechnology is broadly considered the study of manipulations of materials at the nanometer scale, roughly 1 to 500 nm. Materials at this scale possess a higher surface to volume ratio and, as a result, their physical properties tend to be different from materials at the macro or micro scale. Novel properties that result from such modifications have led to applications in fields such as catalysis, microelectronics, robotics and medicine. The medical and biological applications are particularly interesting because most biochemical processes, especially those involving macromolecules, occur at the lower end of the nano scale. Nanotechnology, therefore, holds the promise of being able to duplicate biochemical processes and directly alter these processes using man-made materials. With the progress of material synthesis and the rise of nanotechnology, the generation of nanomaterials with specific functions has become possible. In to, for example, solid tumors in humans.

To date, the reported liposomal and other nanoparticle based delivery vehicles for siRNA have involved systemic delivery. In contrast, a novel delivery approach disclosed herein is effective for both topical and systemic applications. One preferred embodiment of the platform is based on a hydrogel/sugar glass composite, or hybrid nanoparticle platform capable of encapsulating and controllably releasing a broad range of therapeutically relevant materials ranging from gaseous nitric oxide to peptides to larger macromolecules such as chemotherapeutic agents and phosphodiesterase inhibitors. The versatility of this biocompatible and nontoxic platform has been shown in pre-clinical studies demonstrating: i) topical efficacy in clearing both Gram positive and negative cutaneous wound infections, accelerating wound healing, and promoting erectile activity; and ii) systemic efficacy in modulating cardiovascular parameters.

The data herein indicates that kif19 and Cep192 proteins exert profound regulatory control over the motility and/or growth characteristics of key cells required for wound closure, re-vascularization and re-innervation. Each protein can be targeted independently by different np-si to control a distinct aspect of the wound healing cascade. The nanoparticle platform can be very effective as a topical delivery vehicle for the siRNA. The preferred therapeutic platform technology is nanoparticle-encapsulated siRNAs (np-si) targeting the expression of CEP192 and KIF19 genes encoding regulators of the microtubule cytoskeleton. Without being bound be theory, it is understood that Kif19 np-si treatments inhibit fibroblast motility to reduce fibrosis/scarring. The Cep192 np-si treatment does similar, but also inhibits axonal growth to ameliorate the pain that results from premature axon sprouting into wounded tissue.

The nanoparticle delivery system bypasses pitfalls typically associated with therapeutic siRNA—for example, the ability to deliver therapeutic levels of siRNA to enhance the closure of surface wounds in vivo.

Example 1

Kif19 normally promotes cell motility by stimulating the disassembly of integrin-based adhesion complexes that link cells to the underlying extracellular matrix. siRNA-mediated depletion of Kif19 inhibits 1) cancer cell motility in vitro; 2) matrigel invasion of primary tumor cells ex vivo, 3) and movement of cells into excision wounds in mice.

Figure 2:
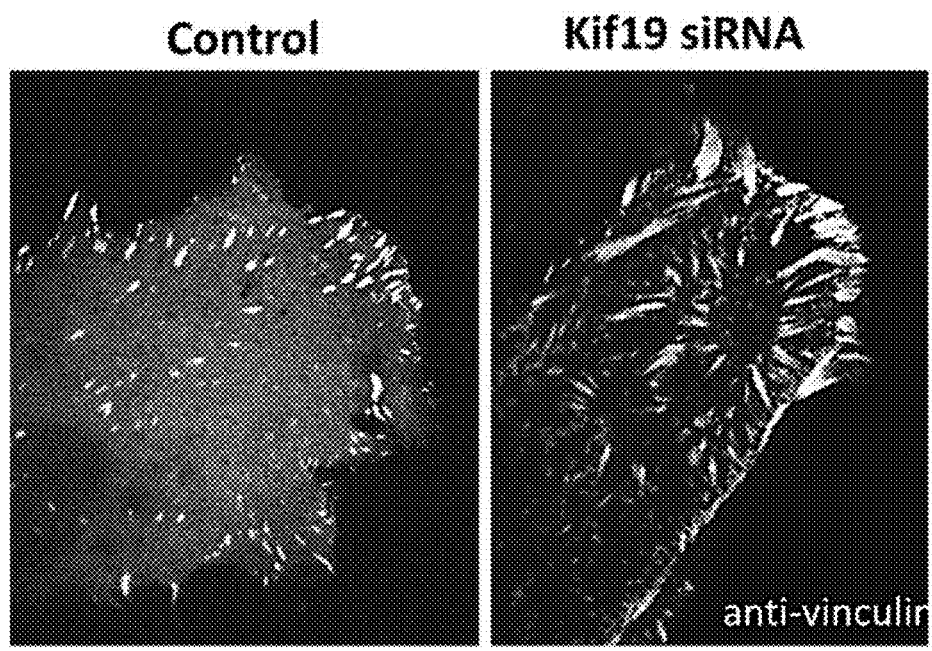
FIG. 2: The images show regions of U2OS cells (human Osteosarcoma) immunostained for the focal adhesion protein vinculin. The depletion of Kif19 by siRNA induces a substantial increase in the size and number of focal adhesions particularly in the cell interior.
Figure 3A:
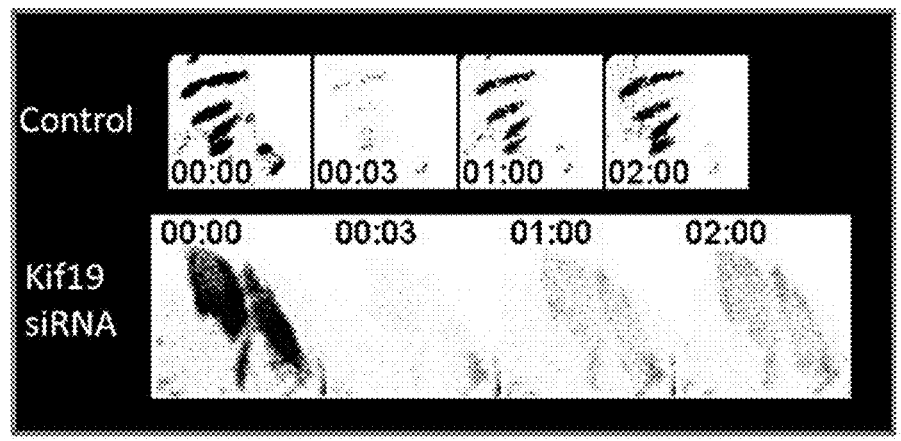
FIG. 3A-3C: Panel A shows fluorescence recovery after photobleaching (FRAP) of GFP-vinculin labeled focal adhesions from control and Kif19 siRNA-treated U2OS cells. Time is shown in minutes: seconds. Panel B shows a representative fluorescence recovery plot from each condition. Panel C plots the density of focal adhesions in untreated cells (pre) and at various time points after nocodazole washout. Repolymerization of MTs after nocodazole washout was previously shown to stimulate focal adhesion disassembly (Ezratty, Partridge et al. 2005). The depletion of Kif19 prevents the disassembly of focal adhesions after nocodazole washout.
Figure 3B:
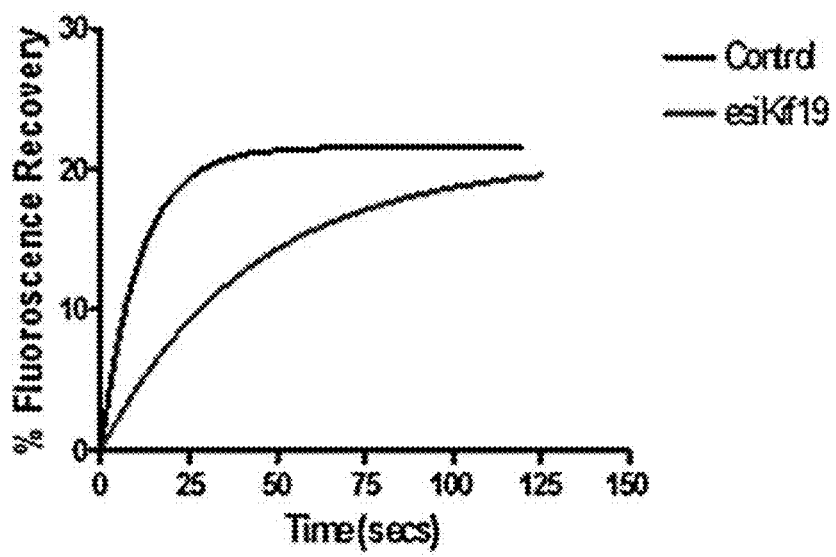
Figure 3C:
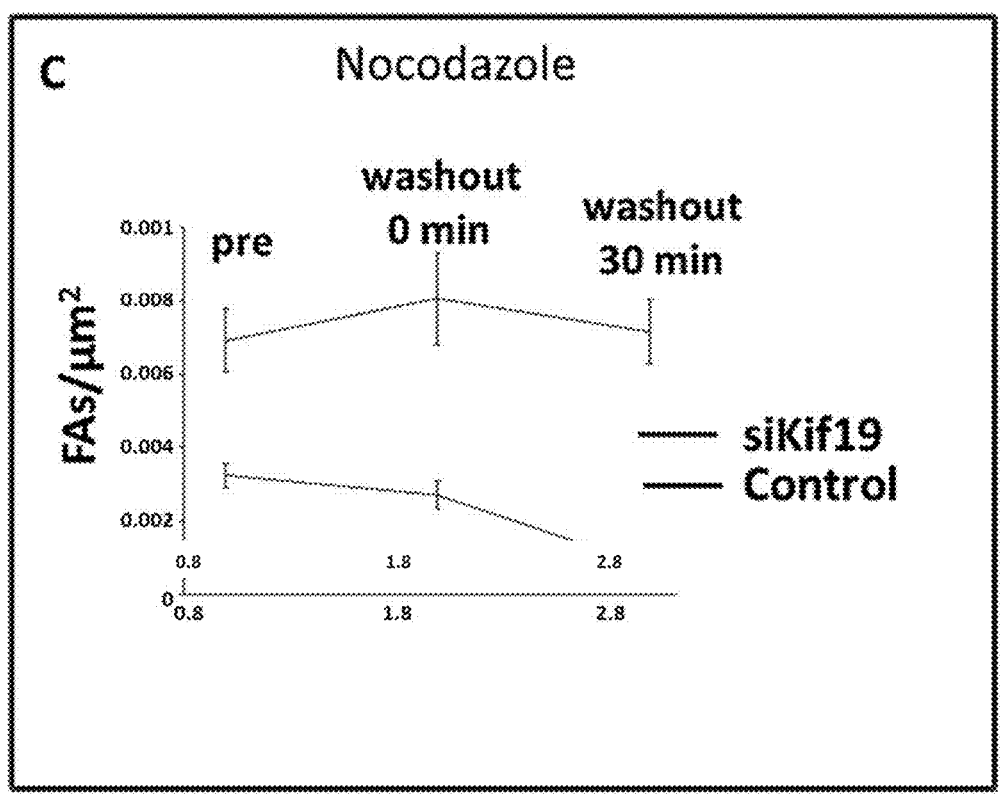

FIG. 1 shows a confocal micrograph showing a human U2OS cell double labeled for Kif19 and the FA protein, vinculin. The far right panel is a higher magnification of the region boxed in "merge". As shown in FIGS. 2 and 3, the depletion of Kif19 from tissue culture cells induces an increase in focal adhesion size and stability. FIG. 2 shows regions of U2OS cells (human Osteosarcoma) immunostained for the focal adhesion protein vinculin. The depletion of Kif19 by siRNA induces a substantial increase in the size and number of focal adhesions particularly in the cell interior. A time series was obtained showing the assembly/disassembly dynamics of focal adhesions in GFP-vinculin expressing control and Kif19 siRNA-treated U2OS cells. In FIG. 3, panel A shows fluorescence recovery after photobleaching (FRAP) of GFP-vinculin labeled focal adhesions from control and Kif19 siRNA-treated U2OS cells. Panel B shows a representative fluorescence recovery plot from each condition. Panel C plots the density of focal adhesions in untreated cells (pre) and at various time points after nocodazole washout. Repolymerization of MTs after nocodazole washout was previously shown to stimulate focal adhesion disassembly (Ezratty, Partridge et al. 2005). The depletion of Kif19 prevents the disassembly of focal adhesions after nocodazole washout. The siRNA sequences used for Kif19 are as follows:

```
                                            (SEQ ID NO: 5)
        5'-GGAAGUAAGCUCAGGAUCUCAGCAG-3'

(SEQ ID NO: 6)
        5'-GUCCUUCAUUCGAGUCCUAUAGUCGUC-3'.
```

Figure 4:
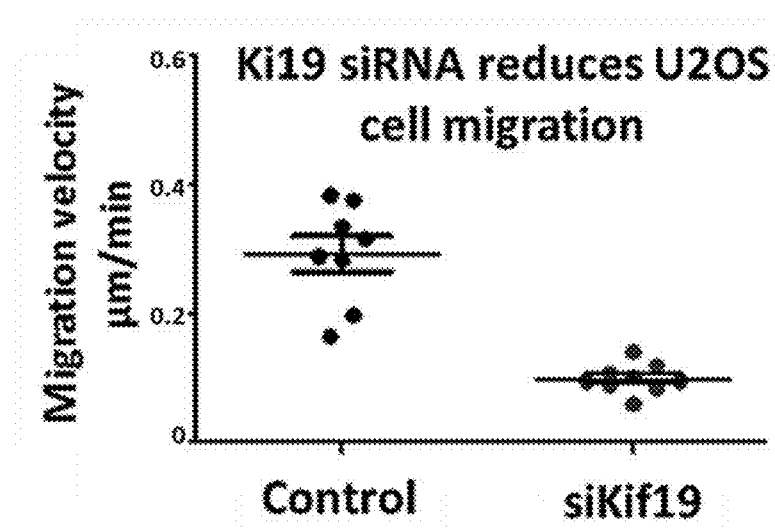
FIG. 4: Shows siRNA depletion of Kif19 decreases the motility of cancer cells in vitro.
Figure 5:
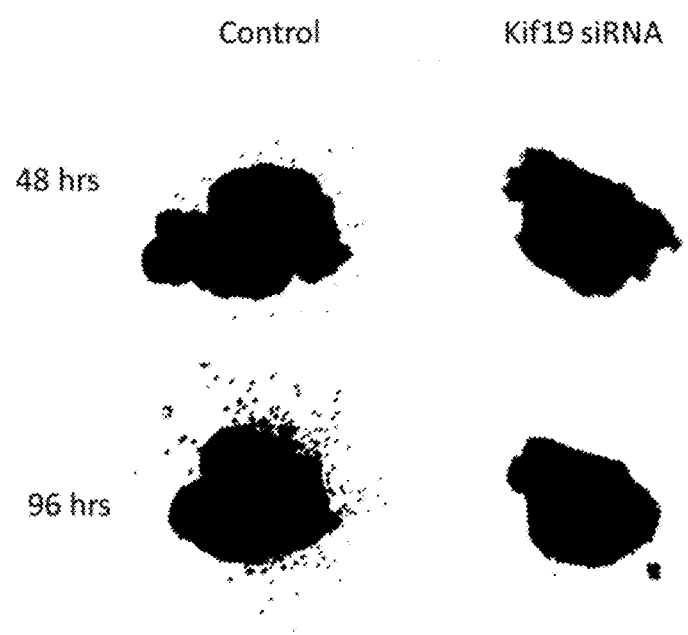
FIG. 5: Shows an anaplastic thyroid carcinoma mouse model (Arciuch et al., Oncotarget, December 2011). Dissociated tumor is removed from mouse and bathed in nanoparticles containing control or Kif19 siRNA for 2-24 hrs. Tumors are then embedded in matrigel and imaged daily. Movement of cells from tumor into matrigel is considered invasion. Black dots moving away from the dark central mass are invasive tumor cells. Kif19 nanoparticle siRNA treatment reduces tumor cell invasion relative to controls.

FIG. 4 shows siRNA depletion of Kif19 decreases the motility of cancer cells in vitro. Depletion of Kif19 prevents tumor cell invasion from anaplastic thyroid carcinomas embedded in matrigel. FIG. 5 shows an anaplastic thyroid carcinoma mouse model (Archiuch, Rousseau et al, Oncotarget, December 2011). Accounts for 40% of all thyroid cancer deaths and extremely metastatic. Nearly 100% lethality, median survival 4 months. Currently not treatable. Dissociated tumor is removed from mouse and bathed in nanoparticles containing control or Kif19 siRNA for 2-24 hrs. Tumors are then embedded in matrigel and imaged daily. Movement of cells from tumor into matrigel is considered invasion. Black dots moving away from the dark central mass are invasive tumor cells. Kif19 nanoparticle siRNA treatment reduces tumor cell invasion relative to controls.

Depletion of Kif19 was later confirmed to inhibit cell movement into mouse full thickness biopsy wounds as compared to control.

Figure 6:
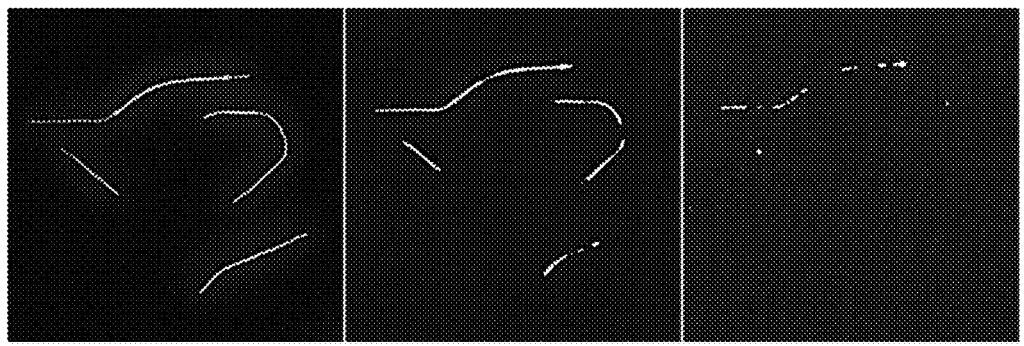
FIG. 6: Time-series of TIRF images showing a field of fluorescently-labeled taxol-stabilized microtubules incubated with purified recombinant full-length Kif19. The time from the first to last image is 5 minutes.
Figure 7A:
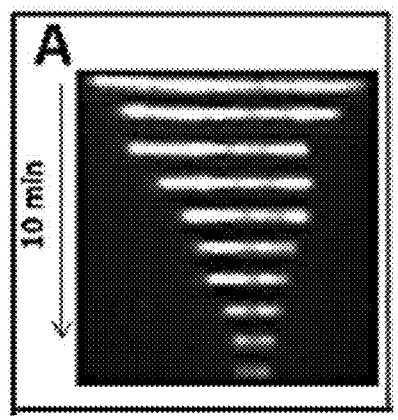
FIG. 7A-7F: Kif19 is a microtubule depolymerase that localizes to substrate adhesions and promotes cell motility. A) Time series images of a fluorescent microtubule incubated with purified recombinant Kif19. B) Immunofluorescence showing the co-localization of Kif19 with the focal adhesion protein, vinculin. C) High magnification image showing a region of a cell double-labeled for Kif19 and microtubules. Microtubules often terminate at kif19-labeled substrate adhesions and these interactions are believed to control adhesion turnover rate. D) Control and Kif19 siRNA treated human U2OS cells labeled for the focal adhesion marker, vinculin. In cells depleted of Kif19, adhesions become significantly enlarged and hyperstable. E) Measured rates of in vitro wound closure in control and Kif19 siRNA-treated cultures (scratch assay). F) Movement trajectories of control and Kif19 siRNA-treated cells plotted from a common origin. The loss of Kif19 nearly completely suppresses cell movement.
Figure 7B:
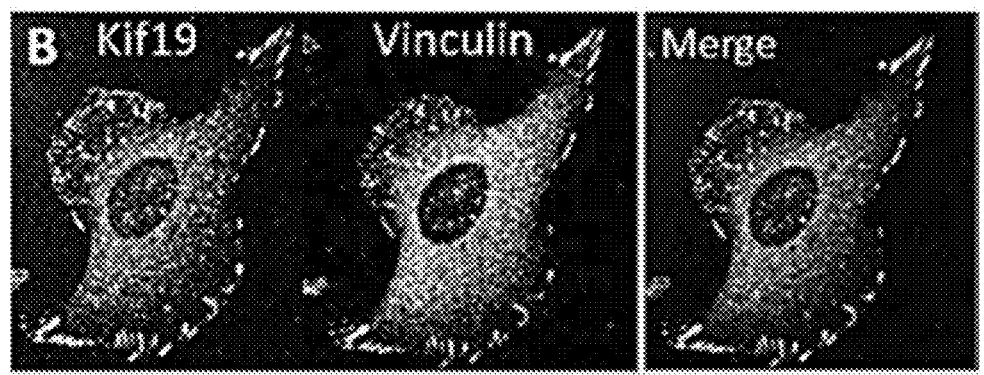
Figure 7C:
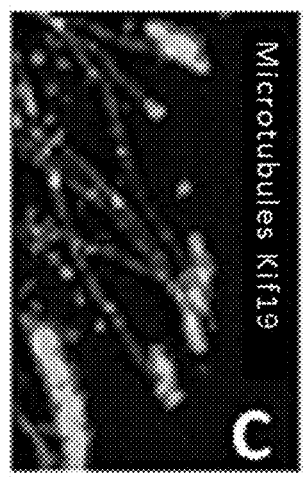
Figure 7D:
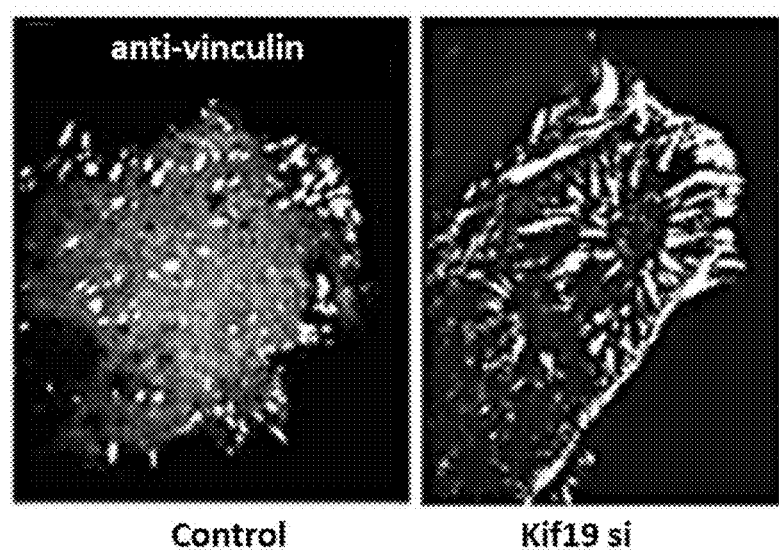
Figure 7E:
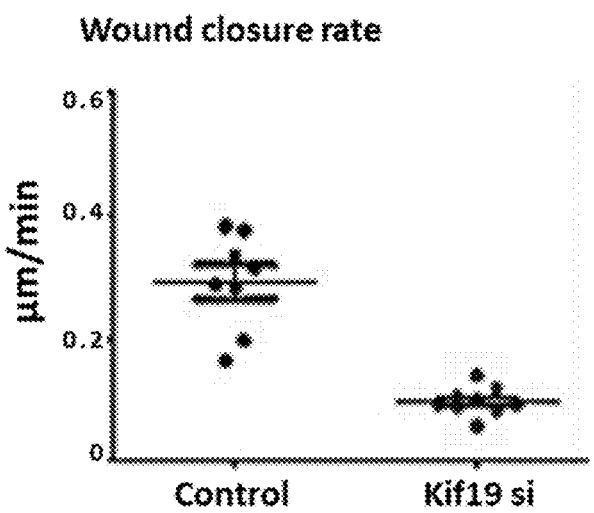
Figure 7F:
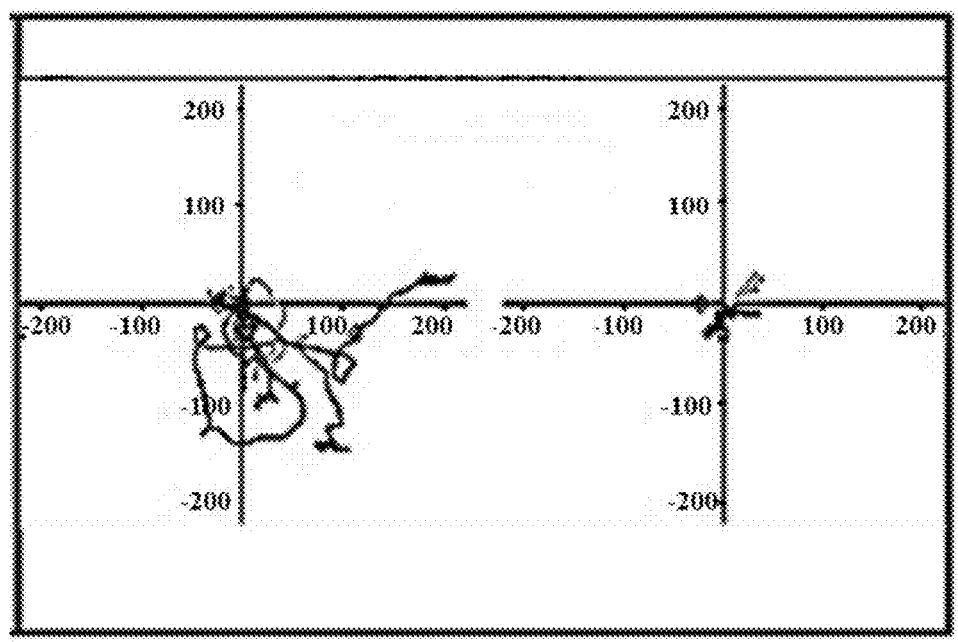

Kif-19 depolymerizes microtubules in vitro, as shown in FIG. 6 where a time-series of TIRF images shows a field of fluorescently-labeled taxol-stabilized microtubules incubated with purified recombinant full-length Kif19. The time from the first to last image is 5 minutes.

In summary, Kif19 is a microtubule depolymerizing enzyme in vitro that localizes to and stimulates the turnover of substrate adhesions in cells (FIG. 7A-D). siRNA depletion of Kif19 in human epithelial and fibroblast cell models nearly completely suppresses cell motility likely because these cells become too tightly attached to their underlying substratum. Kif19 is the first and, at present, only microtubule regulatory protein known to be housed within the substrate adhesion complex. Agents that suppress Kif19, such as Kif19 siRNA nanoparticles, can be used as a means to prevent fibrosis/scarring later in the wound healing process.

Example 2

Cep192 promotes cell motility via the nucleation of centrosomal microtubules. Cep192 is a centrosomal scaffolding protein required for the nucleation of microtubules from centrosomes. siRNA-mediated depletion of Cep192 inhibits 1) the motility of cancer cells and primary human keratinocytes in vitro; 2) matrigel invasion of primary tumor cells ex vivo; 3) axon outgrowth from primary neurons. This additionally identifies Cep192, over Kif19, as a therapeutic target for mitigation of pain after wounding.

The centrosome is an organelle that serves as the main microtubule organizing center (MTOC) of the animal cell as well as a regulator of cell-cycle progression. Centrosomes are composed of two orthogonally arranged centrioles surrounded by an amorphous mass of protein termed the pericentriolar material (PCM). The PCM contains proteins responsible for microtubule nucleation and anchoring.

Cep192 is a centrosome scaffolding protein required for centrosomal microtubule nucleation during mitosis (Gomez-Ferreria, Rath et al. 2007; Gomez-Ferreria and Sharp 2008). Disclosed herein is that Cep192 is also required for the nucleation of centrosomal microtubules in interphase cells. Depletion of Cep192 strongly suppresses the motility of both cancer and skin cells and thus Cep192 is a novel target for anti-metastatic and anti-fibrotic therapeutics. Additionally, depletion of Cep192 inhibits axon outgrowth from primary adult rat dorsal root ganglion neurons. Thus, Cep192 can also be targeted to suppress excessive early axon sprouting known to be associated with pain.

Figure 8:
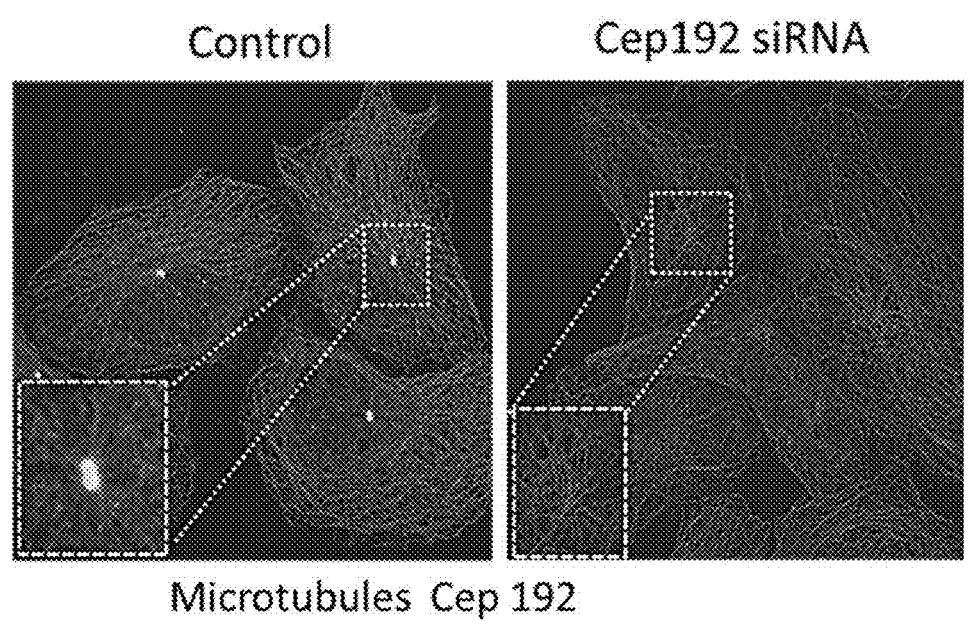
FIG. 8: Confocal micrographs showing control and Cep192 siRNA-treated U2OS cells immunolabeled for microtubules (red) and Cep192 (green). Cep192 siRNA treatment eliminates Cep192 immunofluorescence indicating a strong protein knockdown. Controls showed robust centrosomes with radial MT arrays while Cep192-depleted cells contained non-radial MT arrangements. Inset shows higher magnification of boxed region.
Figure 9A:
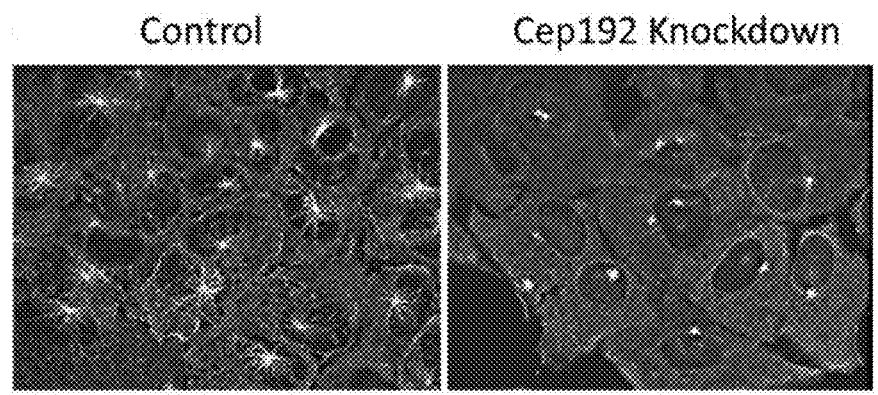
FIG. 9A-B: U2OS cells were treated with siRNA for 72 hours then exposed to 5 uM nocodazole for 1 hour to depolymerize microtubules. Cells were then washed 3× with warm DMEM and then incubated for 10 minutes to allow microtubule regrowth. Images show control and Cep192 siRNA treated cells stained for microtubules. B) Control cells showed a significantly higher amount of regrowth from the centrosome than did cells depleted of Cep192; P<0.0001. S.E.M. is depicted as vertical bars.
Figure 9B:
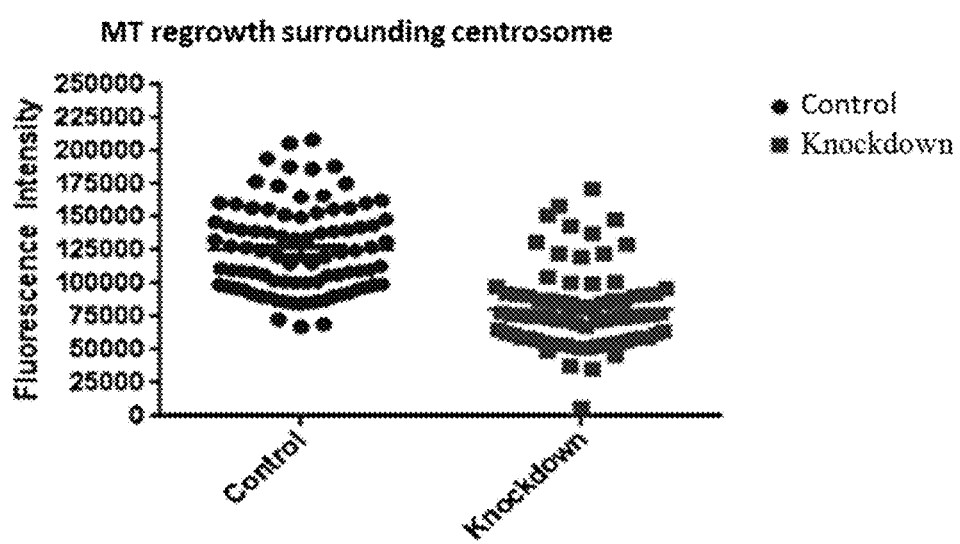

Cep192 is found to localize to centrosomes in interphase cells and is required for normal microtubule organization (see FIG. 8). Cep192 was also found to stimulate microtubule nucleation from centrosomes (FIG. 9).

Figures 10A, 10B, 10C, 10D:
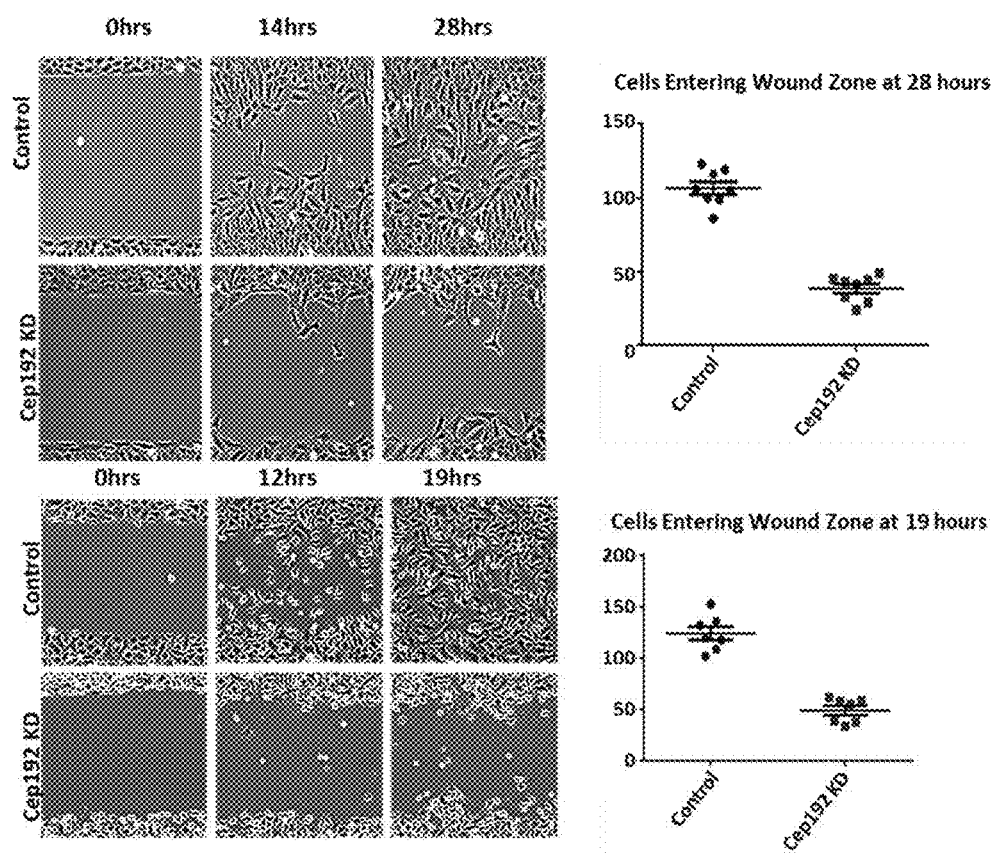
FIG. 10A-10D: A) Time-lapse phase-contrast images of control and Cep192 siRNA treated U2OS cells from an in vitro wound healing assay. U2OS cells were plated into Ibidi Culture-Insert dishes following knockdown. B) Significantly fewer Cep192 depleted cells entered the wound zone relative to controls. P<0.0001. S.E.M. is depicted as vertical bars. C) Time-lapse phase-contrast images of control and Cep192 siRNA-treated HEKa (human epidermal keratinocytes—adult) cells from an in vitro wound healing assay. HEKa cells were plated into Ibidi Culture-Insert dishes following. D) Significantly fewer Cep192-depleted cells entered the wound zone relative to controls. P<0.0001. S.E.M. is depicted as vertical bars.

It was found that Cep192 is required for normal cell motility in vitro. FIG. 10 shows in 10A) time-lapse phase-contrast images of control and Cep192 siRNA treated U2OS cells from an in vitro wound healing assay. U2OS cells were plated into Ibidi Culture-Insert dishes following knockdown. In 10B), significantly fewer Cep192 depleted cells entered the wound zone relative to controls. P<0.0001. S.E.M. is depicted as vertical bars. FIG. 10C) shows time-lapse phase-contrast images of control and Cep192 siRNA treated HEKa (human epidermal keratinoctyes—adult) cells from an in vitro a wound healing assay. HEKa cells were plated into Ibidi Culture-Insert dishes following. 10D) Shows significantly fewer Cep192 depleted cells entered the wound zone relative to controls. P<0.0001. S.E.M. is depicted as vertical bars. The siRNA sequences used for Sep192 are as follows:

```
                                            (SEQ ID NO: 7)
        5'-CACAUGAUGCCUGCUAGUU-3'

(SEQ ID NO: 8)
        5'-GACACUUUCUUCAUGAGCA-3'

(SEQ ID NO: 9)
        5'-GGACUUAAGUGCUACUAGU-3'.
```

Figure 11:
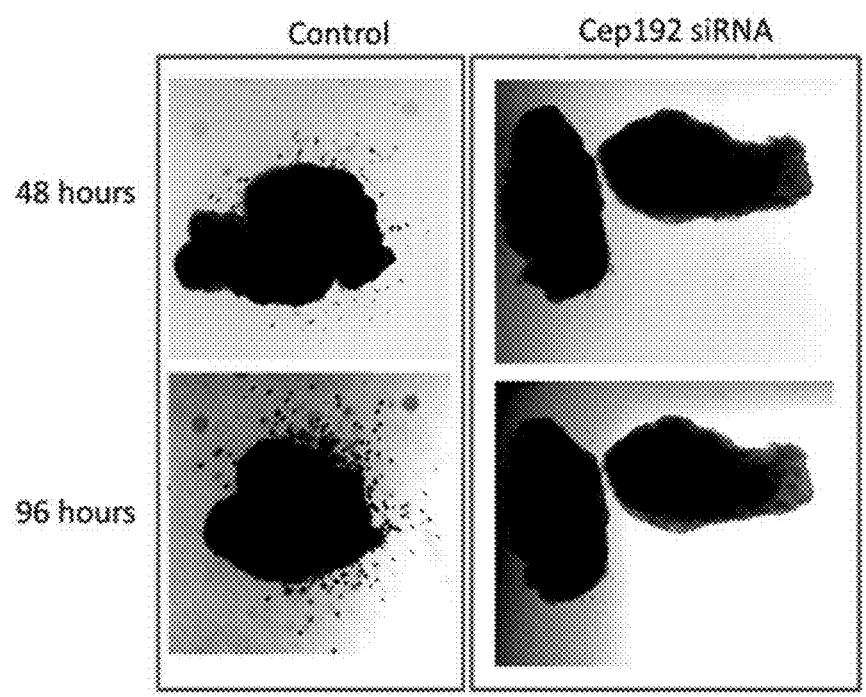
FIG. 11: Anaplastic thyroid carcinoma invasion assay: a dissociated tumor is removed from mouse and bathed in nanoparticles for 2 hrs. (48 hours) (top Panels). The tumor is embedded in Matrigel/Collagen matrix and imaged daily (96 hours) (bottom panels).
Figure 12:
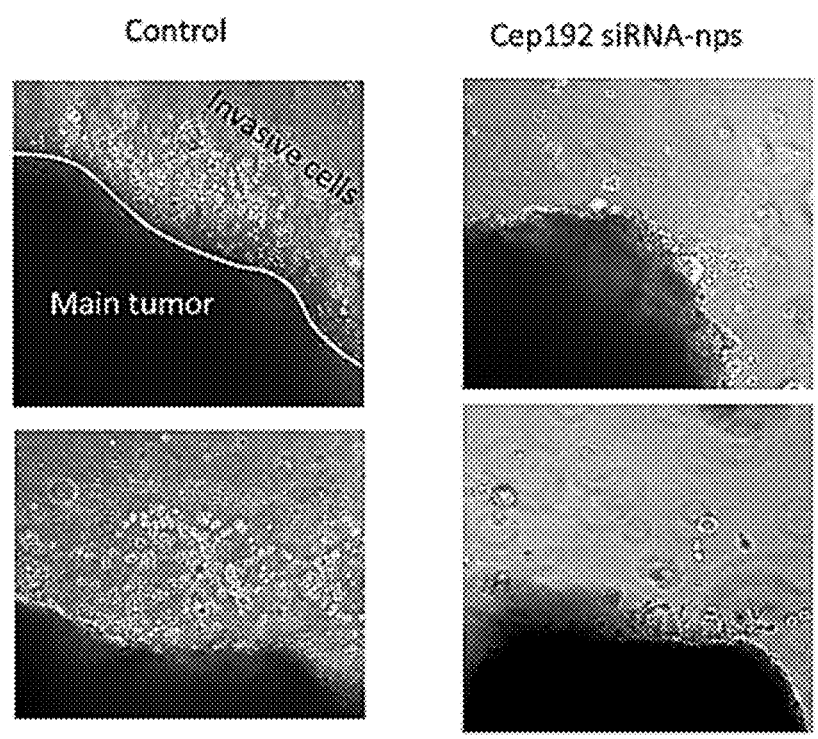
FIG. 12: Human large cell lung tumors. SC injection of human H460 lung cancer cells into mice (top panels). Invasive tumors (1-2 cm) removed and bathed in nanoparticles for 2 hrs. (middle panels). Tumor embedded in Matrigel/Collagen matrix and imaged daily (bottom panels).

Depletion of Cep192 prevents tumor cell invasion and metastasis. The effects on anaplastic thyroid carcinoma are shown in FIG. 11 and the effects on large cell lung tumor are shown in FIG. 12.

Figure 13:
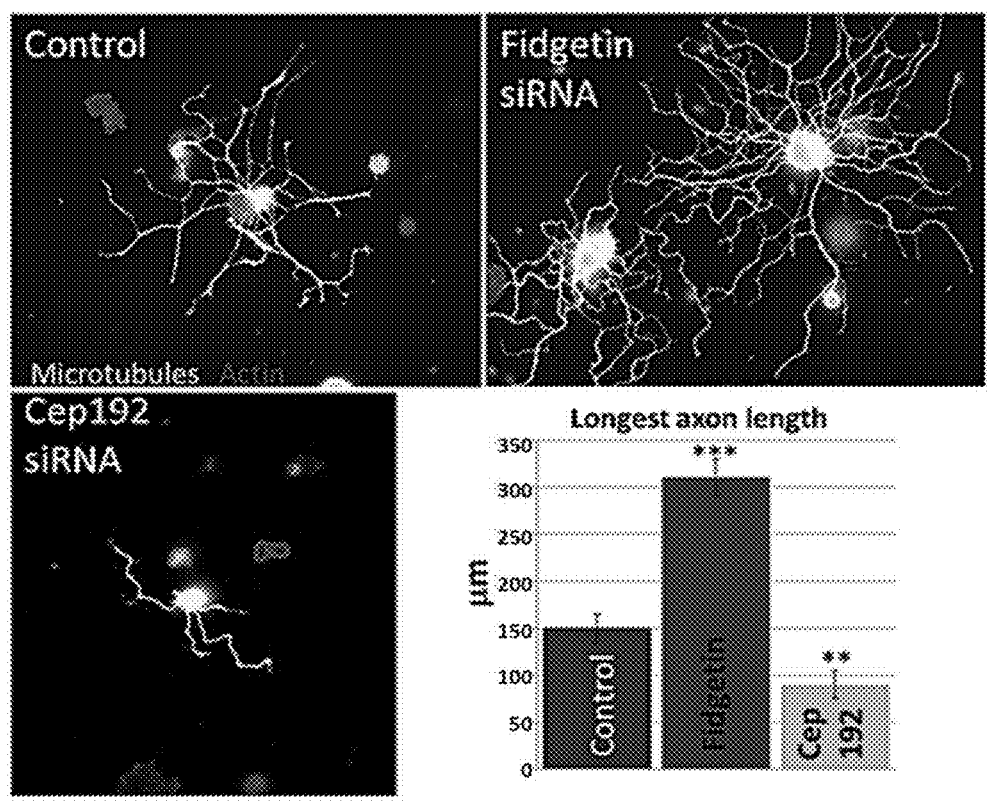
FIG. 13: Fidgetin and Cep192 regulate axon regeneration. Images are immunofluorescence micrographs of primary adult rat DRG neurons treated with control, Fidgetin or Cep192 nanoparticle encapsulated siRNA. Cells were fixed 24 hours after plating and siRNA treatment. Bottom right panel shows the average axon length in each condition (longest process from each individual cell was measured; error bars are SEM). *P<0.01; P<0.05.

Depletion of Cep192 inhibits axon outgrowth from primary rat neurons. FIG. 13 shows fidgetin and Cep192 regulate axon regeneration. Images are immunofluorescence micrographs of primary adult rat DRG neurons treated with control, Fidgetin or Cep192 nanoparticle encapsulated siRNA. Cells were fixed 24 hours after plating and siRNA treatment. Bottom right panel shows the average axon length in each condition (longest process from each individual cell was measured; error bars are SEM). *P<0.01; P<0.05. In contrast to Fidgetin np-si, Cep192 np-si treatments suppress axon regrowth in adult DRG neurons—Cep192 and Fidgetin are likely functionally antagonistic in this regard. Agents that suppress Cep192, such as Cep192 np-si, can be used to suppress excessive early axon sprouting known to be associated with pain.

Example 3

Figure 14:
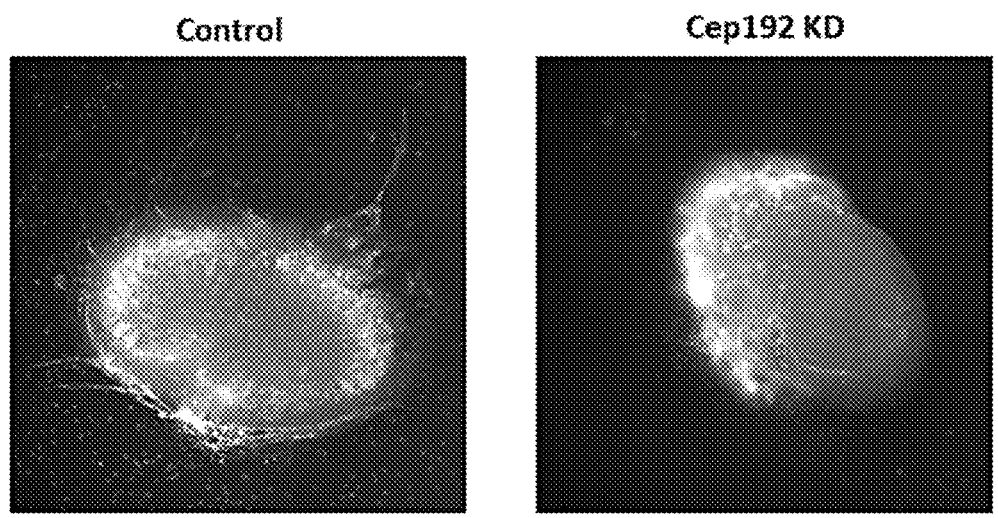
FIG. 14: Angiogenesis of fetal hearts 48 hours after treatment—Images show representative control and Cep192 siRNA treated hearts two days after siRNA treatment. In the control, migrating endocaridal cells have penetrated the ventricular wall and formed a fine vascular network. By contrast, Cep192 siRNA treated hearts have no apparent vessels at this same time point. Thus, the depletion of Cep192 dramatically inhibits the angiogenic process by the endocardial cells.

Angiogenesis of fetal hearts 48 hours after treatment: As shown in FIG. 14, Cep192 siRNA-treated hearts two days after siRNA treatment have no apparent vessels. In the control, however, migrating endocaridal cells have penetrated the ventricular wall and formed a fine vascular network. Thus, the depletion of Cep192 dramatically inhibits the angiogenic process by the endocardial cells.

Methods

Np-si application for experiments: This can be performed by mixing the nanoparticles in either sterile saline or water to achieve the targeted concentration in no more than 10 ul aliquots. The solution is applied directly to the wound, or target area, where it is rapidly absorbed. Controls include i) non-specific siRNA nanoparticles and ii) water or saline alone. Two different treatment regimens are exemplified here: In regimen 1, np-si are administered daily beginning 30 minutes after wounding though day 8. In regimen 2, np-si are administered every other day beginning 30 minutes after wounding (day 0, 2, 4, 6, and 8).

Np-si formulation. For the nanoparticles a hydrogel-based nanoparticle platform is used. A final concentration of siRNA of 0.30 to 0.35 nmole per mg of dry nanoparticles is used in studies. siRNAs are anionic but cationic stabilization is preferred for nanoparticle encapsulation and siRNA stability. In an embodiment, the formulation utilizes the cationic polysaccharide chitosan as a stabilizing factor for the siRNA. The cationic character of the nanoparticles can be enhanced by doping the formulation with varying amounts of positively charged amino silanes.

PEGylation of the np-si: Increasing the size of PEG molecules incorporated into the formulation may increase the rate of release for siRNA (this is determined using fluorescent labeled siRNA). Post-preparative PEGylaton of the np-si can be means of further minimizing aggregation and improving in vivo lifetime. In an embodiment, the conjugation of functionalized PEG chains (PEG-500/PEG-3000/PEG-5000) to the surface of np-si in alcohol/water medium to minimize the leakage of siRNA from the particles is effected.

Wound healing determination: Photographs of the wounds are taken daily to follow gross visual wound healing as assessed by the area of the wound uncovered by the migrating epithelia. Each wound is measured daily using a caliper and the area is determined.

Morphometric analysis of wound sections: Wound re-epithelialization is measured in Hematoxylin and Eosin stained sections from the center of the wound. The distance between the wound edges, defined by the distance between the first hair follicle encountered at each end of the wound, and the distance that the epithelium had traversed into the wound, is analyzed using ImageJ. The percentage of re-epithelialization [(distance traversed by epithelium)/(distance between wound edges)×100] is calculated and averaged for two sections per wound.

Collagen deposition: Staining is performed using Masson's trichrome stain and the percentage of blue collagen-stained area relative to the total area of the wound bed after taking digital images. This is quantified by counting the number of pixels staining above a threshold intensity and normalizing to the total number of pixels.

Proliferation rate. To visualize cell proliferation, mice are injected intrapertonially (120 mg/kg BrdU (Sigma-Aldrich, USA)) 2-4 hrs. prior to sacrifice and cutaneous wounds are harvested for paraffin embedding and BrdU immunohistochemistry. Tissue sections will be deparaffinized and rehydrated through graded alcohols and incubated overnight at room temperature with a biotinylated monoclonal BrdU antibody (Zymed, South Francisco, Calif.).

Nuclear staining are visualized using Streptavidin-peroxidase and diaminobenzidine (DAB) and samples will be lightly counterstained with hematoxylin. Wound tissue from mice that were not injected with BrdU is used as a negative control. Digital photographs are taken at high (40-60×) magnification (Zeiss AxioHOME microscope) and epithelial cells sections are examined using ImageJ software and classified as BrdU positive if they grossly demonstrated brown-stained nuclei from DAB staining or as BrdU negative if they were blue stained. nuclei. The proliferation rate is then calculated as the percentage of BrdU positive cells over the total number of cells within the ROI.

Angiogenesis: Wound sections are stained using CD31 antibody (also called platelet-derived endothelial cell adhesion molecule-1). Digital images at 40× magnification covering the majority of the wound bed are taken and the percent area stained in each image are quantified by counting the number of pixels staining above a threshold intensity and normalizing to the total number of pixels. Threshold intensity will be set such that only clearly stained pixels are counted. Staining identified as artifact, large vessels, and areas deemed to be outside the wound bed will be excluded.

Reinnervation: Wound sections post injury days 7 and 14 will be stained for protein gene product 9.5 (PGP9.5), a pan-neuronal marker, and the sensory neuropeptides calcitonin gene related peptide (CGRP) and substance P (SP). Nerve fiber growth into the wounds is compared between control and treated wounds, Histopathology of epidermal stem cells and the stem cell niche at the hair bulge. For identification of epidermal stem cells in various cohorts of animals, immunohistochemistry is performed for the following markers of epidermal stem cells-CD34, Cytokeratin 15, Bmi1, Lrig1, Blimp1, Nestin, Lgr5, CD-200, β1-Integrin, according to published reports. The epidermal stem cell niche is characterized by immunohistochemistry for α-smooth muscle actin (α-SMA) to detect epidermal myofibroblast and vascular smooth muscle cells, ICAM-1 for endothelial cells, F4/80 for macrophages.

Methods for angiogenesis experiments: Hearts were dissected from embryonic day (E) 11.5 Nfatc1-Cre;eGFP embryos, bathed 2 hours with siRNA and placed onto a 3D matrigel supplement with 10 ng/ml VEGF-A. Images (e.g. see FIG. 14) were then taken every day to record the coronary angiogenesis by eGFP marked endocardial cells.

REFERENCES

Arciuch et al., "Thyrocyte-specific inactivation of p53 and Pten results in anaplastic thyroid carcinomas faithfully recapitulating human tumors," Oncogene, Vol 2, No 12: 1109-1126 (2011).

Broussard, J. A., D. J. Webb, et al. (2008). "Asymmetric focal adhesion disassembly in motile cells." Curr Opin Cell Biol 20(1): 85-90.

Efimov, A. and I. Kaverina (2009). "Significance of microtubule catastrophes at focal adhesion sites." Cell Adh Migr 3(3): 285-287.

Efimov, A., N. Schiefermeier, et al. (2008). "Paxillin-dependent stimulation of microtubule catastrophes at focal adhesion sites." J Cell Sci 121(Pt 2): 196-204.

Ezratty, E. J., M. A. Partridge, et al. (2005). "Microtubule-induced focal adhesion disassembly is mediated by dynamin and focal adhesion kinase." Nat Cell Biol 7(6): 581-590.

Gardel, M. L., I. C. Schneider, et al. (2010). "Mechanical integration of actin and adhesion dynamics in cell migration." Annu Rev Cell Dev Biol 26: 315-333.

Gomez-Ferreria, M. A., U. Rath, et al. (2007). "Human Cep192 is required for mitotic centrosome and spindle assembly." Current biology: CB 17(22): 1960-1966.

Gomez-Ferreria, M. A. and D. J. Sharp (2008). "Cep192 and the generation of the mitotic spindle." Cell cycle 7(11): 1507-1510.

Ridley, A. J., M. A. Schwartz, et al. (2003). "Cell migration: integrating signals from front to back." Science 302 (5651): 1704-1709.

Rodriguez, O. C., A. W. Schaefer, et al. (2003). "Conserved microtubule-actin interactions in cell movement and morphogenesis." Nat Cell Biol 5(7): 599-609.

Small, J. V. and I. Kaverina (2003). "Microtubules meet substrate adhesions to arrange cell polarity." Curr Opin Cell Biol 15(1): 40-47.

Watanabe, T., J. Noritake, et al. (2005). "Regulation of microtubules in cell migration." Trends Cell Biol 15(2): 76-83.

What is claimed is:

1. A method of treating metastasis or inhibiting metastasis in a subject having anaplastic thyroid carcinoma or large lung cell cancer or osteosarcoma comprising administering to the subject an amount of an inhibitor of CEP192 effective to treat metastasis or inhibit metastasis of anaplastic thyroid carcinoma or large lung cell cancer or osteosarcoma, respectively, wherein the inhibitor of CEP192 is a siRNA directed to CEP192 or a shRNA directed to CEP192.

2. A method of treating fibrosis or scarring, or inhibiting fibrosis or scarring, in a subject comprising administering to the subject an amount of an inhibitor of CEP192 effective to treat fibrosis or scarring, or inhibit fibrosis or scarring, wherein the inhibitor of CEP192 is a siRNA directed to CEP192 or a shRNA directed to CEP192.

3. A method of treating pain associated with wound healing in a subject having a wound comprising administering to the subject an amount of an inhibitor of CEP192 effective to treat pain associated with wound healing, wherein the inhibitor of CEP192 is a siRNA directed to CEP192 or a shRNA directed to CEP192.

4. The method of claim 1, wherein the CEP192 is a human CEP192.

5. The method of claim 1, wherein the siRNA is administered.

6. The method of claim 1, wherein the shRNA is administered.

7. The method of claim 5, wherein the siRNA is administered as a composition comprising the siRNA associated with a nanoparticle.

8. The method of claim 6, wherein the shRNA is administered as a composition comprising the shRNA encapsulated with a nanoparticle.

9. The method of claim 7, wherein the nanoparticle is PEGylated.

10. The method of claim 5, wherein the siRNA is administered as a viral vector.

11. The method of claim 6, wherein the shRNA is administered as a viral vector.

12. The method of claim 1, wherein the cancer is an osteosarcoma.

13. The method of claim 1, wherein the cancer is an anaplastic thyroid carcinoma.

14. The method of claim 1, wherein the cancer is large cell lung cancer.

15. The method of claim 2, wherein the fibrosis is in response to an injury.

16. The method of claim 2, wherein the fibrosis is a fibroma, pulmonary fibrosis, cystic fibrosis, hepatic cirrhosis, endomyocardial fibrosis, from a previous myocardial infarction, atrial fibrosis, mediastinal fibrosis, myelofibrosis, retroperitoneal fibrosis, progressive massive fibrosis of the lungs, a complication of pneumoconiosis, nephrogenic systemic fibrosis, Crohn's disease fibrosis, keloid fibrosis, scleroderma/systemic sclerosis of skin or lungs, arthrofibrosis or adhesive capsulitis fibrosis.

17. The method of claim 2, wherein the scarring is skin scarring, cardiovascular scarring, cardiac tissue scarring or neuronal scarring.

18. The method of claim 3, wherein the wound is a skin wound, cardiovascular wound, cardiac tissue scarring or neuronal wound.

* * * * *

UNITED STATES PATENT AND TRADEMARK OFFICE
CERTIFICATE OF CORRECTION

PATENT NO.       : 10,087,446 B2
APPLICATION NO.  : 15/706849
DATED            : October 2, 2018
INVENTOR(S)      : Sharp et al.

Page 1 of 1

It is certified that error appears in the above-identified patent and that said Letters Patent is hereby corrected as shown below:

On the Title Page

Item (12):
"Sharp" should read -- Sharp, et al. --.

Item (72) Inventor is corrected to read:
-- David Sharp, Scardale (NY);
Brian O'Rourke, New York (NY) --.

Signed and Sealed this
Eleventh Day of June, 2019

Andrei Iancu
*Director of the United States Patent and Trademark Office*

UNITED STATES PATENT AND TRADEMARK OFFICE
CERTIFICATE OF CORRECTION

| | |
|---|---|
| PATENT NO. | : 10,087,446 B2 |
| APPLICATION NO. | : 15/706849 |
| DATED | : October 2, 2018 |
| INVENTOR(S) | : David Sharp |

Page 1 of 1

It is certified that error appears in the above-identified patent and that said Letters Patent is hereby corrected as shown below:

In the Specification

In Column 1, Lines 18-25, delete and replace with the following:
STATEMENT OF GOVERNMENT SUPPORT
This invention was made with government support under grant number GM065940 awarded by the National Institutes of Health and grant number W81XWH-12-1-0379 awarded by the DHA/MRDB. The government has certain rights in the invention.

Signed and Sealed this
Eighteenth Day of November, 2025

John A. Squires
*Director of the United States Patent and Trademark Office*